US012788854B2

(12) United States Patent
Hutter et al.

(10) Patent No.: US 12,788,854 B2
(45) Date of Patent: Nov. 10, 2026

(54) DETECTOR ASSEMBLY AND METHOD

(71) Applicant: CAMBRIDGE ENTERPRISE LIMITED, Cambridge (GB)

(72) Inventors: Tanya Hutter, Cambridge (GB); Farah Alimagham, Cambridge (GB); Keri Carpenter, Cambridge (GB); Peter Hutchinson, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 796 days.

(21) Appl. No.: 17/774,885

(22) PCT Filed: Nov. 6, 2020

(86) PCT No.: PCT/GB2020/052815
§ 371 (c)(1),
(2) Date: May 6, 2022

(87) PCT Pub. No.: WO2021/090017
PCT Pub. Date: May 14, 2021

(65) Prior Publication Data

US 2022/0387680 A1 Dec. 8, 2022

(30) Foreign Application Priority Data

Nov. 6, 2019 (GB) ...................................... 1916168

(51) Int. Cl.
*A61M 1/14* (2006.01)
*A61M 1/16* (2006.01)
*G01N 21/3577* (2014.01)

(52) U.S. Cl.
CPC ............ *A61M 1/154* (2022.05); *A61M 1/155* (2022.05); *A61M 1/16* (2013.01); *A61M 1/1601* (2014.02);
(Continued)

(58) Field of Classification Search
CPC ........ A61M 1/154; A61M 1/155; A61M 1/16; A61M 1/1601; A61M 1/1605;
(Continued)

(56) References Cited

U.S. PATENT DOCUMENTS

2007/0258083 A1* 11/2007 Heppell ............. A61B 5/14532 356/39
2007/0273867 A1* 11/2007 Diessel .............. G01N 21/3577 356/36

(Continued)

FOREIGN PATENT DOCUMENTS

GB 2538731 A 11/2016
WO 2012/009554 A1 1/2012

OTHER PUBLICATIONS

International Search Report and Written Opinion for International Patent Application No. PCT/GB2020/052815 dated Feb. 25, 2021, 11 pages.

(Continued)

*Primary Examiner* — Rebecca E Eisenberg
*Assistant Examiner* — Timothy L Flynn
(74) *Attorney, Agent, or Firm* — Michele M. Glessner; Womble Bond Dickinson (US) LLP

(57) ABSTRACT

Provided is a detector assembly for determining a ratio of lactate to pyruvate from dialysis, said detector assembly comprising: a first pump, a dialysis probe, a first tube fluidically coupling the first pump to an inlet of the dialysis probe, an infrared (IR) detector, a second tube fluidically coupling an outlet of the dialysis probe to the IR detector, and a controller. The first pump pumps a perfusate at a first flow rate to the dialysis probe, via the first tube, and to, in turn, pump a dialysate at a second flow from the dialysis probe to the IR detector, via the second tube. The IR detector detects respective absorbances due to lactate and pyruvate in
(Continued)

the dialysate, and the controller determines the ratio of lactate to pyruvate in the dialysate.

31 Claims, 30 Drawing Sheets

(52) U.S. Cl.
CPC ....... *A61M 1/1605* (2014.02); *G01N 21/3577* (2013.01); *A61M 2205/3313* (2013.01); *A61M 2205/3334* (2013.01)

(58) Field of Classification Search
CPC .. A61M 2205/3313; A61M 2205/3334; G01N 21/3577; A61B 5/6814; A61B 5/6852; A61B 2505/03; A61B 5/4064; A61B 5/14514; A61B 5/14532; A61B 5/14546; A61B 5/0075; A61B 5/14525; A61B 5/1459; A61B 5/14528; A61B 5/1451

See application file for complete search history.

(56) References Cited

U.S. PATENT DOCUMENTS

| | | | | |
|---|---|---|---|---|
| 2010/0331727 | A1* | 12/2010 | Lindgren | A61B 10/0045 604/500 |
| 2013/0041242 | A1* | 2/2013 | Karlsson | A61B 5/412 600/365 |
| 2013/0131470 | A1* | 5/2013 | Galinkin | A61B 5/14528 600/310 |
| 2018/0125399 | A1* | 5/2018 | Joseph | A61M 27/002 |
| 2018/0136247 | A1* | 5/2018 | Boutelle | G01N 35/00693 |
| 2020/0291364 | A1* | 9/2020 | Mootha | A61K 35/18 |
| 2020/0355605 | A1* | 11/2020 | Causey, III | A61B 5/157 |

OTHER PUBLICATIONS

Great Britain Search Report for British Application No. GB1916168.6 dated May 4, 2020, 1 page.

Ralph James et al., "Advanced neurological monitoring", Surgery, vol. 34, No. 2, dated Feb. 28, 2016, pp. 94-96.

Khellaf Abdelhakim et al., "Recent advances in traumatic brain injury", Journal of Neurology—Zeitschrift Fuer Neurologie, Springer Verlag, Berlin, DE, vol. 266, No. 11, dated Sep. 28, 2019, pp. 2878-2889.

* cited by examiner

A

B

A B C

DETECTOR ASSEMBLY AND METHOD

CROSS-REFERENCE TO RELATED APPLICATIONS

This application is a National Stage Patent Application (filed under 35 § U.S.C. 371) of PCT/GB2020/052815, filed Nov. 6, 2020 of the same title, which, in turn claims priority to British Patent Application No. 1916168.6 filed Nov. 6, 2019 of the same title; the contents of each of which are hereby incorporated by reference.

FIELD OF THE INVENTION

The present invention relates to a detector assembly for, and a method of, determining a ratio of lactate to pyruvate from dialysis.

BACKGROUND OF THE INVENTION

Point-of-care (POC) monitoring of intensive care patients, for example, is typically based on intermittent testing, even when samples are continuously collected. POC monitoring approaches may be broadly classified into three types: implantable needle-type sensors, minimally invasive sensors based on microdialysis or transdermal fluid transport, and non-invasive optical spectroscopic sensors. Typically, the implantable sensors are limited due to progressive sensor fouling, bio-incompatibility, frequent re-calibrations and/or insufficient sensor lifetime, while the non-invasive sensors are limited due to high background absorption of water, instrumental drift, lack of sensitivity, overfitting during calibration, poor precision and/or the effect of blood flow on the measurements. In contrast, the minimally invasive sensors, based on measuring concentrations of analytes of interest in interstitial or transdermal fluids, for example, are promising. However, a drawback of the minimally invasive sensors is variable recovery rate of the analytes of interest, requiring use of recovery markers, such as acetate or mannitol, in an isotonic perfusate.

The clinical application of microdialysis has become feasible with the introduction of commercially available microdialysis catheters. These catheters mimic blood capillaries, where the analyte transport is based on diffusion through a semipermeable membrane. In most cases, microdialysis probes are placed subcutaneously to allow compounds of low relative molecular mass, such as glucose from the interstitial fluid, to penetrate the dialysis membrane into the dialysate. Using a continuous or discontinuous flow of the isotonic perfusate, the harvested dialysate can be transported to an extracorporeal measuring device, such as an ISCUSflex Microdialysis Analyzer (available from M Dialysis AB, Sweden). However, the time lag between sampling and signal detection and the tissue reaction after the insertion of a microdialysis catheter into the subcutaneous adipose tissue are the major limitations. Alternatively, the subcutaneous body interface can be replaced by a vascular body interface that includes a double-lumen venous catheter in combination with whole blood dilution using a heparin solution. The diluted whole blood can be transported to a flow-through dialysis cell, where the harvesting of analytes across a flat microdialysis membrane takes place at high recovery rates. The dialysate again can be transported to an extra-corporeal sensor.

In addition to the different approaches of in vivo microdialysis, using either subcutaneously implanted micro-dialysis catheters or intravascularly inserted probes, ex vivo extracorporeal microdialysis of continuously sampled and heparinized whole blood may be performed, from which dialysates can be harvested without a larger time delay.

Infrared (IR) spectroscopy is often successfully exploited for clinical chemistry applications due to its inherent reagent-free multi-analyte capability for whole blood, interstitial fluid or dialysate measurements. A combination of micro-dialysis and IR spectroscopy has been shown to be applicable for patient monitoring. For analysis, multivariate calibration methods are typically required for concentration determinations, using recovery markers, of analytes such as glucose, lactate, urea and others, requiring that broad spectral intervals should be recorded for reliable quantification.

Hence, there is a need to improve monitoring of bodily fluids and/or organs, for example of intensive care patients.

SUMMARY OF THE INVENTION

It is one aim of the present invention, amongst others, to provide a detector assembly and a method which at least partially obviates or mitigates at least some of the disadvantages of the prior art, whether identified herein or elsewhere. For instance, it is an aim of embodiments of the invention to provide a detector assembly for determining a ratio of lactate to pyruvate from dialysis, preferably microdialysis for example cerebral microdialysis, that has a smaller time lag between sampling and determining the ratio (i.e. signal detection), that is more suitable for at POC and/or that determines the ratio more frequently and/or continuously, compared with conventional detector assemblies. For instance, it is an aim of embodiments of the invention to provide a method of determining a ratio of lactate to pyruvate from dialysis, preferably microdialysis for example cerebral microdialysis, having an improved accuracy and/or precision, for lower concentrations of lactate and/or pyruvate, and/or that does not require a recovery marker, compared with conventional methods.

A first aspect provides a detector assembly for determining a ratio of lactate to pyruvate from dialysis, preferably microdialysis for example cerebral microdialysis, the detector assembly comprising:

- a first pump of a set of pumps, a dialysis probe, preferably a microdialysis probe, having an inlet and an outlet, a first tube of a set of tubes arranged to fluidically couple the first pump to the inlet of the dialysis probe, an infrared, IR, detector, a second tube of the set of tubes arranged to fluidically couple the outlet of the dialysis probe to the IR detector and a controller;
- wherein the first pump is arranged to pump a perfusate at a first flow rate of a set of flow rates to the dialysis probe, inserted into a fluid, for example a bodily fluid, and/or an organ of and/or for a patient, via the first tube and to in turn pump, at least in part, a dialysate at a second flow rate of the set of flow rates from the dialysis probe to the IR detector via the second tube;
- wherein the IR detector is arranged to detect respective absorbances due, at least in part, to lactate and pyruvate in the dialysate; and
- wherein the controller is arranged to determine the ratio of lactate to pyruvate in the dialysate based, at least in part, on the detected respective absorbances.

A second aspect provides a method of determining a ratio of lactate to pyruvate from dialysis, preferably microdialysis for example cerebral microdialysis, the method comprising:

- pumping, by a first pump of a set of pumps, a perfusate at a first flow rate of a set of flow rates to a dialysis probe, preferably a microdialysis probe, inserted into a fluid, for example a bodily fluid, and/or an organ of and/or for a patient, via a first tube of a set of tubes and in turn pumping, at least in part, a dialysate at a second flow rate of the set of flow rates from the dialysis probe to an infrared, IR, detector via a second tube of the set of tubes;

detecting, by the IR detector, respective absorbances due, at least in part, to lactate and pyruvate in the dialysate; and determining, by a controller, the ratio of lactate to pyruvate in the dialysate based, at least in part, on the detected respective absorbances.

BRIEF DESCRIPTION OF THE DRAWINGS

For a better understanding of the invention, and to show how exemplary embodiments of the same may be brought into effect, reference will be made, by way of example only, to the accompanying diagrammatic Figures, in which:

FIG. 26A: spectra excluding outliers; and FIG. 26B: spectra used for the PLSR model after preprocessing;

FIG. 27A: glucose; FIG. 27B: lactate; and FIG. 27V: pyruvate. Predicted values were derived from applying the PLSR model to the test set. Dashed lines represent a linear regression fit;

FIG. 28A: raw spectra; and FIG. 28B: spectra with preprocessing applied;

FIG. 29A: glucose; and FIG. 29B: lactate. Predicted values were derived from applying the PLSR model to the absorbance spectra of the patient samples. Dashed lines represent a linear regression fit;

FIG. 30A glucose; and FIG. 30B lactate. Predicted values were derived from applying the PLSR model to the absorbance spectra of the patient 2 samples. FIG. 30C glucose; and FIG. 30D lactate. Predicted values were derived from applying the PLSR model to the absorbance spectra of the patient 1 samples.

DETAILED DESCRIPTION OF THE INVENTION

Figure 1:
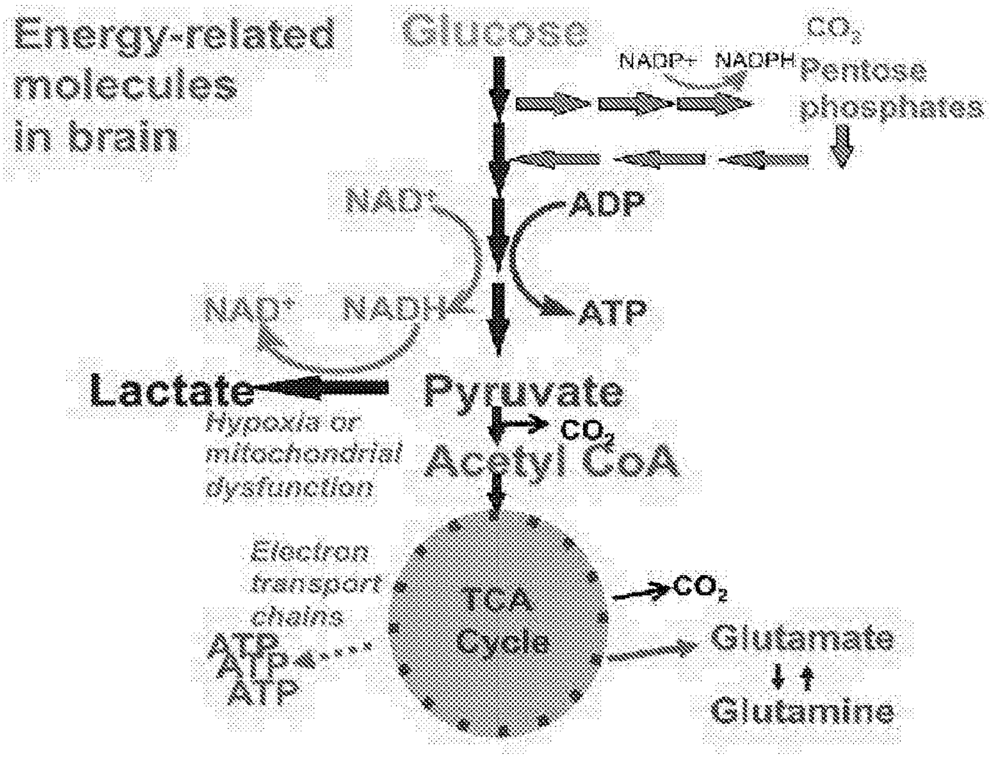
FIG. 1 schematically depicts the glycolysis mechanism and the tricarboxylic acid cycle (TCA) cycle.

According to the present invention there is provided a detector assembly, as set forth in the appended claims. Also provided is a method. Other features of the invention will be apparent from the dependent claims, and the description that follows.

Detector Assembly

The first aspect provides a detector assembly for determining a ratio of lactate to pyruvate from dialysis, preferably microdialysis for example cerebral microdialysis, the detector assembly comprising:

a first pump of a set of pumps, a dialysis probe, preferably a microdialysis probe, having an inlet and an outlet, a first tube of a set of tubes arranged to fluidically couple the first pump to the inlet of the dialysis probe, an infrared, IR, detector, a second tube of the set of tubes arranged to fluidically couple the outlet of the dialysis probe to the IR detector and a controller;

wherein the first pump is arranged to pump a perfusate at a first flow rate of a set of flow rates to the dialysis probe, inserted into a fluid, for example a bodily fluid, and/or an organ of and/or for a patient, via the first tube and to in turn pump, at least in part, a dialysate at a second flow rate of the set of flow rates from the dialysis probe to the IR detector via the second tube;

wherein the IR detector is arranged to detect respective absorbances due, at least in part, to lactate and pyruvate in the dialysate; and wherein the controller is arranged to determine the ratio of lactate to pyruvate in the dialysate based, at least in part, on the detected respective absorbances.

In this way, the ratio of lactate to pyruvate (L:P) in the dialysate is determined from the respective absorbances detected by the IR detector. Particularly, for traumatic brain injury (TBI), the L:P ratio may be a significant independent predictor of outcome in patients with subarachnoid hemorrhage. As described below in more detail, the determining of the ratio of lactate to pyruvate from the dialysis may have a smaller time lag between sampling and determining the ratio, that is more suitable for at POC and/or that determines the ratio more frequently and/or continuously, compared with conventional detector assemblies. As described below in more detail, the determining of the ratio of lactate to pyruvate from dialysis may have an improved accuracy and/or precision, is suitable for lower concentrations of lactate and/or pyruvate, and/or does not require a recovery marker, compared with conventional methods.

In more detail, TBI remains a major cause of mortality, morbidity and long-term disability, with profound and often long-lasting social and economic consequences. It is recognized that outcome following TBI is related to the initial characteristics of injury, reflecting its severity, such as Glasgow Coma Scale score, pupillary reactivity and radiological appearance, as well as the patient's age and presence or absence of early physiological insults (hypoxia and hypotension). This relationship of early and largely non-modifiable factors to mortality and neurological outcome has been confirmed by the analysis of demographic data from the several large randomized controlled trials and has led to development of prognostic scoring systems, which can be used to predict outcome at a group level. Nevertheless, outcomes are also influenced by ongoing pathophysiological processes and secondary insults that continue to take place after initial injury and resuscitation. Detection of these secondary events remains a major target of neuromonitoring and an area of ongoing research. Intracranial pressure and cerebral perfusion pressure are the most widely accepted neuromonitoring parameters and have been shown in many studies to be related to mortality after TBI. More recently cerebral autoregulation and brain tissue oximetry have been linked to outcome after head injury. Although there is no conclusive proof that optimization of these parameters may influence neurological recovery, indirect evidence of better outcomes in specialized neurocritical care units, where tiered therapy is based on neuromonitoring, supports their use and further exploration of their clinical value. Direct monitoring of cerebral extracellular chemistry by microdialysis is a promising technique that has enhanced understanding of the pathophysiology of brain injury and is maturing as a clinical monitor that can be employed in combination with other monitoring methods (such as cerebral oximetry and intracranial pressure monitoring) to assist in the management of patients on an individual intention-to-treat basis.

Generally, the blood L:P molar ratio reflects the equilibrium between product and substrate of the reaction catalyzed by lactate dehydrogenase. The L:P ratio is correlated with the cytoplasmic NADH:$NAD^+$ ratio and is used as a surrogate measure of the cytosolic oxido-reduction state. When cellular respiration is impaired, as in hypoxia, pyruvate oxidation is reduced, resulting in lactic acidosis. In such situations, reduced forms of oxido-reduction coenzymes (NADH, $FADH_2$) predominate and L:P ratio is increased. A similar impairment of the oxidative metabolism occurs in inborn errors of the mitochondrial respiratory chain. In contrast, in pyruvate dehydrogenase deficiency (PDH-D), the metabolic block is upstream of the respiratory chain, and thus the cytoplasmic oxido-reduction state is predicted to be unaltered and the L:P ratio is normal or low. In other words, the L:P ratio may be used to distinguish between pyruvate dehydrogenase deficiency and other causes of congenital lactic acidosis. Usually, an L:P molar ratio >25 is considered increased and suggestive of a primary (or secondary) respiratory chain dysfunction, whereas a ratio <20 is thought to be consistent with PDH-D. Rapid distinction between PDH-D and respiratory chain diseases is desirable because there are specific treatments for PDH-D. In conjunction with an elevated lactate, an L:P ratio greater than 30 suggests inherited disorders of the respiratory chain complex or tricarboxylic acid cycle disorders. An abnormally high L:P ratio can be observed in acutely ill individuals.

In brain extracellular fluid, the L:P ratio is regarded as an important indicator of the brain's metabolic state and shows statistical association with clinical outcome. In patients with subarachnoid hemorrhage, both the L:P ratio and glutamate concentration may be significant independent predictors of clinical outcome along with known strong predictors, such as age and World Federation of Neurosurgical Societies grade. In patients with traumatic brain injury (TBI), a consistent finding, including temporal changes and multivariate analysis, is the significant association of higher L:P ratio with increased mortality and unfavorable clinical outcomes. The L:P ratio reflects the metabolic state, and the elevation of L:P ratio may reflect the presence of either mitochondrial dysfunction or lack of oxygen supply, due to ischemia or hypoxia. In the modern setting of protocol-driven neurocritical care true ischemic states are rare occurrences. Nevertheless, the analysis of individual patients' temporal patterns of L:P ratio and other markers often reveals fluctuating values reflecting clinical course and changing energy metabolism. In addition, persistent abnormalities that are refractory to clinical interventions are also common, especially in the vicinity of the injured cerebral tissue. Both of these static and dynamic metabolic abnormalities can have an impact on survival and clinical outcome. Data support such a link, demonstrating persistently higher L:P ratio in non-survivors and in patients with unfavorable clinical outcomes, particularly a physiological threshold of L:P ratio=25 as a discriminator, with higher threshold of 40 not adding significant value to the model. It is also possible to suggest that early after the injury, at least within the first 72 h, the changes in L:P ratio and other markers have a stronger association with outcome, possibly due to the period of unstable physiology and maximum tissue vulnerability soon after the injury. During these early periods, the L:P ratio can differentiate between survival categories, and moreover can discriminate between favorable and unfavorable clinical outcome groups. A significant difference in L:P ratio and other microdialysis markers between the favorable and unfavorable outcome cohorts is also more pronounced in patients with isolated head injury, probably because major extracranial injury is likely to influence functional outcome, diluting the effects of deranged cerebral biochemistry.

The biological significance of the L:P ratio is incompletely understood. Originally, a high L:P ratio was interpreted as ischemia, but more recently it has also come to be regarded as arising from mitochondrial dysfunction, although the precise biological and biochemical details of this dysfunction in patients with TBI remain unclear. Evidence from experimental models of TBI indicates various mitochondrial abnormalities microscopically and biochemically. The L:P ratio in patients with TBI can be regarded as a surrogate marker based on statistics, and is clearly not 100% selective for outcome. Even so, the incidence (%) of the L:P ratio >25 emerges as a much better discriminator between outcome groups than incidence (%) of L:P ratio >40.

The following physiological thresholds may be used to calculate the time periods of abnormal values: intracranial pressure >25 mmHg, cerebral perfusion pressure <60 mmHg, PRx >0.2, glucose <1.0 mmol/l, lactate >4 mmol/l, pyruvate <50 μmol/l, glutamate >10 μmol/l, glycerol >150 μmol/l, L:P ratio >25 and >40 and lactate/glucose ratio >10.

Detector Assembly

The detector assembly is suitable for determining the ratio of lactate to pyruvate from the dialysis, preferably microdialysis for example cerebral microdialysis. It should be understood that the detector assembly may be suitable for determining ratios and/or concentrations of other analytes of interest (such as lactate and pyruvate), for example in vivo of bodily fluids and/or organs and/or ex vivo, such as for monitoring health of transplant organs from human and/or non-human donors and/or synthetic organs synthesized by organic growth and/or by additive manufacturing. In one example, the ratio of lactate to pyruvate comprises and/or is a molar ratio.

Set of Pumps

The detector assembly comprises the first pump of the set of pumps. In other words, the detector assembly comprises the set of pumps including the first pump. Pumps for dialysis probes, preferably microdialysis probes, are known. Suitable pumps are available from Harvard Apparatus (USA), such as CMA 402 Microdialysis Syringe Pump and CMA 4004 Microdialysis Syringe Pump, which are for use in animals or other non-human situations. Pumps suitable for use in humans are from M Dialysis AB, Stockholm, Sweden: pump models are M Dialysis 106 (fixed flow rate at 0.3 μL/min) and M Dialysis 107 (adjustable flow rate, which can be selected at any one of eight values: 0.1 μL/min, 0.2 μL/min, 0.3 μL/min, 0.5 μL/min, 1.0 μL/min, 2.0 μL/min or 5.0 μL/min). In one example, the first pump comprises and/or is a syringe pump, such as a single channel syringe pump or a dual channel syringe pump, and/or a peristaltic pump. Preferably, the first pump provides non-pulsatile flow characteristics. In contrast, pulsatile flow may adversely affect signal detection, including baseline measurements. In one example, the set of pumps includes P pumps, including the first pump, wherein P is a natural number greater than or equal to 1, for example 1, 2, 3, 4, 5, 6, 7, 8, 9, 10 or more. The P pumps may be as described with respect to the first pump.

The first pump is arranged to pump the perfusate at the first flow rate of the set of flow rates to the dialysis probe, inserted into the fluid, for example a bodily fluid, and/or the organ of and/or for the patient, via the first tube and to in turn pump, at least in part, the dialysate at the second flow rate of the set of flow rates from the dialysis probe to the IR detector via the second tube. Generally, the second flow rate is substantially the same, preferably the same, as the first flow rate. That is, the flow rate of the dialysate out of the dialysis probe is substantially the same, preferably the same, as the flow rate of the perfusate into the dialysis probe.

In one example, the first flow rate is an a range from 0.01 μL/min to 250 μL/min, preferably in a range from 0.05 μL/min to 100 μL/min, more preferably in a range from 0.1 μL/min to 50 μL/min, most preferably in a range from 0.2 μL/min to 1 μL/min, for example 0.3 μL/min. The second flow rate may be as described with respect to the first flow rate. It should be understood that the first flow rate may be selected according to a type and/or size of the dialysis probe. By increasing the first flowrate and hence the second flowrate, a time lag between sampling and signal detection may be reduced. However, by increasing the first flowrate and hence the second flowrate, recovery of an analyte of interest, for example lactate and/or pyruvate, may be reduced, thereby degrading a signal to noise ratio of the respective analyte of interest. Typically, for cerebral microdialysis, the first flow rate and/or the second flowrate of about 0.3 μL/min is preferred.

In one example, the set of pumps comprises a second pump arranged to pump, at least in part, the dialysate at the second flow rate of the set of flow rates from the dialysis probe to the IR detector via the second tube, wherein the second flow rate is greater than the first flow rate. In this way, the dialysate may be pumped more quickly from the outlet of the dialysis probe to the IR detector, thereby reducing a time lag between sampling and signal detection.

Dialysis Probe

The detector assembly comprises a dialysis probe, preferably a microdialysis probe, having an inlet and an outlet. Dialysis probes and microdialysis probes are known. Suitable microdialysis probes are available from Harvard Apparatus (MA, USA) and BASi (IN, USA), which are for use in animals or other non-human situations. Microdialysis probes—also known as microdialysis catheters—suitable for use in humans are available from M Dialysis AB, Stockholm, Sweden. Microdialysis probe models for use in human brain are M Dialysis 71 (100 kDa nominal molecular weight cutoff) and M Dialysis 70 (20 kDa nominal molecular weight cutoff). Microdialysis probes (catheters) optimized for other organs and tissues are also available from M Dialysis, including M Dialysis 61 (hepatic), M Dialysis 62 (gastrointestinal), M Dialysis 63 (adipose tissue, resting skeletal muscle, hepatic tissue), 66 (skin, adipose and resting skeletal muscle) and M Dialysis 67 IV (intravenous, for blood monitoring). It should be understood that the perfusate enters the inlet and the dialysate exits the outlet.

Generally, microdialysis is a minimally-invasive sampling technique that is used for measurement of free, unbound analyte concentrations in extracellular fluid of tissues. Analytes may include endogenous molecules (e.g. neurotransmitters, hormones, cytokines, glucose, etc.) to assess their biochemical functions in the body, or exogenous compounds (e.g. pharmaceuticals) to determine their distribution within the body. Microdialysis requires insertion of a microdialysis catheter (also known as a microdialysis probe) into the bodily fluid or tissue (i.e. the organ) of interest. The microdialysis probe is designed to mimic a blood capillary and comprises a shaft with a semipermeable hollow fiber membrane at its tip, which is connected to inlet and outlet tubing. The microdialysis probe is continuously perfused with an aqueous solution (i.e. the perfusate) that closely resembles the (ionic) composition of the surrounding tissue fluid at a low flow rate of approximately 0.1-5 μL/min. Once inserted into the tissue or fluid of interest, small solutes can cross the semipermeable membrane by passive diffusion. The direction of the analyte flux is determined by the respective concentration gradient and allows the usage of microdialysis probes as sampling as well as delivery tools. The solution leaving the probe (dialysate) is conventionally collected at certain time intervals for analysis.

There are a variety of probes with different membrane and shaft length combinations available. The molecular weight cut-off of commercially available microdialysis probes covers a wide range of approximately 6-100 kDa, but also 1000 kDa is available, for example for pre-clinical and/or animal applications. While water-soluble compounds generally diffuse freely across the microdialysis membrane, the situation is not as clear for highly lipophilic analytes, where both successful (e.g. corticosteroids) and unsuccessful microdialysis experiments (e.g. estradiol, fusidic acid) have been reported. However, the recovery of water-soluble compounds usually decreases rapidly if the molecular weight of the analyte exceeds 25% of the membrane's molecular weight cut-off.

Set of Tubes

The detector assembly comprises the set of tubes, including the first tube arranged to fluidically couple the first pump to the inlet of the dialysis probe and the second tube arranged to fluidically couple the outlet of the dialysis probe to the IR detector. In other words, the first pump is in fluid communication with the IR detector via the first tube, the dialysis probe and the second probe. In one example, the first tube has an internal diameter (ID, also known as a bore) in a range from 10 μm to 1,000 μm, preferably in a range from 50 μm to 500 μm, more preferably in a range from 100 μm to 250 μm, for example 150 μm. In one example, the first tube has a length in a range from 10 mm to 1,000 mm, preferably in a range from 50 mm to 500 mm, more preferably in a range from 100 mm to 250 mm. In one example, the second tube has a length in a range from 10 mm to 1,000 mm, preferably in a range from 50 mm to 500 mm, more preferably in a range from 100 mm to 750 mm, for example 600 mm. Generally, it is preferred to reduce the length of the first tube and/or the second tube. For example, by reducing the length of the second tube, a time lag between sampling and signal detection may be reduced. In one example, the first tube comprises and/or is a flexible tube. The second tube may be as described with respect to the first tube. In one example, an internal diameter and/or a length of the first tube and/or the second tube is selected to decrease, for example minimize, a dwell volume of the respective tube. In this way, a time lag between sampling and signal detection may be reduced, for example reducing a volume of the second tube (and hence of the dialysate) between the dialysis probe and the IR detector. In one example, an internal diameter and/or a length of the first tube and/or the second tube is selected to increase, for example maximize, a signal to noise ratio (SNR) of the detect respective absorbances, for example by reducing the diameter of the second tube so as to reduce spreading (i.e. band spreading) of the lactate and/or pyruvate in the dialysate between the dialysis probe and the IR detector. In one example, the first tube comprises PEEK. In one example, the set of tubes includes T tubes, including the first tube and the second tube, wherein T is a natural number greater than or equal to 2, for example 2, 3, 4, 5, 6, 7, 8, 9, 10 or more. The T tubes may be as described with respect to the first tube. For example, suitable tubing is available from PEEK tubing KIT 0.15 mm ID, 1.6 mm OD, catalogue no. 18115659, GE Healthcare Life Sciences.

IR Detector

The detector assembly comprises the infrared, IR, detector. IR detectors are known. Suitable IR detectors are available from DRS Daylight Solutions Inc (San Diego, CA USA). In one example, the IR detector comprises and/or is an IR spectrometer, arranged to detect IR absorbances for a range of wavenumbers. In one example, the IR detector comprises and/or is a tuneable IR detector, arranged to detect IR absorbances for selected wavenumbers. In one example, the IR detector comprises and/or is a mid IR, MIR, detector. In one preferred example, the IR detector comprises and/or is a quantum cascade laser, QCL, based IR detector. In this way, lower concentrations of lactate and/or pyruvate, for example, may be detected due to a higher power of the QCL IR beam, compared with conventional IR detectors.

In contrast to chemical assays for measuring respective concentrations of lactate and pyruvate, for example, IR detection is non-destructive such that the dialysate may be collected for other analyses, after IR analysis using the IR detector.

In one example, the IR detector comprises a flow cell for flow of the dialysate therethrough. In one example, the flow cell has a path length in a range from 10 μm to 1000 μm, preferably in a range from 25 μm to 500 μm, more preferably in a range from 50 μm to 250 μm, for example 76 μm, 127 μm, 152 μm or 203 μm. Generally, a relatively longer path length is preferred, enabling detection of analytes of interest at relatively lower concentrations for a given intensity of the IR beam. However, as the path length is increased further, scattering of the IR beam, for example, by the dialysate reduces a detection limit. Hence, the path length may be selected according to an intensity of the IR beam and/or the dialysate, for example. QCL based IR detectors, for example, generate IR beams having relatively higher intensities, allowing selection of relatively longer path lengths and thus enabling detection of analytes of interest at relatively lower concentrations. In one example, the flow cell has a volume in a range from 0.01 μL to 50 μL, preferably in a range from 0.05 μL to 10 μL, more preferably in a range from 0.1 μL to 5 μL, for example 1 μL or <1 μL. Generally, a relatively smaller volume is preferred, enabling increased volumetric resolution. However, further reducing the volume may degrades a signal to noise ratio for the analytes of interest.

The IR detector is arranged to detect respective absorbances due, at least in part, to lactate and pyruvate in the dialysate. In one example, the IR detector is arranged to detect respective absorbances at one or more wavenumbers according to Table 1.

TABLE 1

Wavenumbers for detecting absorbance due to analytes of interest.

| Analyte of interest | Wavenumber(s) ($cm^{-1}$) |
|---|---|
| Lactate | 1042, 1126 |
| Pyruvate | 1176 |
| Glucose | 1036, 1080, 1108, 1152 |

Notably, absorbance due to mannitol overlaps with that due to glucose, adversely affecting use thereof as a recovery marker, for example. Use of mannitol as a microdialysis recovery marker is generally not widespread. Mannitol is not really a good choice as a recovery marker in this context, as mannitol may be administered therapeutically for other reasons, thereby precluding use of mannitol as a recovery marker. For example, intravenous mannitol is often used in the management of cerebral oedema and raised intracranial pressure (ICP) from various causes, e.g. TBI or hepatic encephalopathy. Mannitol is sometimes used for renal protection in cardiac and vascular surgery and during renal transplantation and in the management of rhabdomyolysis. Intravenous mannitol for managing ICP is regarded as acting as a hyperosmolar agent, drawing fluid out of the brain. The mannitol molecule is often regarded as not readily crossing the blood-brain barrier (BBB). However, it is also known that prolonged mannitol administration can disrupt the BBB (mannitol is sometimes used to improve delivery of drugs or stem cells across the BBB), and then the mannitol can enter the brain parenchyma.

In one example, the IR detector is arranged to detect respective absorbances due, at least in part, to lactate and pyruvate in the dialysate for an integration time in a range from 1 s to 1,000 s, preferably in a range from 5 s to 500 s, more preferably in a range from 10 s to 100 s. By reducing the integration time, the ratio of lactate to pyruvate may be determined more frequently. However, by increasing the integration time, an accuracy and/or a precision of the ratio of lactate to pyruvate may be improved. Hence, the integration time may be selected according to, for example, the concentrations of lactate and/or pyruvate in the dialysate, a signal to noise ratio for the lactate and/or pyruvate in the dialysate and/or a desired frequency of determining the ratio of lactate to pyruvate in the dialysate.

In one example, the IR detector is arranged to detect an absorbance due, at least in part, to other relevant molecules, for example glucose, glutamate, alanine, glutamine and/or glycerol, and other analytes of interest, in the dialysate. In this way, additional information about the bodily fluid and/or organ may be obtained concurrently and/or consecutively, thereby improving monitoring and/or diagnosis.

In one example, the IR detector comprises a flow cell arranged proximal to the outlet of the dialysis probe, for example within 500 mm, preferably within 250 mm, more preferably within 100 mm of the outlet of the dialysis probe (i.e. a length of the second tube is at most 500 mm, preferably at most 250 mm, more preferably at most 100 mm). In other words, the flow cell may be remote from the IR detector, coupled thereto via optical fibers for example. In this way, a time lag between sampling and signal detection may be reduced since the flow cell may be arranged relatively more proximal the outlet of the dialysis probe and hence the patient. In one example, the flow cell is fluidically coupled directly to the outlet of the dialysis probe.

Controller

The detector assembly comprises the controller. In one example, the controller comprises a processor and a memory, including instructions executable by the processor to perform functions of the controller, as described herein.

The controller is arranged to determine the ratio of lactate to pyruvate in the dialysate based, at least in part, on the detected respective absorbances (i.e. of lactate and pyruvate). In one example, the IR detector is arranged to transmit and/or store respective absorbances, for example as values, for lactate and pyruvate and the controller is arranged to receive and/or read the respective absorbances. In one example, the controller is arranged to determine the ratio of lactate to pyruvate in the dialysate as the ratio of the detected absorbance due to lactate to the detected absorbance due pyruvate. It should be understood that spectral interference, for example due to other analytes, may contribute to the respective detected absorbances, requiring correction thereof, for example according to a predetermined calibration curve, and/or database of spectra and spectral fitting algorithm.

Conventionally, application of microdialysis is often limited by the determination of the microdialysis probe's recovery, especially for in vivo experiments. Determination of the recovery may be time-consuming and may require additional subjects or pilot experiments. The recovery is largely dependent on the flow rate: the lower the flow rate, the higher the relative recovery (where relative recovery of the species of interest is defined as its concentration in the microdialysate, divided by its concentration in the extracellular fluid, and is usually expressed as a percentage). However, in practice the flow rate cannot be decreased too much since either the sample volume obtained for analysis will be insufficient or the temporal resolution of the experiment will be lost. It is therefore generally important to optimize the relationship between flow rate and sensitivity of the analytical assay. The situation may be more complex for lipophilic or hydrophobic compounds as they can stick to the microdialysis membrane, tubing or other probe components, resulting in a low or no analyte recovery.

Advantageously, by determining the ratio of lactate to pyruvate in the dialysate based, at least in part, on the detected respective absorbances, rather than the respective concentrations, changes in respective recoveries of the lactate and pyruvate are attenuated. Without wishing to be bound by any theory, changes in respective recoveries of the lactate and pyruvate tend to track or trend together, such that the determined ratio of lactate to pyruvate in the dialysate is relatively unaffected, thereby improving an accuracy and/or precision of the determined ratio. In this way, use of a recovery marker in the perfusate is not required. In one example, the perfusate does not include a recovery marker. Mannitol, for example, interferes with detection of glucose while other recovery markers may similarly affect detection of other analytes of interest. By avoiding use of a recovery marker, a complexity and/or cost of the perfusate is reduced, while eliminating potential spectral interferences.

In one example, the controller is arranged to control the set of pumps, the first pump, and/or the IR detector, for example by being unidirectionally or bidirectionally communicatively coupled thereto via wires and/or wirelessly.

In one example, the controller is arranged to provide a first output signal, based, at least in part, on the ratio of lactate to pyruvate in the dialysate for controlling infusion of an infusate, for example comprising glucose, into the fluid, for example a bodily fluid, and/or the organ of and/or for the patient the patient. In this way, based on the ratio of lactate to pyruvate in the dialysate, infusion of the infusate may be dynamically controlled, for example responsively and/or in real time, based on feedback from the dialysis, thereby improving organ health and/or patient outcome. For example, the controller may implement an algorithm that determines how much of the infusate is needed, and the ensuing instructions are sent automatically to an infusion pump that adjusts infusate delivery to the tissue, for example under the skin.

In one example, the controller is arranged to provide a second output signal, based, at least in part, on a change, preferably a rate of change, of a detected absorbance, for example of glucose. In this way, monitoring and/or diagnosis of the patient may be improved. For example, a reduction in glucose concentration in the dialysate may be associated with a comorbidity. Hence, the second output signal may be used as an indicator of such a comorbidity.

In one example, the controller is arranged to determine the ratio of lactate to pyruvate in the dialysate in response to a request, intermittently, periodically (for example every second, every S seconds, where S is a natural number greater than or equal to 1, every minute, every M minutes where M is a natural number greater than or equal to 1), frequently (for example in a frequency range from 0.001 Hz to 100 Hz) and/or continuously. In one example, the controller is arranged to determine the ratio of lactate to pyruvate in the dialysate online and/or in real time. In contrast, conventional detector assemblies for analysis of dialysates are offline, requiring manual transfer of the samples of dialysates from point of collection to a clinical microdialysis analyzer, situated either at the patient's bedside, or elsewhere in the ward, or in a laboratory. A suitable clinical microdialysis analyzer is the ISCUSflex (M Dialysis AB, Stockholm, Sweden). For intensive care patients, a frequency of conventional analysis is typically hourly; consequently, any rapid changes in the patient's condition may be missed. While somewhat shorter time intervals are possible, e.g. 15 or 30 minutes, these are even more labor-demanding for staff than the typical hourly readings. Moreover, the volumes of microdialysate collected in 15 or 30 minutes are inconveniently small. By determining the ratio of lactate to pyruvate in the dialysate online and/or in real time, for example periodically, frequently and/or continuously, patient outcome may be improved. This determining of the ratio of lactate to pyruvate in the dialysate online and/or in real time, for example periodically, frequently and/or continuously is enabled because the outlet of the dialysis probe is fluidically coupled to the IR detector via the second tube.

In one example, the controller is arranged to control the second pump to pump the perfusate at the first flow rate of the set of flow rates.

In one example, the controller is arranged to compare the ratio of lactate to pyruvate in the dialysate with respective output signals from a set of patient sensors including, for example, an oxygen sensor such as for cerebral oximetry and/or a pressure sensor such as for intracranial pressure monitoring. In this way, the ratio of lactate to pyruvate in the dialysate may be correlated with other sensed measurements of the patient.

Set of Valves

In one example, the detector assembly comprises a first valve of a set of valves arranged to direct the dialysate at the second flow rate of the set of flow rates from the outlet of the dialysis probe to the IR detector via the second tube. It should be understood that the first valve is thus arranged between the outlet of the dialysis probe and the IR detector, for example providing a selectable passageway in a pathway of the second tube. In this way, a portion of the dialysate may be diverted, for example by a heart cut valve, to the IR detector via the second tube for determination of the ratio of lactate to pyruvate from the diverted portion, while the remainder of the dialysate may be collected, for example for other analyses.

In one example, the detector assembly comprises a first valve of a set of valves arranged to direct the dialysate at the second flow rate of the set of flow rates from the outlet of the dialysis probe to the IR detector via the second tube and the set of pumps comprises a second pump arranged to pump, at least in part, the dialysate at the second flow rate of the set of flow rates from the dialysis probe to the IR detector via the second tube, wherein the second flow rate is greater than the first flow rate. In this way, a portion of the dialysate may be diverted, for example by a heart cut valve, to the IR detector via the second tube for determination of the ratio of lactate to pyruvate from the diverted portion, while the remainder of the dialysate may be collected, for example for other analyses. Furthermore, the portion of the dialysate diverted, for example by the heart cut valve, to the IR detector via the second tube may be pumped more quickly by the second pump from the first valve to the IR detector, thereby reducing a time lag between sampling and signal detection. In one example, the second pump is arranged to pump perfusate. In this way, the portion of the dialysate is between other portions of perfusate (i.e. serially).

Method

The second aspect provides a method of determining a ratio of lactate to pyruvate from dialysis, preferably microdialysis for example cerebral microdialysis, the method comprising:

- pumping, by a first pump of a set of pumps, a perfusate at a first flow rate of a set of flow rates to a dialysis probe, preferably a microdialysis probe, inserted into a fluid, for example a bodily fluid, and/or an organ of and/or for a patient, via a first tube of a set of tubes and in turn pumping, at least in part, a dialysate at a second flow rate of the set of flow rates from the dialysis probe to an infrared, IR, detector via a second tube of the set of tubes;
- detecting, by the IR detector, respective absorbances due, at least in part, to lactate and pyruvate in the dialysate; and
- determining, by a controller, the ratio of lactate to pyruvate in the dialysate based, at least in part, on the detected respective absorbances.

The ratio of lactate to pyruvate, the dialysis, the microdialysis, the cerebral microdialysis, the first pump of the set of pumps, the dialysis probe, the microdialysis probe, the first tube of the set of tubes, the IR detector, the second tube of the set of tubes, the controller, the first flowrate of the set of flowrates, the perfusate, the second flowrate, the dialysate and/or the respective absorbances may be as described with respect to the first aspect.

In one example, the method comprises:

- detecting, by the IR detector, an absorbance due, at least in part, to glucose in the dialysate; and
- determining, by the controller, a ratio of glucose to lactate in the dialysate based, at least in part, on the detected respective absorbances.

In one example, the method comprises:

- providing, by the controller, a first output signal, based, at least in part, on the ratio of lactate to pyruvate in the dialysate; and
- controlling infusion of an infusate into the fluid and/or the organ.

In one example, the method comprises:

- providing, by the controller, a second output signal, based, at least in part, on a change, preferably a rate of change, of a detected absorbance, for example of glucose.

In one example, the method comprises:

- detecting, by the IR detector, an absorbance due, at least in part, to glycerol in the dialysate.

In one example, the method comprises:

- controlling, by the controller, the first pump to pump the perfusate at the first flow rate of the set of flow rates.

In one example, the method comprises:

- pumping, by a second pump of the set of pumps, at least in part, the dialysate at the second flow rate of the set of flow rates from the dialysis probe to the IR detector via the second tube, wherein the second flow rate is greater than the first flow rate.

In one example, the method comprises:

- directing, by a first valve of a set of valves, the dialysate at the second flow rate of the set of flow rates from the dialysis probe to the IR detector via the second tube.

In one example, the perfusate does not include a recovery marker.

In one example, a concentration of the lactate in the dialysate is at most 10 millmol/L, preferably at most 8 millimol/L, more preferably at most 6 millimol/L, and preferably at least 1 millmol/L, while for pyruvate a concentration in the dialysate is at most 400 micromol/L, more preferably at most 200 micromol/L, and preferably at least 50 micromol/L.

In one example, the method comprises predicting respective concentrations of lactate, pyruvate and/or glucose in the dialysate using a model, for example a statistical model such as multivariate calibration including classical and inverse methods and/or supervised multivariate classification for example multivariate discriminant analysis, logistic regression, neural networks, regression/classification trees and/or Partial Least Squares Regression (PLSR), relating the respective absorbances and the respective concentrations. In this way, the respective concentrations of these analytes of interest may be estimated quantitatively and absolutely, for example without internal calibration and/or without analyzing calibration standards for each patient.

In one example, the method comprises generating the model using synthetic samples of the dialysate. In this way, the synthetic samples correspond with the dialysate such that the model is suitable for use with patient dialysate.

Definitions

Throughout this specification, the term "comprising" or "comprises" means including the component(s) specified but not to the exclusion of the presence of other components. The term "consisting essentially of" or "consists essentially of" means including the components specified but excluding other components except for materials present as impurities, unavoidable materials present as a result of processes used to provide the components, and components added for a purpose other than achieving the technical effect of the invention, such as colorants, and the like.

The term "consisting of" or "consists of" means including the components specified but excluding other components.

Whenever appropriate, depending upon the context, the use of the term "comprises" or "comprising" may also be taken to include the meaning "consists essentially of" or "consisting essentially of", and also may also be taken to include the meaning "consists of" or "consisting of".

The optional features set out herein may be used either individually or in combination with each other where appropriate and particularly in the combinations as set out in the accompanying claims. The optional features for each aspect or exemplary embodiment of the invention, as set out herein are also applicable to all other aspects or exemplary embodiments of the invention, where appropriate. In other words, the skilled person reading this specification should consider the optional features for each aspect or exemplary embodiment of the invention as interchangeable and combinable between different aspects and exemplary embodiments.

Detailed Description of the Drawings

FIG. 1 depicts a simplified schematic of major energy pathways in the brain include glycolysis, which takes places in the cytosol and produces pyruvate, which enters mitochondria and is converted into acetyl CoA that enters the TCA cycle. Alternatively, pyruvate can stay in the cytosol and is converted into lactate that is exported out of the cell. The pentose phosphate pathway (PPP) takes place in the cytosol and is an alternative energy pathway that can be up-regulated after injury; it is an important source of NADPH used to produce the reduced form of glutathione (GSH) for preventing oxidative stress.

Figure 2:
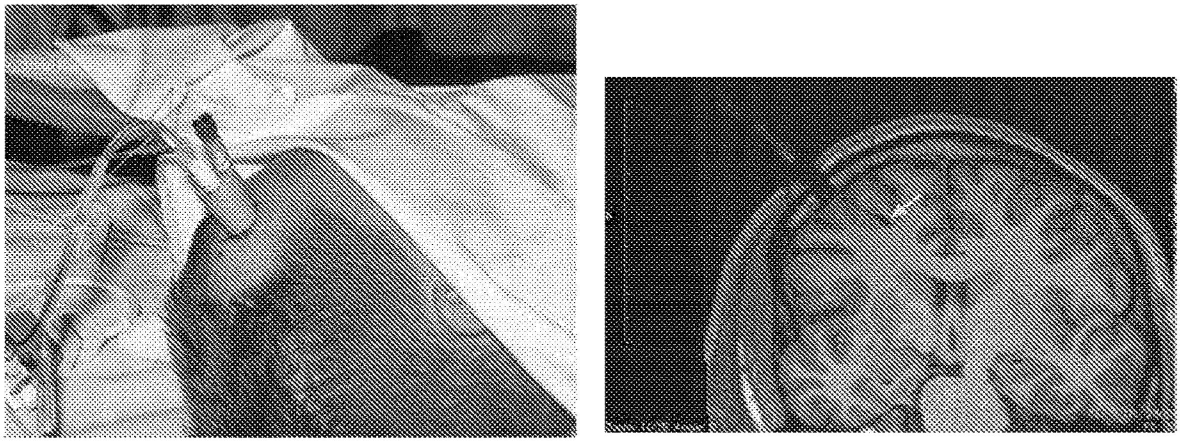
FIG. 2A is a photograph of a microdialysis probe inserted into a brain of a patient.
FIG. 2B is a magnetic resonance image showing a microdialysis probe inserted into a brain of a patient.

FIG. 2A is a photograph of a microdialysis probe inserted into a brain of a patient; and FIG. 2B is a magnetic resonance imaging (MRI) scan of a microdialysis probe inserted into a brain of a patient. Particularly, FIG. 2A shows the microdialysis probe together with an oxygen sensor for cerebral oximetry and a pressure sensor for intracranial pressure monitoring inserted into the brain of the patient. FIG. 2B depicts an MRI scan, using 3D MP-RAGE sequence, at 3 Tesla, showing the brain of a TBI patient with a microdialysis catheter (via a cranial access device) in position, the catheter tip indicated by an arrow (yellow). Scale bar (green) shows centimeter divisions.

Figure 3:
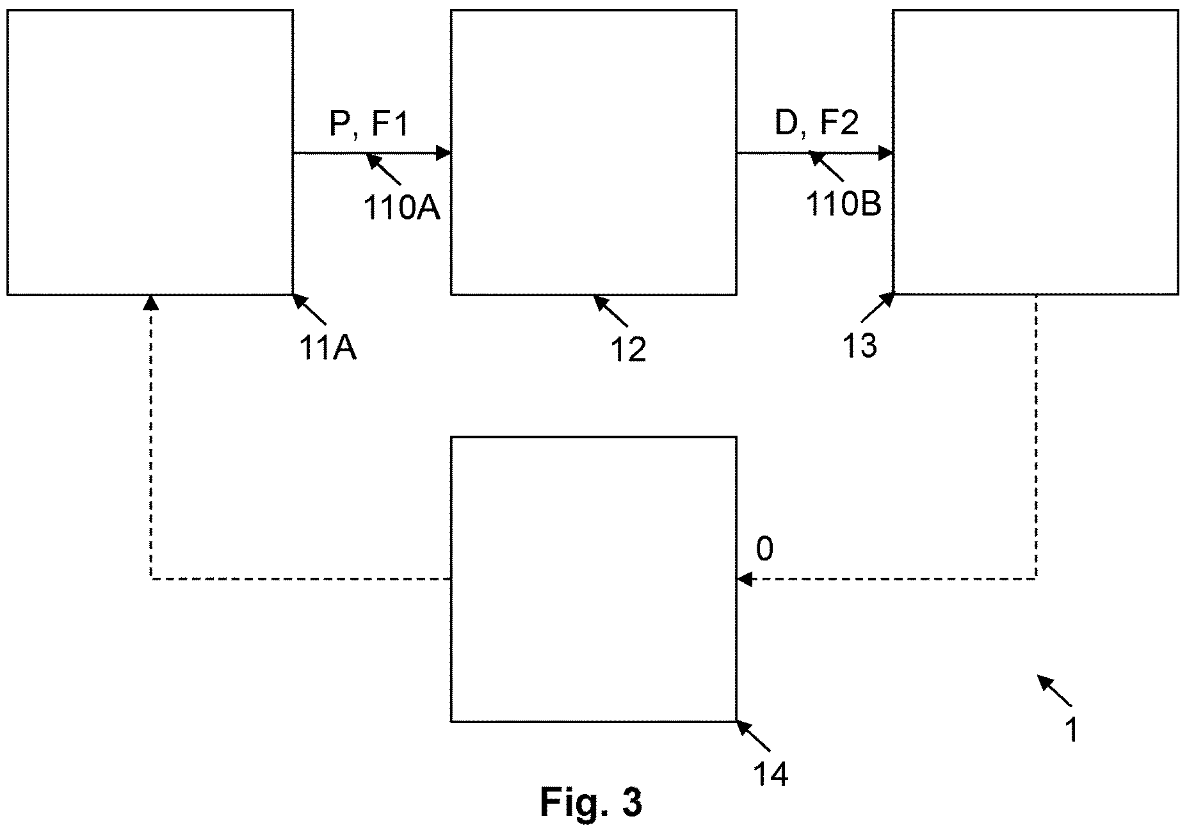
FIG. 3 schematically depicts a detector assembly according to an exemplary embodiment.

FIG. 3 schematically depicts a detector assembly 1 according to an exemplary embodiment.

The detector assembly 1 is for determining a ratio of lactate to pyruvate from dialysis, preferably microdialysis for example cerebral microdialysis. The detector assembly comprises: a first pump 11A of a set of pumps 11, a dialysis probe 12, preferably a microdialysis probe, having an inlet 121 (not shown) and an outlet 122 (not shown), a first tube 110A of a set of tubes 110 arranged to fluidically couple the first pump 11A to the inlet 121 of the dialysis probe 12, an infrared, IR, detector 13, a second tube 110B of the set of tubes 110 arranged to fluidically couple the outlet 122 of the dialysis probe 12 to the IR detector 13 and a controller 14; wherein the first pump 11A is arranged to pump a perfusate P at a first flow rate F1 of a set of flow rates to the dialysis probe 12, inserted into a fluid, for example a bodily fluid, and/or an organ of and/or for a patient, via the first tube 110A and to in turn pump, at least in part, a dialysate D at a second flow rate F2 of the set of flow rates from the dialysis probe 12 to the IR detector 13 via the second tube 1101B; wherein the IR detector 13 is arranged to detect respective absorbances due, at least in part, to lactate and pyruvate in the dialysate D; and wherein the controller 14 is arranged to determine the ratio of lactate to pyruvate in the dialysate based, at least in part, on the detected respective absorbances. Optionally, in this example, the IR detector 13 comprises a flow cell 131 arranged proximal to the outlet 122 of the dialysis probe 12, for example within 500 mm, preferably within 250 mm, more preferably within 100 mm of the outlet of the dialysis probe 12.

Figure 4:
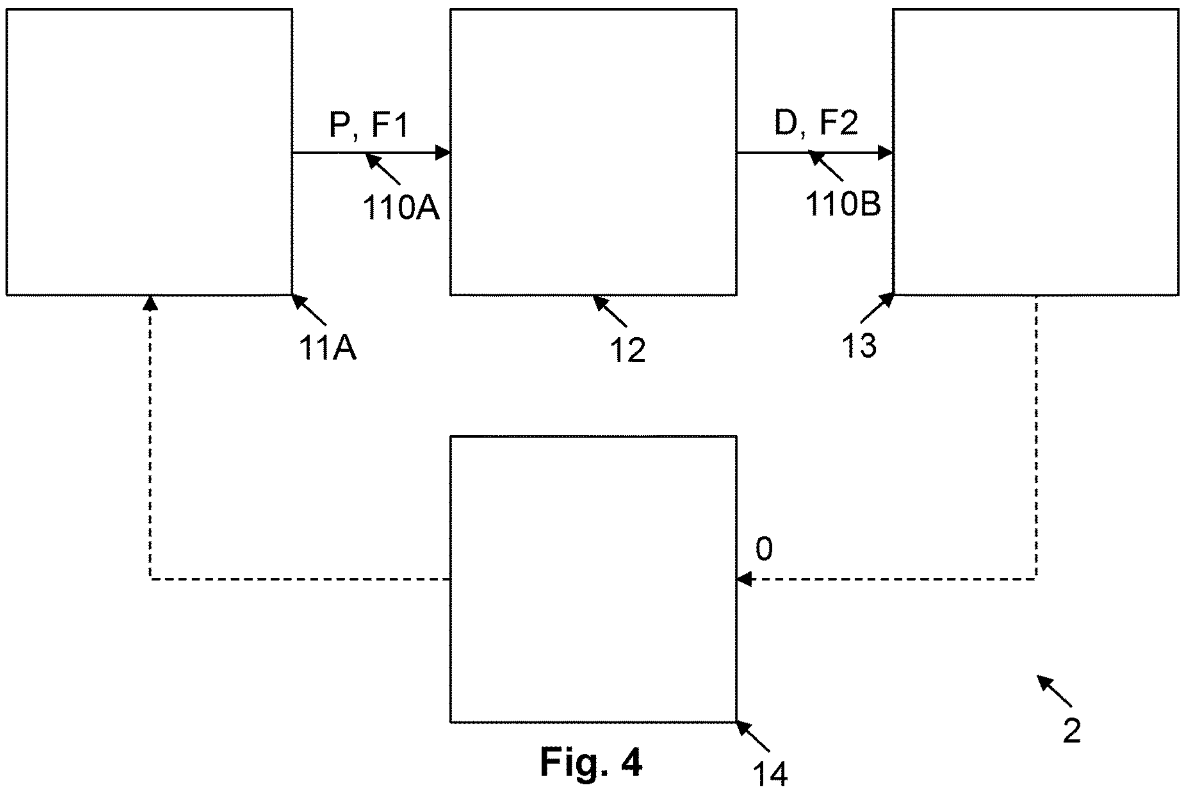
FIG. 4 schematically depicts a detector assembly according to an exemplary embodiment.

FIG. 4 schematically depicts a detector assembly 2 according to an exemplary embodiment. The detector assembly 2 is generally as described with respect to the detector assembly 1. In this example, the detector assembly 2 comprises a first valve 15A (not shown) of a set of valves 15 arranged to direct the dialysate D at the second flow rate F2 of the set of flow rates from the outlet of the dialysis probe 12 to the IR detector 13 via the second tube 110B and the set of pumps 11 comprises a second pump 11B (not shown) arranged to pump, at least in part, the dialysate D at the second flow rate F2 of the set of flow rates from the dialysis probe 12 to the IR detector 13 via the second tube 110B, wherein the second flow rate F2 is greater than the first flow rate F1. Optionally, in this example, the IR detector 13 comprises a flow cell 131 arranged proximal to the outlet 122 of the dialysis probe 12, for example within 500 mm, preferably within 250 mm, more preferably within 100 mm of the outlet of the dialysis probe 12. In other words, the flow cell 131 may be remote from the IR detector 13 (particularly, an absorbance sensor thereof), coupled thereto via optical fibers for example (i.e. via a first optical fiber to an IR source and via a second optical fiber to the absorbance sensor).

Figure 5:
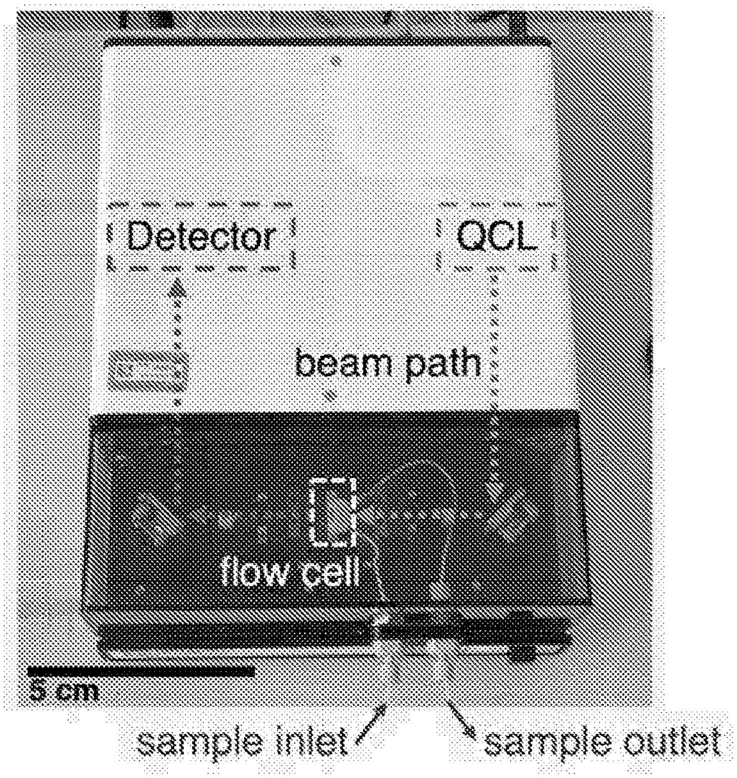
FIG. 5 is a photograph of an infrared (IR) detector for a detector assembly according to an exemplary embodiment.

FIG. 5 is a photograph of an infrared (IR) detector 13 for a detector assembly 1, 2 according to an exemplary embodiment. The IR detector 13 comprises an IR source, particularly a QCL, a flow cell and an absorbance sensor. An inlet of the flow cell is fluidically coupled to an end of the second tube and an outlet of the flow cell is fluidically coupled to an end of a third tube of the set of tubes, for collection of the dialysate D in a vial, for example, for subsequent analysis.

In more detail, measurements were acquired using a ChemDetect Analyzer (Daylight Solutions, Inc.), comprising a tunable QCL light source, a microfluidic flow-cell and a thermoelectrically-cooled InAsSb (indium arsenide antimonide) detector. The QCL is broadly tunable within the MIR fingerprint region between 982 and 1258 $cm^{-1}$, and sweeps are made with 0.2 $cm^{-1}$ steps and averaged to 2 $cm^{-1}$ resolution. A single sweep is taken in approximately 1 second, but several sweeps can be averaged for an increased SNR in the final spectrum. A cooling system (UC160-190, Solid State Cooling Systems, USA) was used in conjunction with ChemDetect Analyzer to ensure temperature stability during measurements by recirculating a mixture of chilled water and liquid coolant (702 Liquid Coolant, Koolance, South Korea) in the bottom plate of the instrument via two rear inlet/outlet connectors. The flow-cell of ChemDetect is the core of the sample interface. It has a small channel volume of 1 μL and a path-length, which can be adjusted through the selection of different polytetrafluoroethylene (PTFE)-gasket thicknesses, between 25 and 200 μm. The gasket is sandwiched between the top and bottom pieces, which are assembled using alignment pins and attachment screws. The flow-cell incorporates two diamond windows through which the laser beam transmits to interact with the flowing sample. Inlet and outlet tubing are connected to the flow-cell using appropriate connectors (M660 Nut and super flangeless M650 Ferrule for 1.6 mm OD tubing, Cole-Parmer Ltd., UK). The flow-cell is mounted into the sample compartment using alignment pins and attachment screws, and two coned 10-32 ports are used to connect external sample-carrying tubing to the ChemDetect, allowing the sample to enter/exit the inlet/outlet tubing of the flow-cell. The cell can easily be disassembled for cleaning and/or gasket changing if different optical path-lengths are required.

Figure 6:
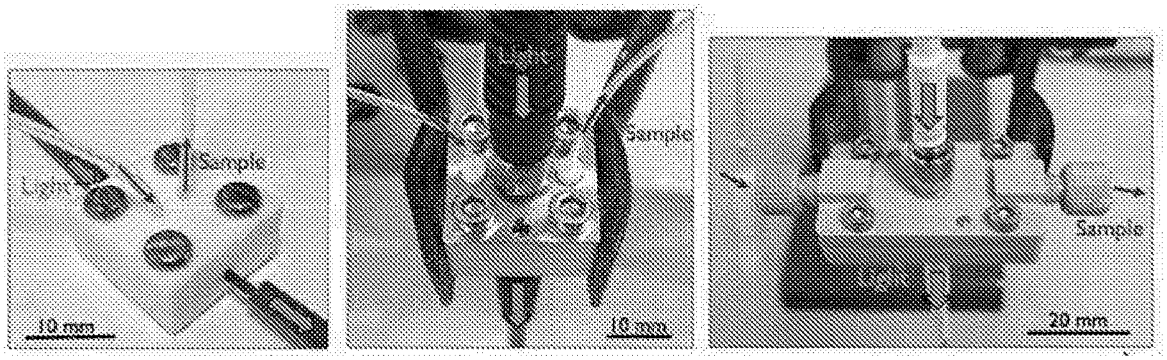
FIG. 6A is a photograph of a flow cell for an infrared (IR) detector for a detector assembly according to an exemplary embodiment.
FIG. 6B is a photograph of a flow cell for an infrared (IR) detector for a detector assembly according to an exemplary embodiment.
FIG. 6C is a photograph of a flow cell for an infrared (IR) detector for a detector assembly according to an exemplary embodiment.

FIG. 6A is a photograph of a flow cell for an infrared (IR) detector 13 for a detector assembly 1, 2 according to an exemplary embodiment; FIG. 6B is a photograph of a flow cell for an infrared (IR) detector 13 for a detector assembly 1, 2 according to an exemplary embodiment; and FIG. 6C is a photograph of a flow cell for an infrared (IR) detector 13 for a detector assembly 1, 2 according to an exemplary embodiment. Particularly, these flow cells are configured to be remote from the IR detector 13 (particularly, an absorbance sensor thereof), coupled thereto via optical fibers for example (i.e. via a first optical fiber to an IR source and via a second optical fiber to the absorbance sensor).

Figure 7:
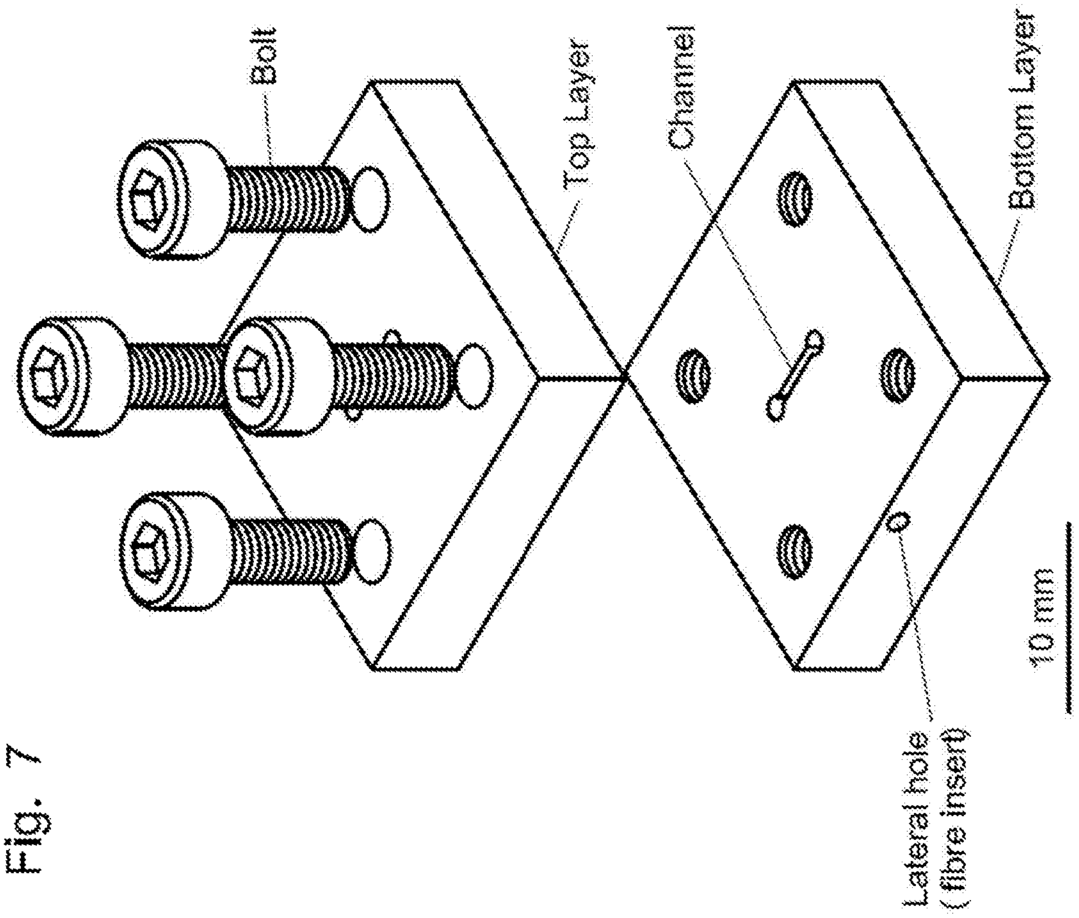
FIG. 7 is an exploded perspective CAD drawing of the flow cell of FIG. 6A.

FIG. 7 is an exploded perspective CAD drawing of the flow cell of FIG. 6A, in more detail.

In more detail, FIG. 7 is an exploded perspective CAD drawing of the flow cell of FIG. 6A, showing the different components comprising the latter. This flow cell consists of two layers of polytetrafluoroethylene (PTFE), which are stacked and tightly assembled using four bolts. The bottom layer provides a channel for the sample fluid to flow through and also holds two lateral and aligned holes to place a fiber optic cable on either side of the channel. The analytes within the flowing sample are detected via transmission of light through the channel, from one fiber to the other. The top layer comprises of two holes at the same distance apart as the channel length, which serve as the channel inlet and outlet, where the sample-carrying tubing is inserted. The channel volume of this flow-cell is 2.5 μL.

Figure 8:
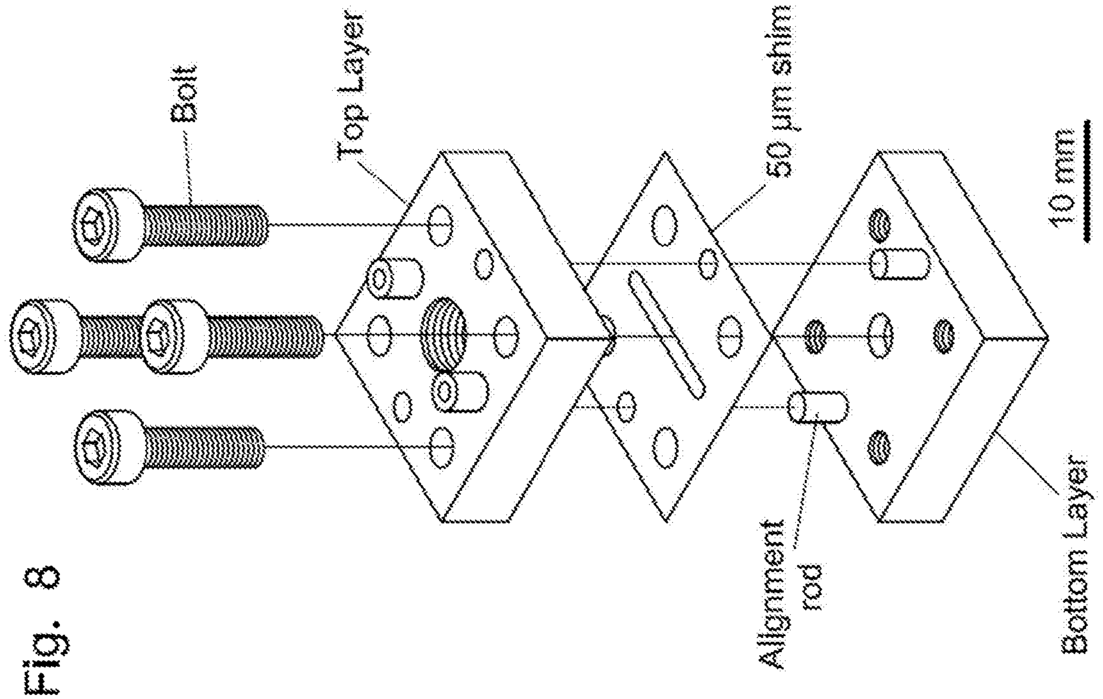
FIG. 8 is an exploded perspective CAD drawing of the flow cell of FIG. 6B.

FIG. 8 is an exploded perspective CAD drawing of the flow cell of FIG. 6B. In more detail, FIG. 8 is an exploded perspective CAD drawing of the flow cell of FIG. 6B. This flow cell comprises of three stainless-steel layers which are stacked and fastened together using four bolts. All three layers provide four threaded holes to accept the bolts and two smaller holes for inserting stainless-steel alignment rods which are used to ensure careful alignment of the layers during assembly. In this apparatus, the top and bottom layers provide a central threaded hole for connecting two optical fibers. In order to prevent leakage, a rubber O-ring of 2 mm inner diameter is initially placed in the connector insert before connecting the fibers. The top layer provides an additional two holes, which are used as the channel inlet and outlet, where hollow PTFE cylinders are inserted to provide a tight fit for the sample-carrying tubing. The middle layer consists of a 50 μm stainless-steel shim and provides the fluidic channel. The fiber inserted in the top layer is used as the light source while the fiber inserted in the bottom layer is used as the light detector. The channel volume of this flow-cell is 1.6 μL.

Figure 9A:
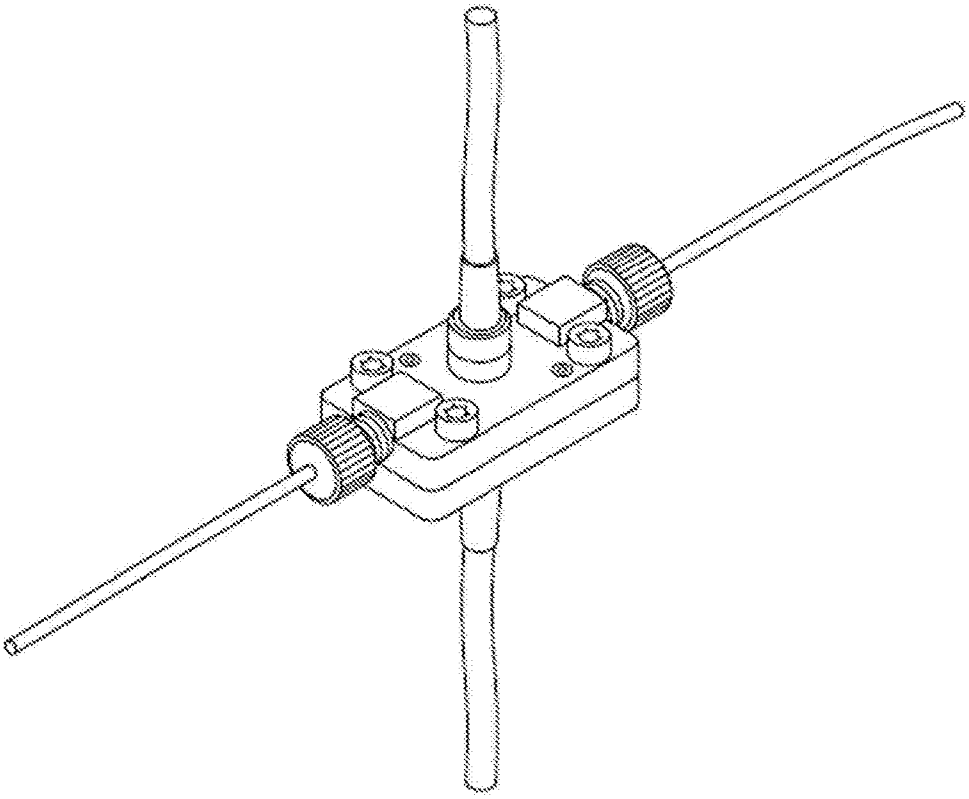
FIG. 9A is a perspective CAD drawing of the flow cell of FIG. 6C.
Figure 9B:
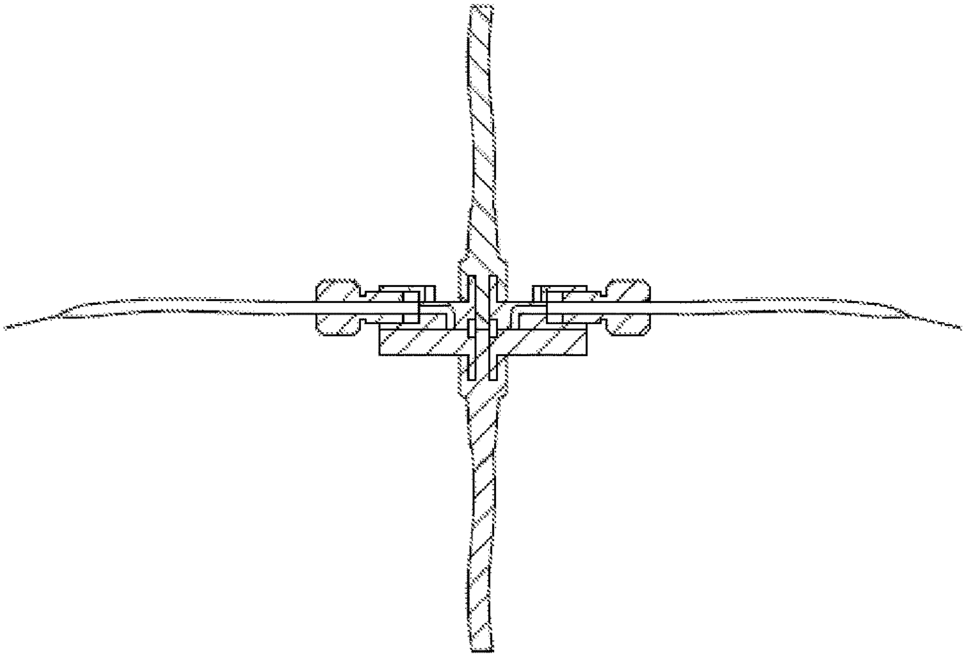
FIG. 9B is a cross-sectional view of the flow cell of FIG. 9A.

FIG. 9A is a perspective CAD drawing of the flow cell of FIG. 6C; and FIG. 9B is a cross-sectional view of the flow cell of FIG. 9A.

In more detail, FIG. 9A is a perspective CAD drawing of the flow cell of FIG. 6C; FIG. 9B is a cross-sectional view of the flow cell of FIG. 9A. This flow cell comprises of two PEEK layers (top and bottom) and one PTFE gasket, which is sandwiched between the two layers using four bolts. The top layer holds two lateral threaded holes to insert a standard tubbing connector on either side of the flow-cell. In this apparatus, the top and bottom layers provide a central threaded hole for connecting optical fibers, one which is used as the light source and the other which is used as the light detector. The channel volume of this flow-cell is 0.65 μL.

Figure 10:
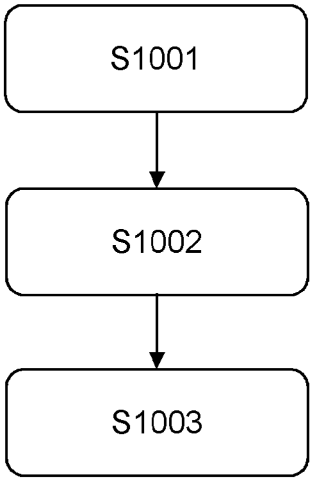
FIG. 10 schematically depicts a method according to an exemplary embodiment.

FIG. 10 schematically depicts a method according to an exemplary embodiment.

The method is of determining a ratio of lactate to pyruvate from dialysis, preferably microdialysis for example cerebral microdialysis.

At S1001, a perfusate is pumped, by a first pump of a set of pumps, at a first flow rate of a set of flow rates to a dialysis probe, preferably a microdialysis probe, inserted into a fluid, for example a bodily fluid, and/or an organ of and/or for a patient, via a first tube of a set of tubes and in turn pumping, at least in part, a dialysate at a second flow rate of the set of flow rates from the dialysis probe to an infrared, IR, detector via a second tube of the set of tubes.

At S1002, respective absorbances due, at least in part, to lactate and pyruvate in the dialysate are detected, by the IR detector.

At S1003, the ratio of lactate to pyruvate in the dialysate is determined, by a controller, based, at least in part, on the detected respective absorbances.

Figure 11:
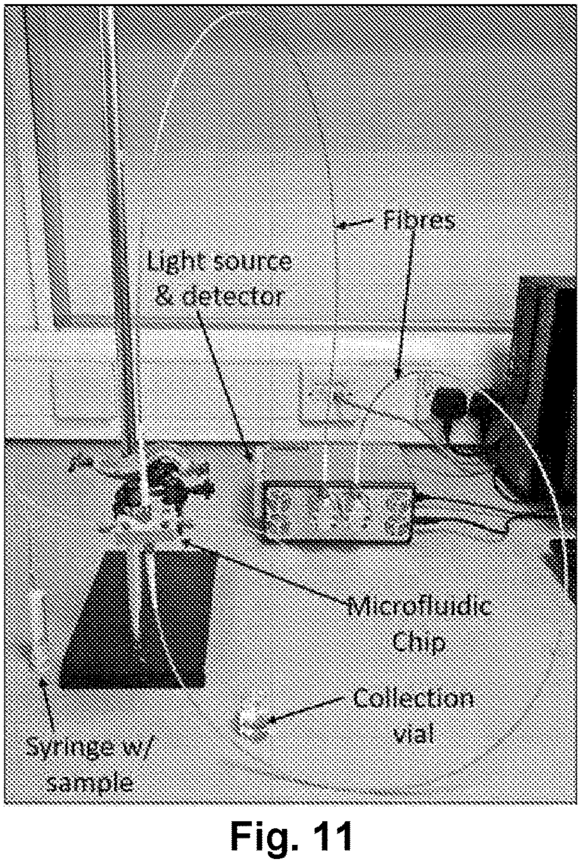
FIG. 11 is a photograph of a detector assembly according to an exemplary embodiment, in use.

FIG. 11 is a photograph of a detector assembly 3 according to an exemplary embodiment, in use, particularly for in vitro analysis. In this example, the IR detector 13 comprises the flow cell 131C, as described above.

Figure 12:
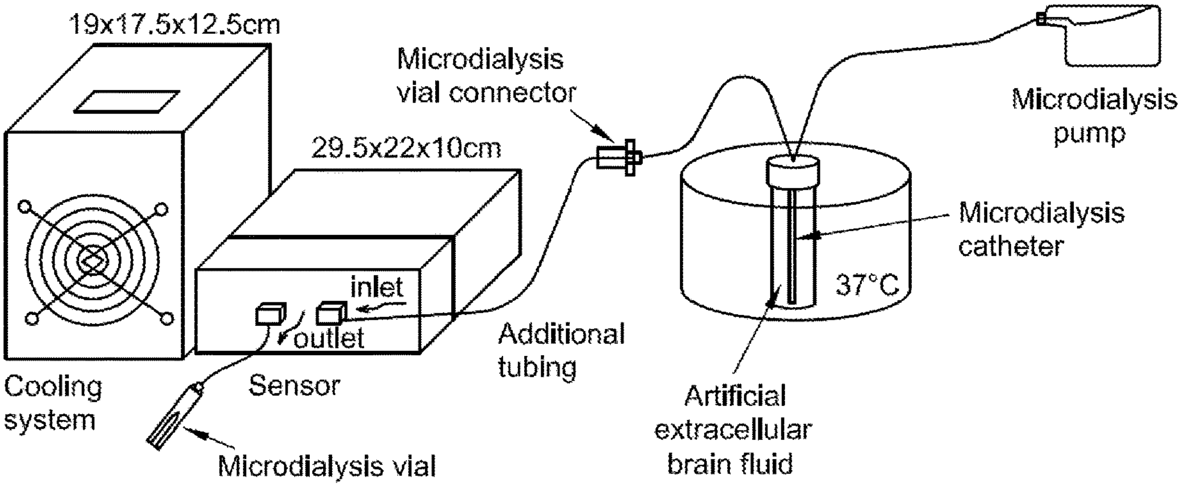
FIG. 12 schematically depicts a detector assembly according to an exemplary embodiment, in use.

FIG. 12 schematically depicts a detector assembly 4 according to an exemplary embodiment, in use, particularly for in vitro analysis or ex vivo analysis. In this example, the dialysis probe 12 is inserted into synthetic extracellular brain fluid at 37° C. (i.e. human body temperature). In this example, the IR detector 13 comprises the flow cell 131C, as described above.

In more detail, FIG. 12 shows the laboratory setup created to mimic clinical monitoring using the ChemDetect Analyzer in order to assess its performance for carrying out continuous microdialysate monitoring in conjunction with the clinically used standard microdialysis catheter and pump. Here, an external standard (ES) solution (i.e. artificial extracellular brain fluid) was prepared using perfusion fluid with 5 μg/mL human serum albumin (HAS, 126658, ≥95%, Sigma Aldrich) and 0.05% w/v sodium azide (S2002, ≥99.5%, Sigma Aldrich) to make a total solution of approximately 15-20 mL, which was added to a Corning™ Falcon 50 mL conical centrifuge tube. Depending on the nature of the experiment, a desired amount of any or all metabolites (glucose, lactate and pyruvate) at physiological concentrations can be added at the beginning or throughout the experiment in order to track changes. A small magnetic stirrer was added to the ES in the Falcon tube, after which a 20 $cm^2$ of cling film was folded into a 4-layer square and used to cover the top of the open tube, secured by a rubber band. The cling film was then gently pierced and a triple lumen cranial access device held in place in the Falcon tube within a glycerol (G9012, ≥99.5%, Sigma-Aldrich) bath on a thermostatically-controlled hotplate-stirrer (97042-754, VWR, USA) at 37° C., with the stirrer speed set to 60 rpm. A standard MD catheter (8010320, M Dialysis 71 High Cut-Off Brain Microdialysis Catheter, M Dialysis AB, Sweden), with 100 kDa MWCO and a 10 mm membrane length was placed into the ES through the triple lumen cranial access device.

Figure 13:
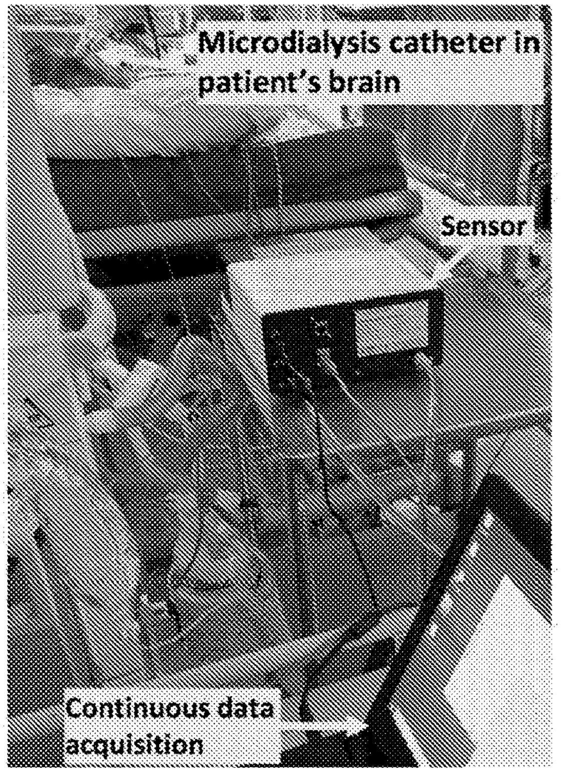
FIG. 13 is a photograph of a detector assembly according to an exemplary embodiment, in use.

FIG. 13 is a photograph of a detector assembly 5 according to an exemplary embodiment, in use, particularly for in vivo analysis.

Figure 14:
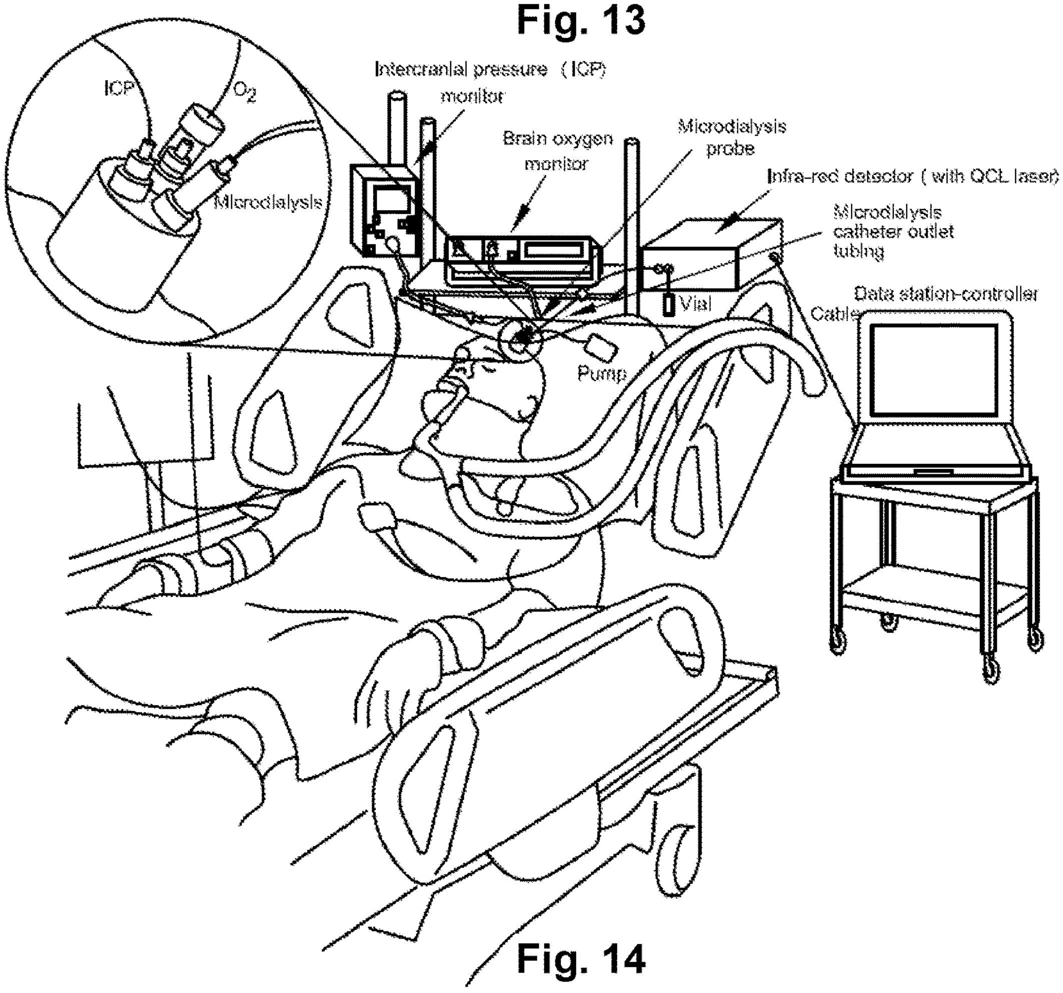
FIG. 14 schematically depicts a detector assembly according to an exemplary embodiment, in use.

FIG. 14 schematically depicts a detector assembly 6 according to an exemplary embodiment, in use, particularly for in vivo analysis. In this example, the flow cell is arranged proximal the outlet of the microdialysis probe.

Figure 15A:
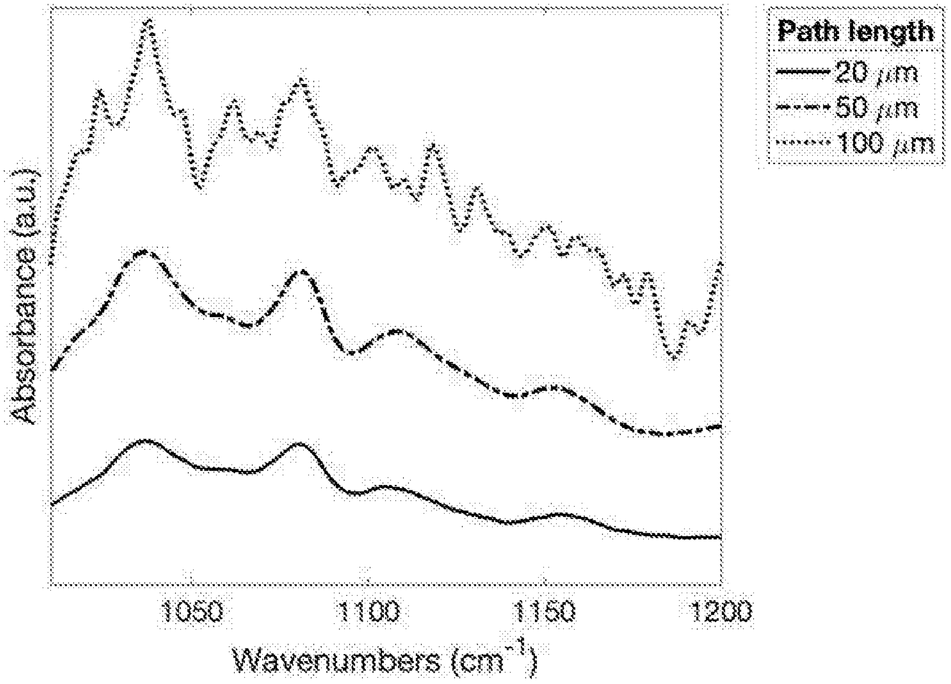
FIG. 15A is a graph of absorbance as a function of wavenumber for 24 mM glucose for path lengths of 20 μm, 50 μm and 100 μm.
Figure 15B:
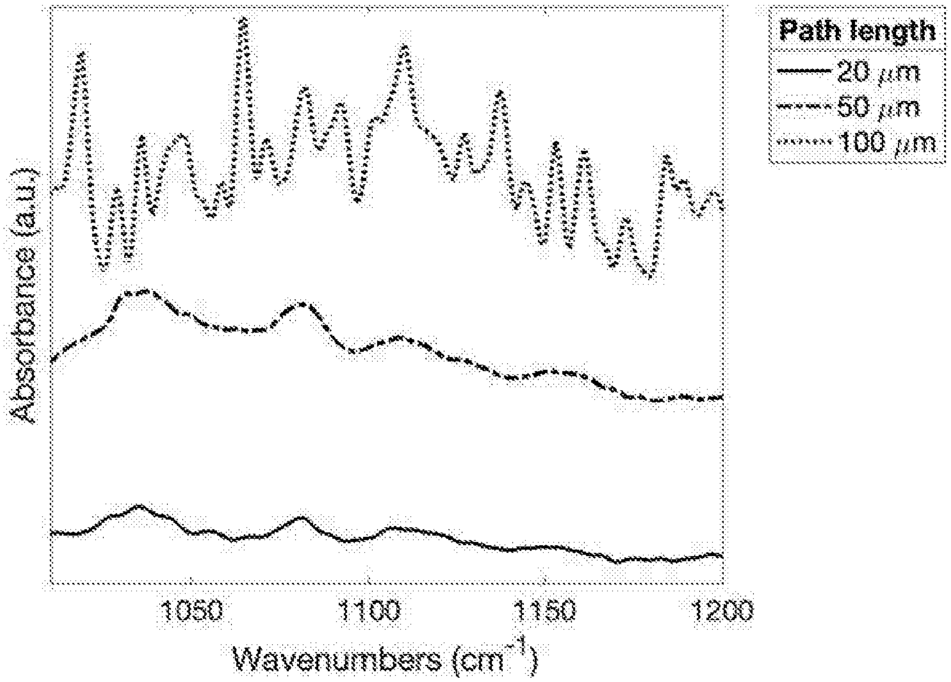
FIG. 15B is a graph of absorbance as a function of wavenumber for 6 mM glucose for path lengths of 20 μm, 50 μm and 100 μm.
Figure 15C:
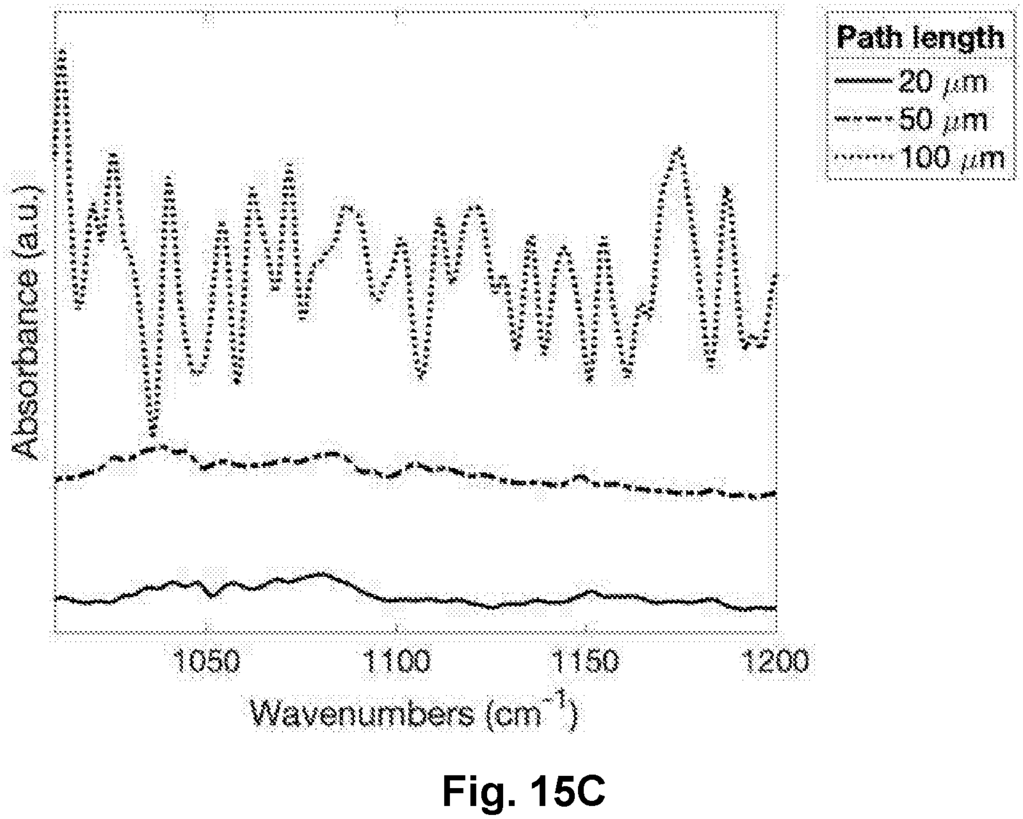
FIG. 15C is a graph of absorbance as a function of wavenumber for 1.5 mM glucose for path lengths of 20 μm, 50 μm and 100 μm.

FIG. 15A is a graph of absorbance as a function of wavenumber for 24 mM glucose for path lengths of 20 μm, 50 μm and 100 μm; FIG. 15B is a graph of absorbance as a function of wavenumber for 6 mM glucose for path lengths of 20 μm, 50 μm and 100 μm; and FIG. 15C is a graph of absorbance as a function of wavenumber for 1.5 mM glucose for path lengths of 20 μm, 50 μm and 100 μm. In more detail, the absorbances were measured using the detector assembly 3, generally as described with respect to FIG. 11, measured on standard FTIR with transmission cell accessory (Pearl, Specac) using different cell path-lengths: 20, 50 and 100 μm. The results obtained with a path-length of 50 μm showed higher S-N-R. Note: For clarity, each spectrum has been plotted with a vertical offset with respect to the other spectra.

Figure 16A:
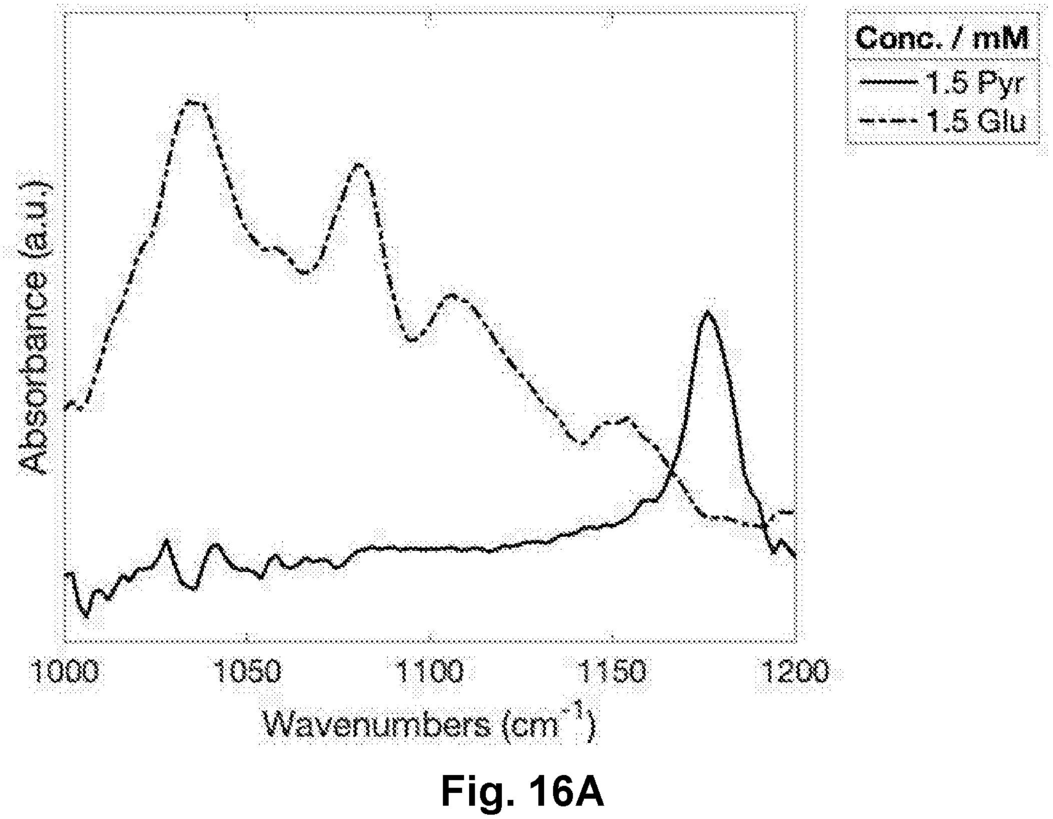
FIG. 16A is a graph of absorbance as a function of wavenumber for 1.5 mM glucose and 1.5 mM pyruvate for a path length of 127 μm.
Figure 16B:
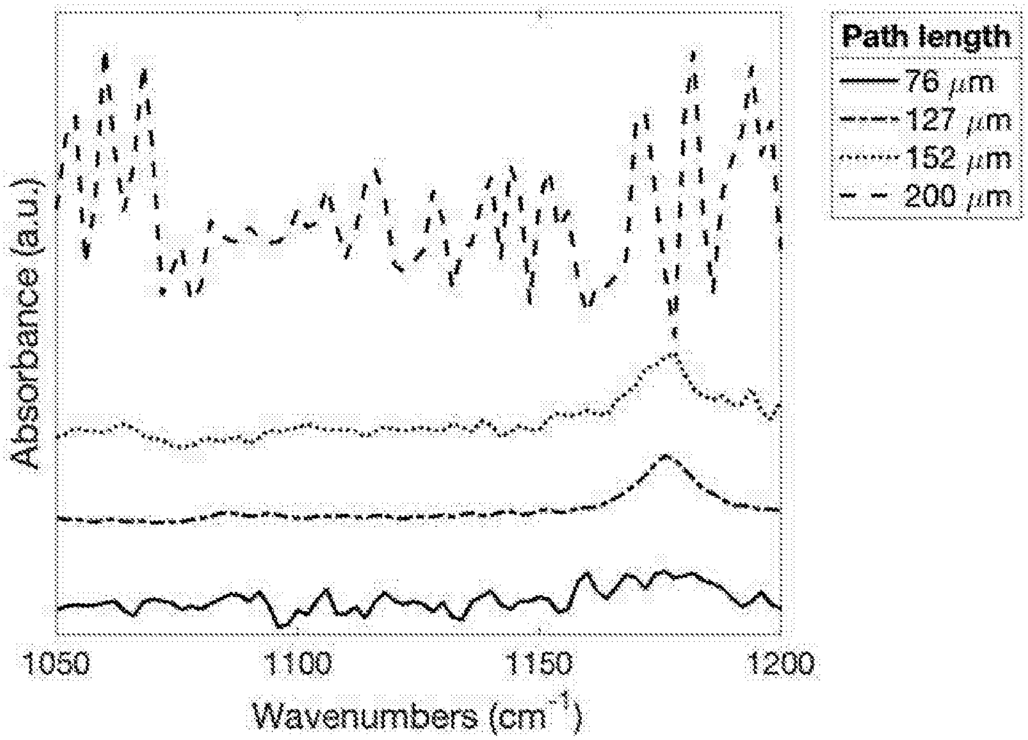
FIG. 16B is a graph of absorbance as a function of wavenumber for 1 mM pyruvate for path lengths of 76 μm, 127 μm, 150 μm and 200 μm.

FIG. 16A is a graph of absorbance as a function of wavenumber for 1.5 mM glucose and 1.5 mM pyruvate for a path length of 127 μm; and FIG. 16B is a graph of absorbance as a function of wavenumber for 1 mM pyruvate for path lengths of 76 μm, 127 μm, 150 μm and 200 μm. In more detail, the absorbances were measured using the detector assembly 3, generally as described with respect to FIG.

11, measured on a ChemDetect IR detector. The results obtained with a path-length of 127 μm showed higher S-N-R. Note: For clarity, each spectrum has been plotted with a vertical offset with respect to the other spectra.

Figure 17A:
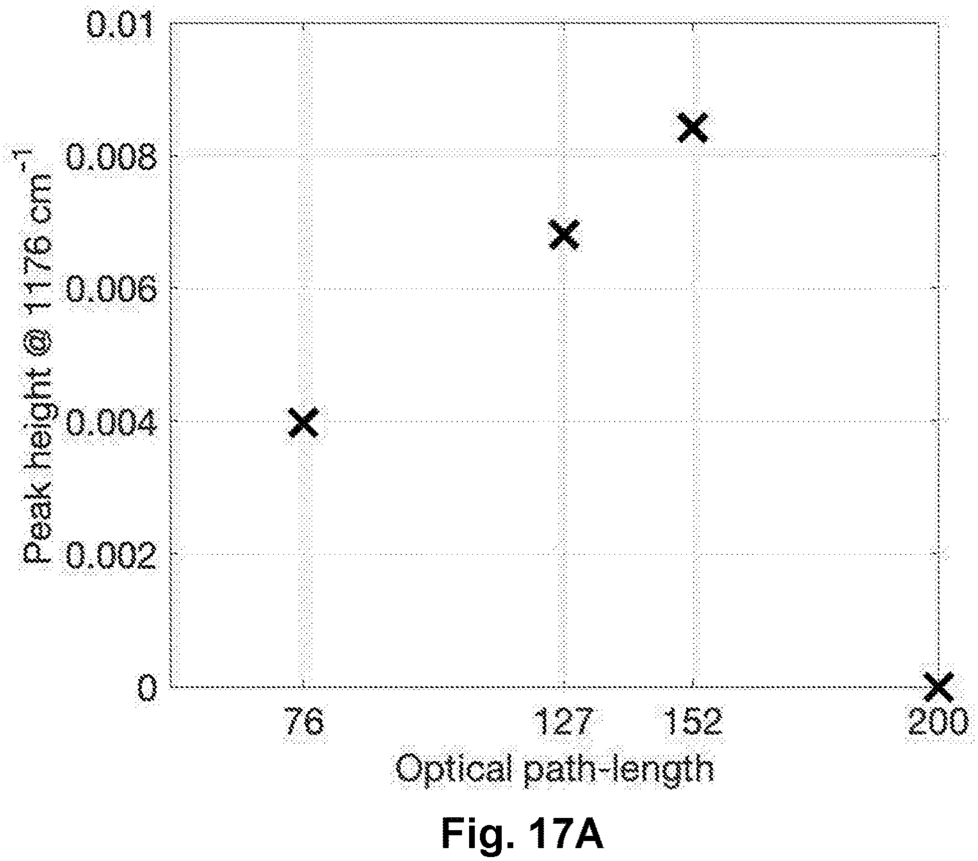
FIG. 17A is a graph of peak height for pyruvate (wavenumber=1176 $cm^{-1}$) as a function of path length for path lengths of 76 μm, 127 μm, 150 μm and 200 μm.
Figure 17B:
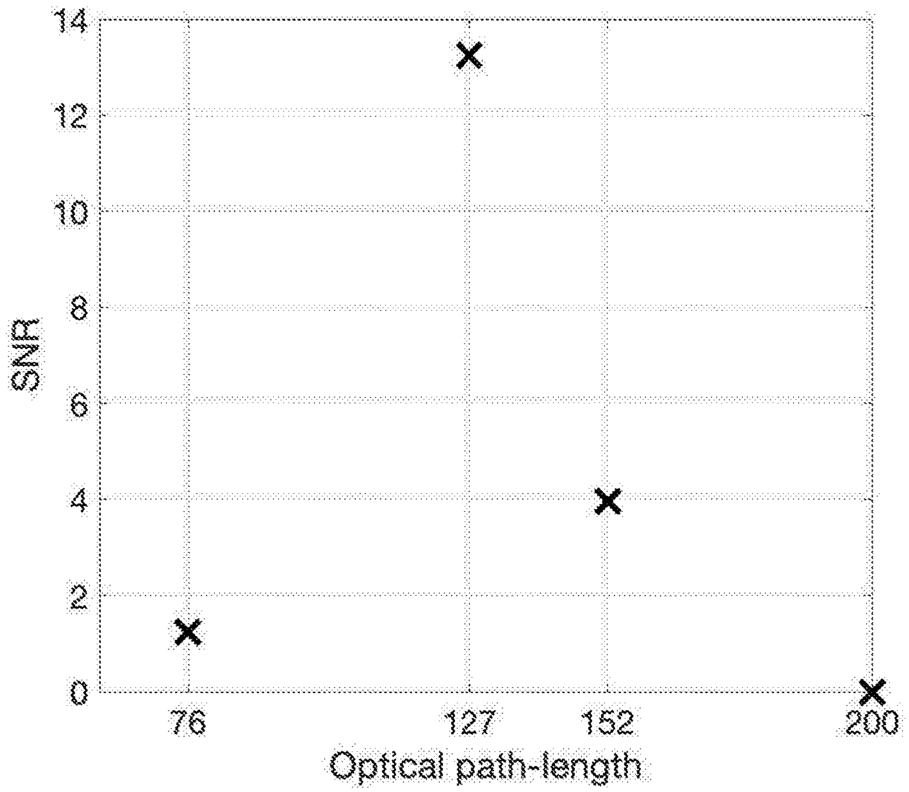
FIG. 17B is a graph of signal-to-noise (SNR) for pyruvate (wavenumber=1176 $cm^{-1}$) as a function of path length for path lengths of 76 μm, 127 μm, 150 μm and 200 μm.

FIG. 17A is a graph of peak height for pyruvate (wavenumber=1176 $cm^{-1}$) as a function of path length for path lengths of 76 μm, 127 μm, 150 μm and 200 μm; and FIG. 17B is a graph of signal-to-noise (SNR) for pyruvate (wavenumber=1176 $cm^{-1}$) as a function of path length for path lengths of 76 μm, 127 μm, 150 μm and 200 μm. For this analysis, a path length of 127 μm is preferred—at larger path lengths, the SNR is degraded.

Figure 18A:
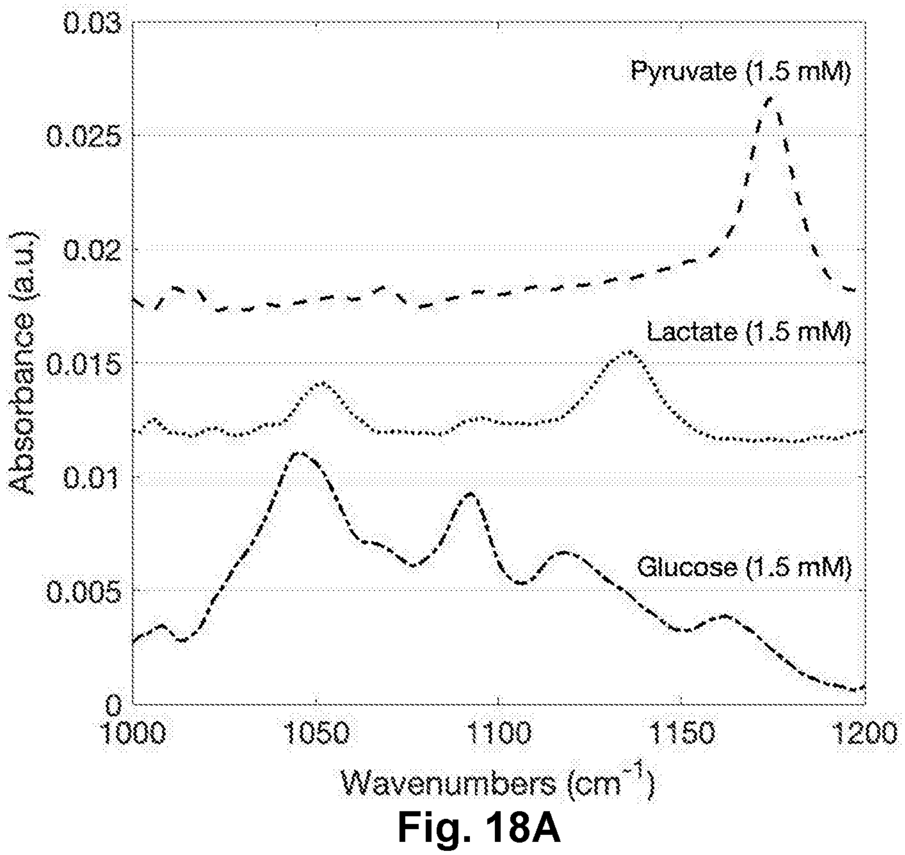
FIG. 18A is a graph of absorbance as a function of wavenumber for pyruvate (1.5 mM), lactate (1.5 mM) and glucose (1.5 mM), for a path length of 127 μm.
Figure 18B:
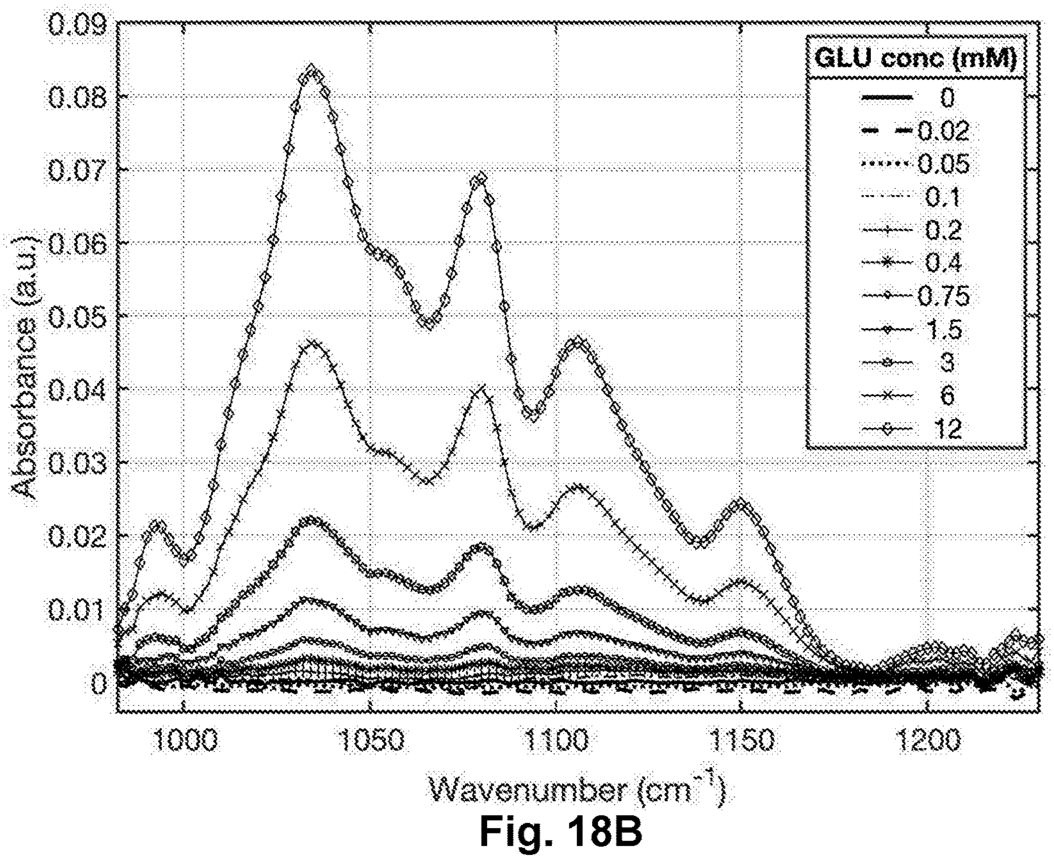
FIG. 18B is a graph of absorbance as a function of wavenumber for glucose (wavenumbers=1036 $cm^{-1}$, 1080 $cm^{-1}$, 1108 $cm^{-1}$, 1152 $cm^{-1}$) having a concentration in a range from 0 to 12 mM for a path length of 127 μm.
Figure 18C:
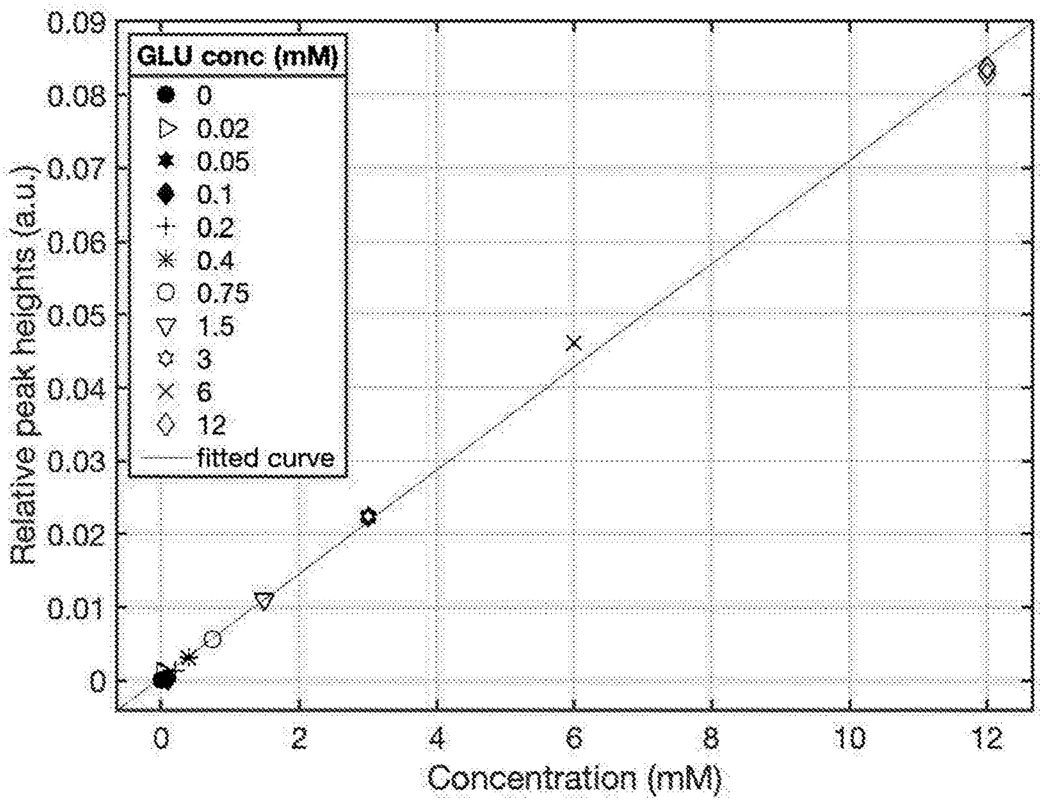
FIG. 18C is a graph of relative peak height as a function of concentration for glucose (wavenumber=1036 $cm^{-1}$) having a concentration in a range from 0 to 12 mM for a path length of 127 μm.

FIG. 18A is a graph of absorbance as a function of wavenumber for pyruvate (1.5 mM), lactate (1.5 mM) and glucose (1.5 mM), for a path length of 127 μm; FIG. 18B is a graph of absorbance as a function of wavenumber for glucose (wavenumbers=1036 $cm^{-1}$, 1080 $cm^{-1}$, 1108 $cm^{-1}$, 1152 $cm^{-1}$) having a concentration in a range from 0 to 12 mM for a path length of 127 μm; and FIG. 18C is a graph of relative peak height as a function of concentration for glucose (wavenumber=1036 $cm^{-1}$) having a concentration in a range from 0 to 12 mM for a path length of 127 μm. The calibration curve of FIG. 18C is linear.

Figure 19A:
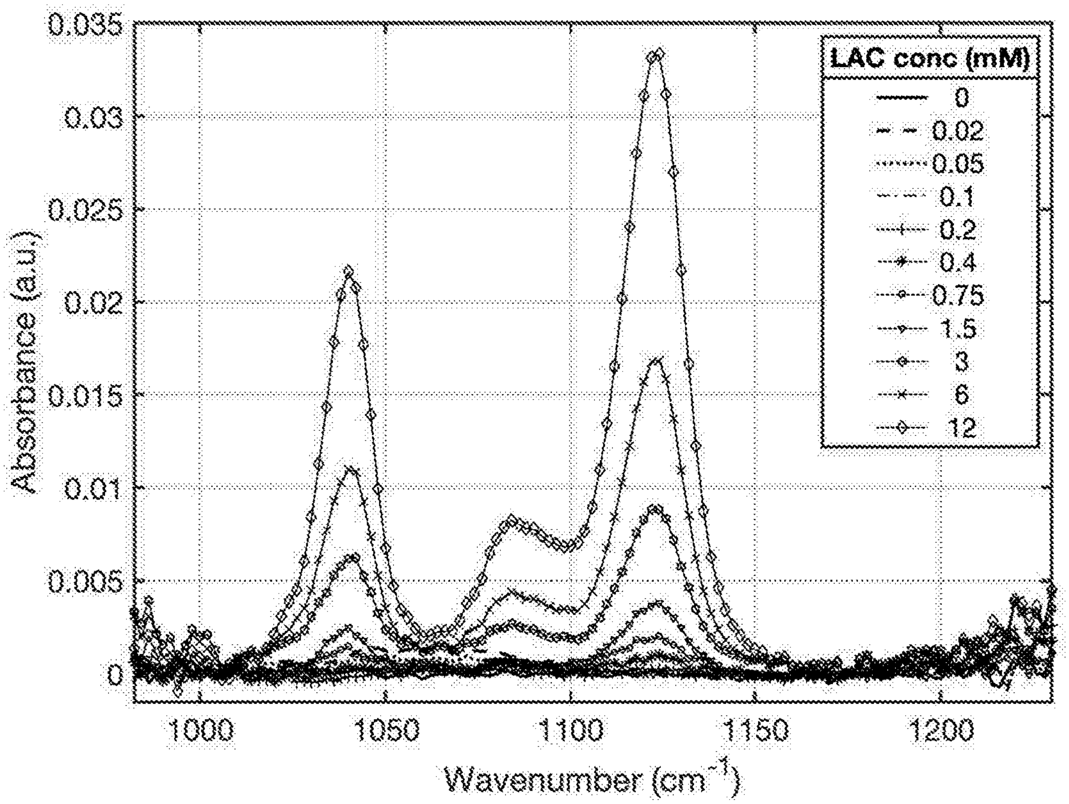
FIG. 19A is a graph of absorbance as a function of wavenumber for lactate (wavenumbers=1042 $cm^{-1}$, 1124 $cm^{-1}$) having a concentration in a range from 0 to 12 mM for a path length of 127 μm.
Figure 19B:
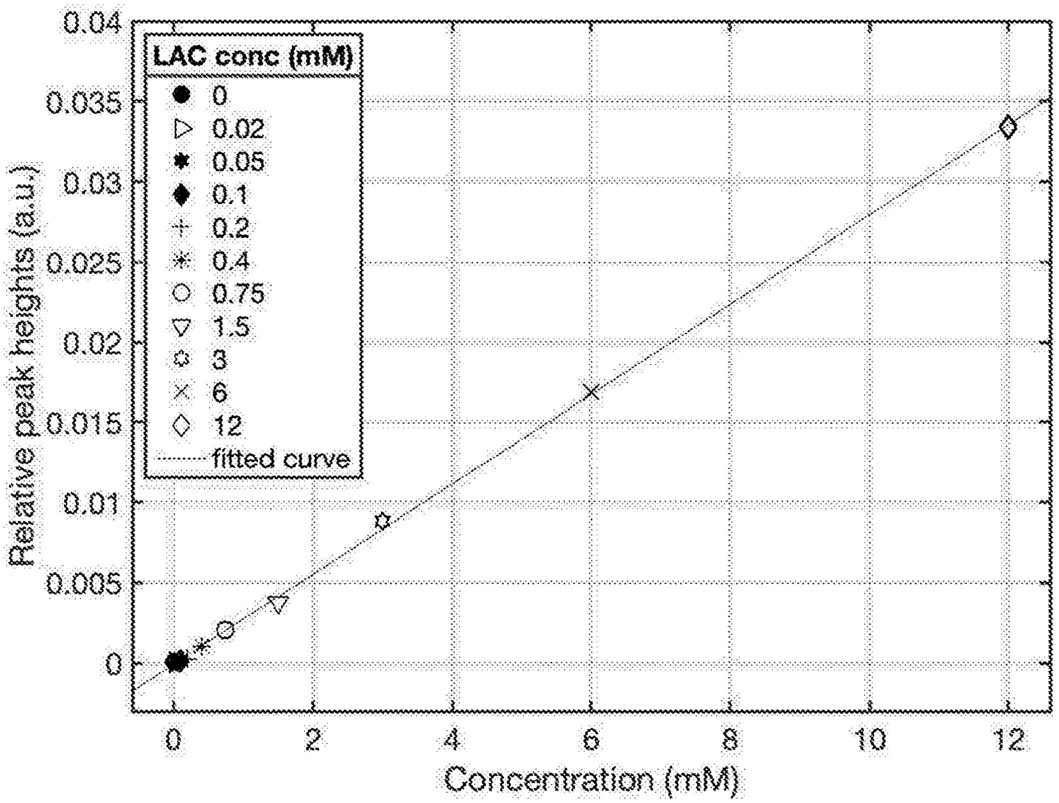
FIG. 19B is a graph of relative peak height as a function of concentration for lactate (wavenumber 1124 $cm^{-1}$) having a concentration in a range from 0 to 12 mM for a path length of 127 μm.

FIG. 19A is a graph of absorbance as a function of wavenumber for lactate (wavenumbers=1042 $cm^{-1}$, 1124 $cm^{-1}$) having a concentration in a range from 0 to 12 mM for a path length of 127 μm; and FIG. 19B is a graph of relative peak height as a function of concentration for lactate (wavenumber 1124 $cm^{-1}$) having a concentration in a range from 0 to 12 mM for a path length of 127 μm. The calibration curve of FIG. 19B is linear.

Figure 20A:
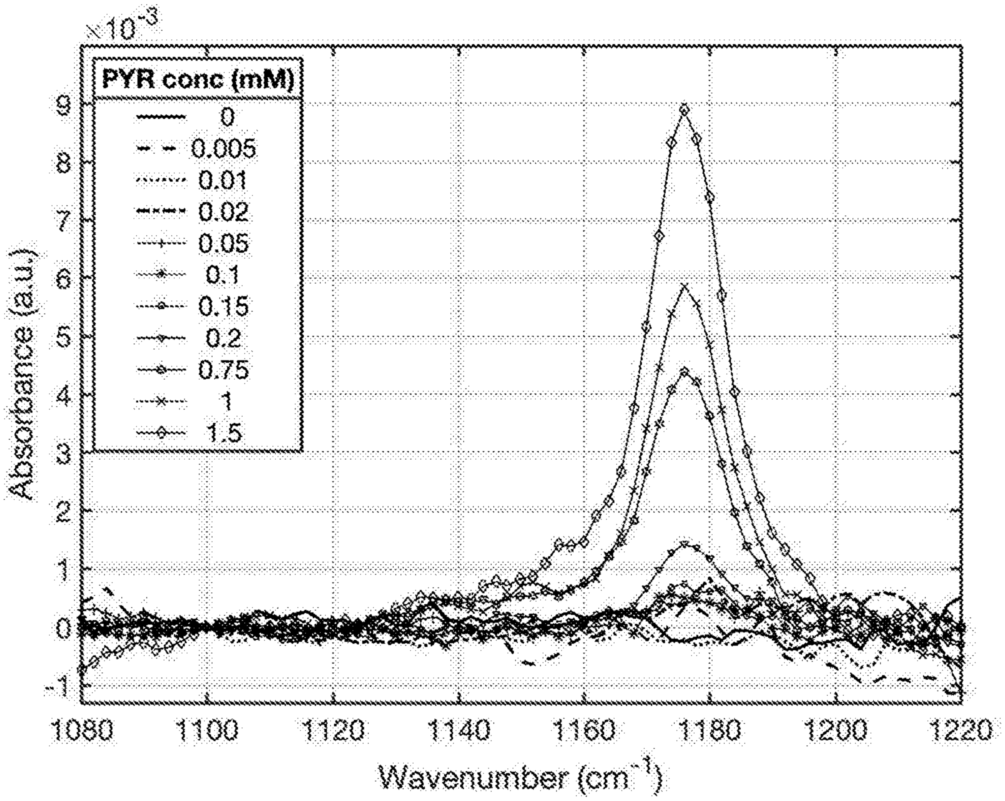
FIG. 20A is a graph of absorbance as a function of wavenumber for pyruvate (wavenumber=1176 $cm^{-1}$) having a concentration in a range from 0 to 1.5 mM for a path length of 127 μm.
Figure 20B:
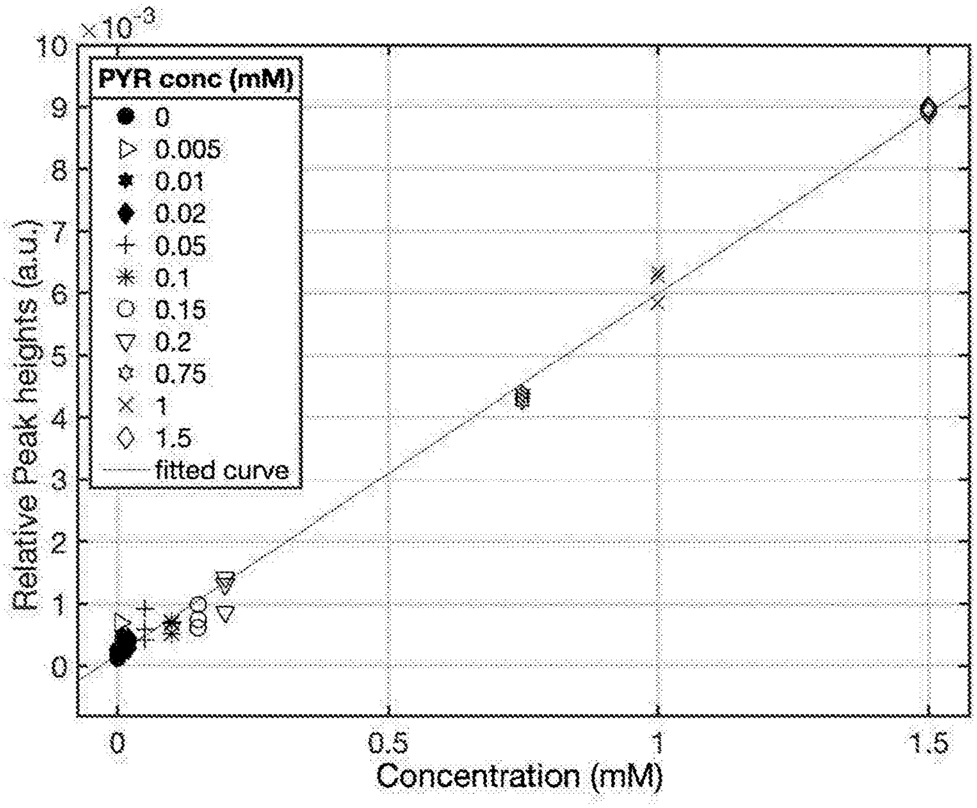
FIG. 20B is a graph of relative peak height as a function of concentration for pyruvate (wavenumber=1176 $cm^{-1}$) having a concentration in a range from 0 to 1.5 mM for a path length of 127 μm.

FIG. 20A is a graph of absorbance as a function of wavenumber for pyruvate (wavenumber=1176 $cm^{-1}$) having a concentration in a range from 0 to 1.5 mM for a path length of approximately 127 μm; and FIG. 20B is a graph of relative peak height as a function of concentration for pyruvate (wavenumber=1176 $cm^{-1}$) having a concentration in a range from 0 to 1.5 mM for a path length of approximately 127 μm. The calibration curve of FIG. 20B is linear.

Figure 21:
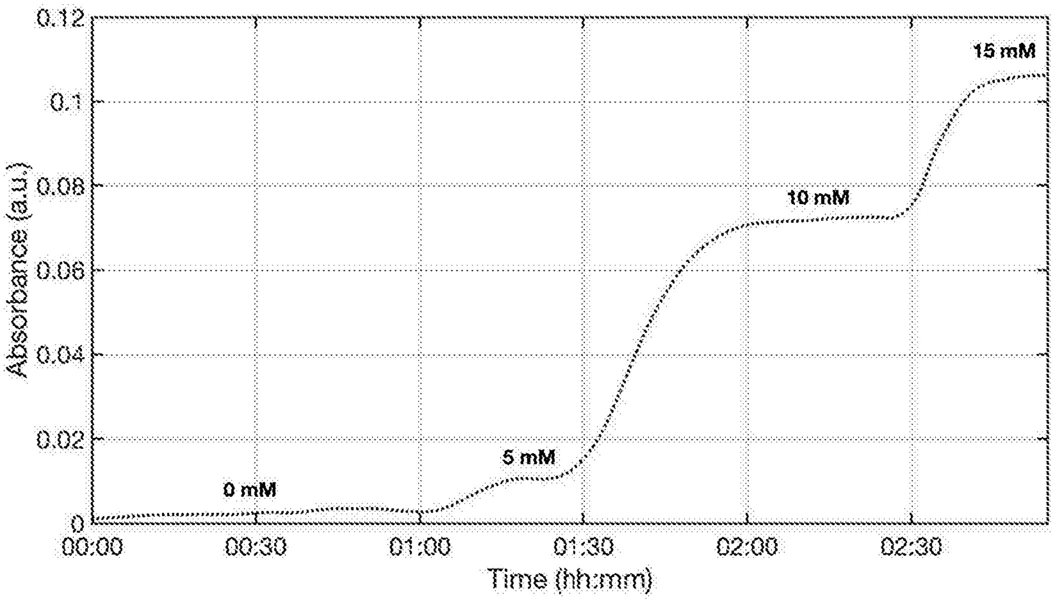
FIG. 21 is a graph of absorbance as a function of time for glucose (wavenumbers=1036 $cm^{-1}$) at stepped increasing concentrations in a range from 0 to 15 mM at a constant flow rate of 0.3 μL $min^{-1}$ for a path length of 127 μm.

FIG. 21 is a graph of IR absorbance as a function of time for glucose (wavenumber=1036 $cm^{-1}$) in an in-vitro bench test at stepped increasing glucose concentrations in a range from 0 to 15 mM at a constant flow rate of 0.3 μL $min^{-1}$ for a path length of approximately 127 μm. Generally, the absorbance increases linearly with concentration and is relatively constant as a function of time for a given concentration.

The response time is entirely dependent on the tubing length and flow-rate. In this study, a standard flow-rate of 0.3 μL/min was used but a smaller tubing length (20 cm of 0.15 mm ID tubing+4 cm of 0.3 mm ID tubing) in order to speed up the process. When the flow-rate produced by the pump is accurate and consistent, the lag time will correspond to approx. 23.50 mins for a flow-rate of 0.3 μL/min through 20 cm of 0.15 mm ID tubing+4 cm of 0.3 mm ID tubing+ adaptor.

Figure 22:
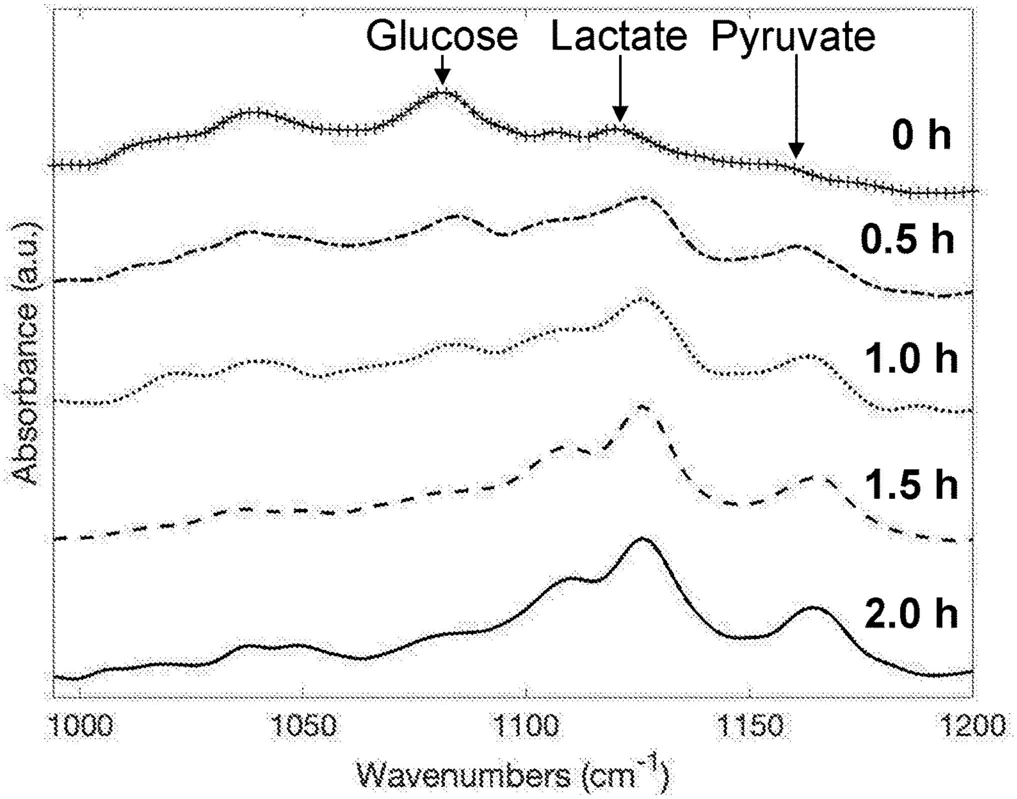
FIG. 22 is a graph of absorbance as a function of time for a patient over 2 hours.

FIG. 22 depicts infra-red (IR) sensor signals collected during 2 hours of microdialysis, in a TBI patient, showing a stacked plot of the spectra, with the position of peaks for glucose, lactate and pyruvate indicated. The clear change in brain chemistry can be easily seen by eye. When combined with a spectral analysis algorithm, small changes can be picked up every few minutes of measurement.

Figure 23A:
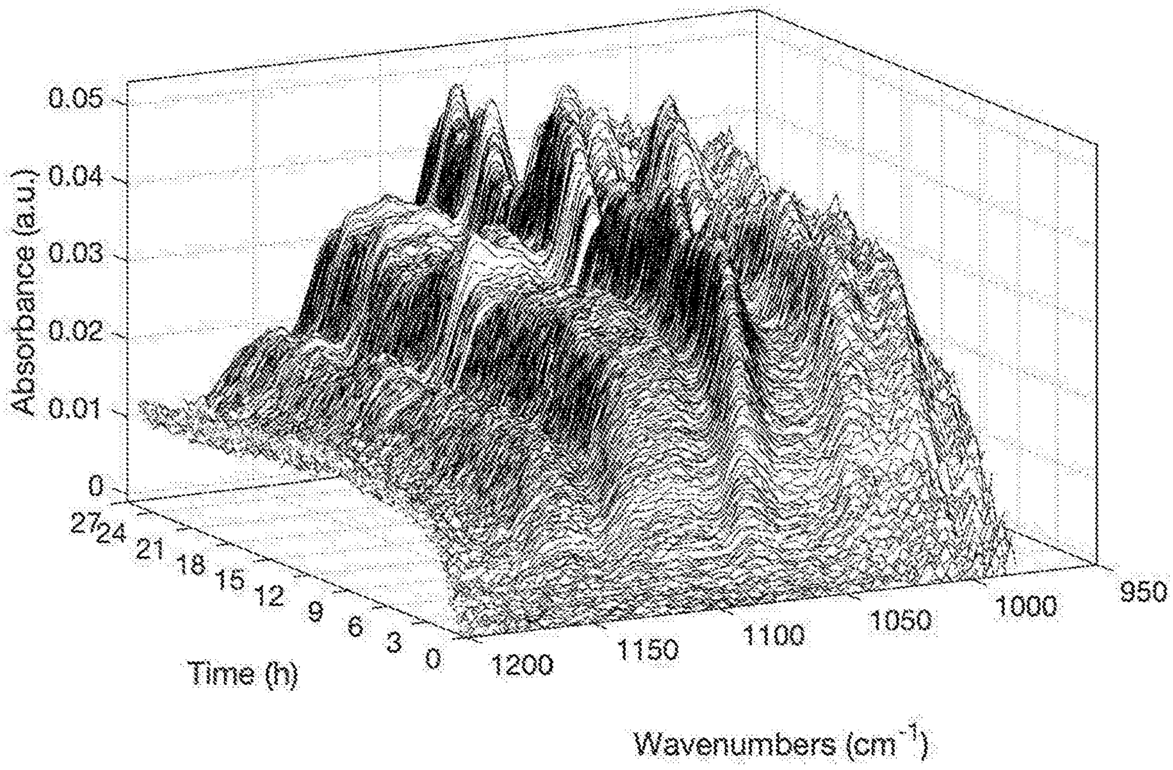
FIG. 23A is a graph of absorbance and wavenumber as a function of time for a patient over 21 hours.
Figure 23B:
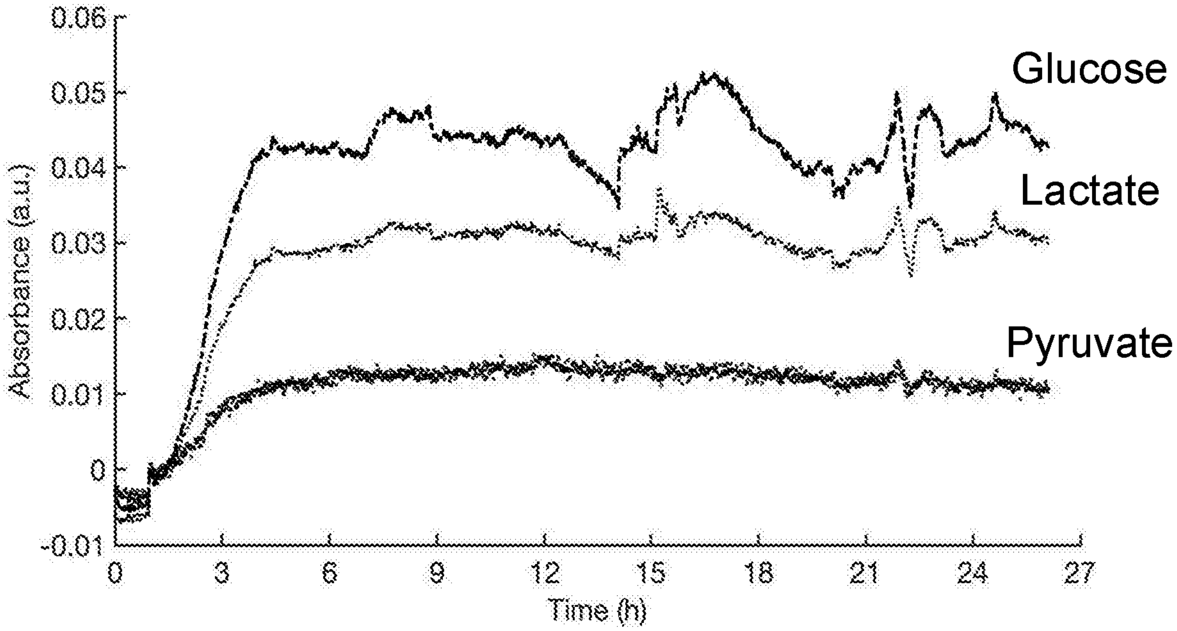
FIG. 23B is a graph of absorbance as a function of time for the patient.

FIG. 23A is a 3-dimensional graph of infra-red (IR) absorbance as a function of time and wavenumber for a TBI patient, showing 21 hours of monitoring. These spectra suggest variations with time for glucose and lactate, accompanied by a relatively constant level of pyruvate. FIG. 23B is a graph of absorbance as a function of time for the patient for glucose (wavenumber=1080 $cm^{-1}$), for lactate (wavenumber=1124 $cm^{-1}$) and for pyruvate (wavenumber=1176 $cm^{-1}$).

Figure 24:
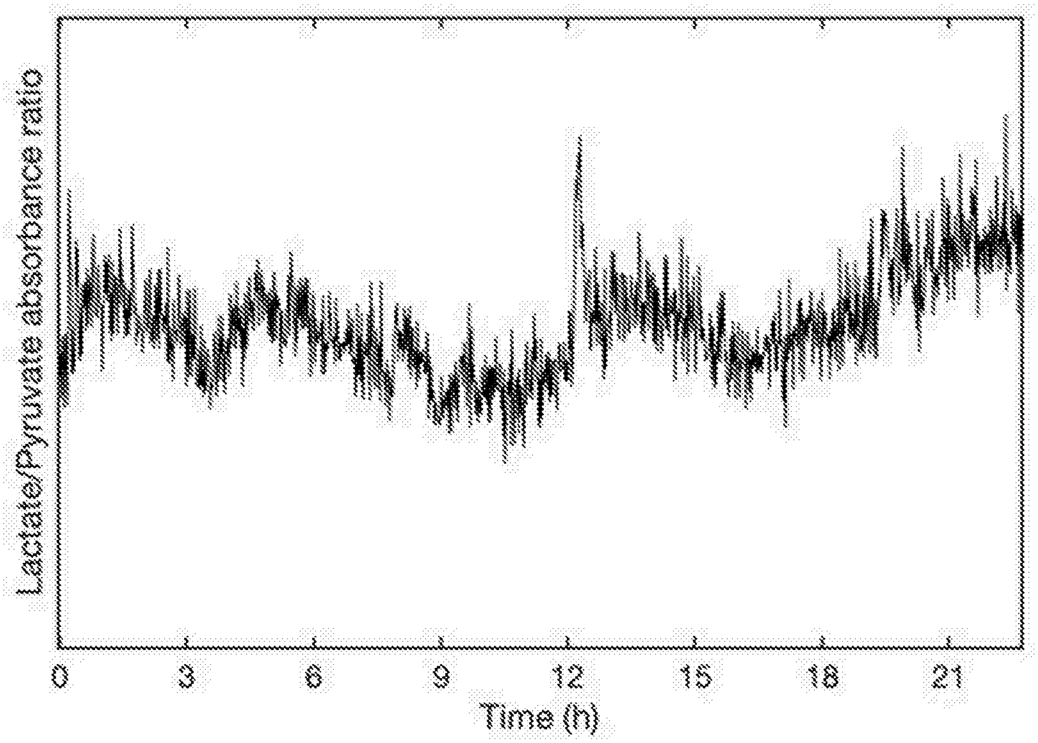
FIG. 24 is a graph of a ratio of lactate to pyruvate as a function of time for the patient of FIGS. 23A-23B.

FIG. 24 is a graph of a ratio of lactate to pyruvate as a function of time for the patient of FIGS. 23A to 23B. The ratio of lactate to pyruvate was calculated here as ratio of absorbance intensity for lactate (wavenumber=1124 $cm^{-1}$) divided by absorbance intensity for pyruvate (wavenumber=1176 $cm^{-1}$). Other methods such a multivariate analysis may offer an alternative and/or a more accurate method of ratio determination.

Patient Microdialysis Sample Off-Line Measurements (ISCUSflex and ChemDetect Analyzer)

Cerebral microdialysis samples collected consecutively on an hourly basis from two patients in the NCCU were measured on both an ISCUSflex Microdialysis Analyser and using the ChemDetect Analyzer, as described previously. Sixteen consecutive samples from two different patients (patient 1 and patient 2) were selected for this study in order to observe the differences in brain chemistry concentrations (ISCUSflex) between the two patients and to determine the correlation between these changes and the acquired spectra (using the ChemDetect Analyzer). Since the ISCUS Flex requires the entire sample volume provided by one vial, approximately 3 (sometimes 4) consecutive samples were pooled together to achieve sufficient volume for measurements on both instruments. These were then split equally into two separate vials: one to be measured on the ISCUSflex and the other to be measured on the ChemDetect. All samples were labelled in consecutive order and immediately frozen at −75° C. until just before measurements. Sixteen consecutive samples were measured for each patient and both ISCUSflex and ChemDetect measurements were carried out simultaneously in order to avoid any discrepancies between identical samples, for instance, due to sample evaporation.

Figure 25A:
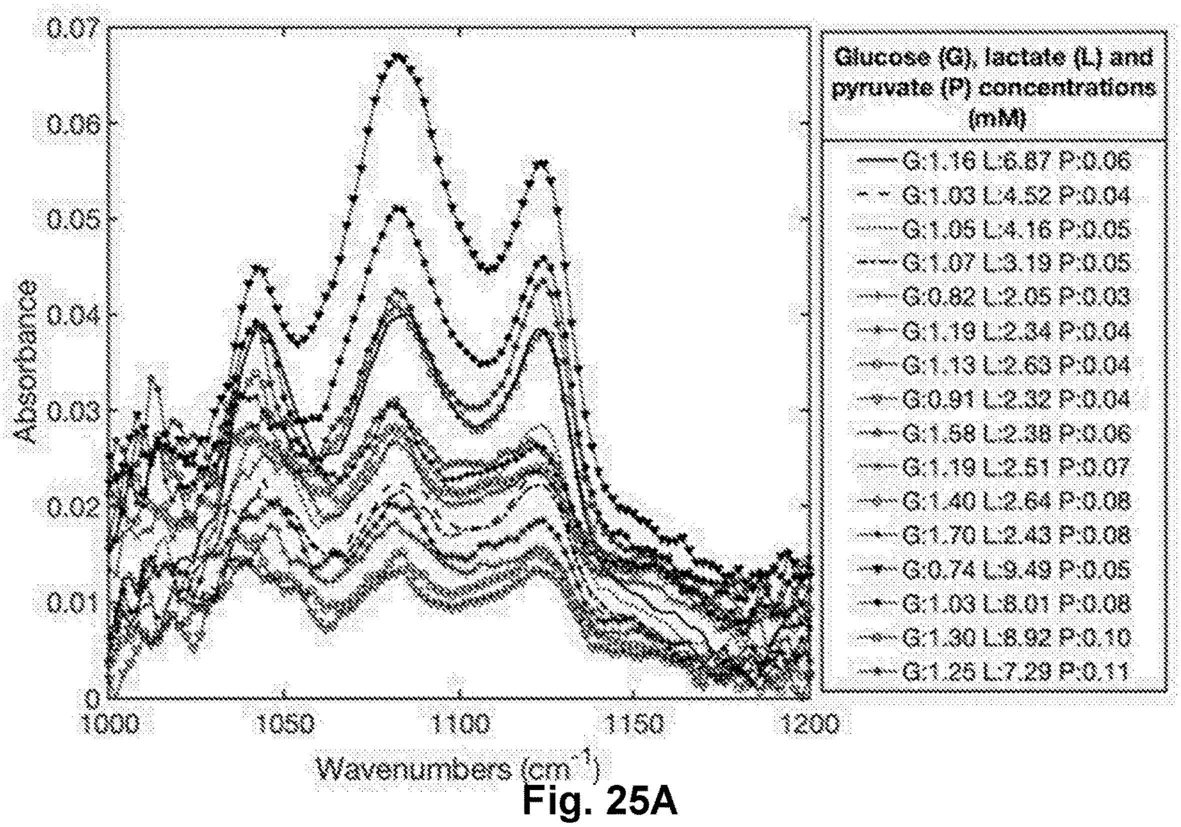
FIG. 25A shows absorbance spectra of 16 consecutively pooled microdialysis samples from patient 1 and corresponding compound concentrations measured separately on the ISCUSflex.
Figure 25B:
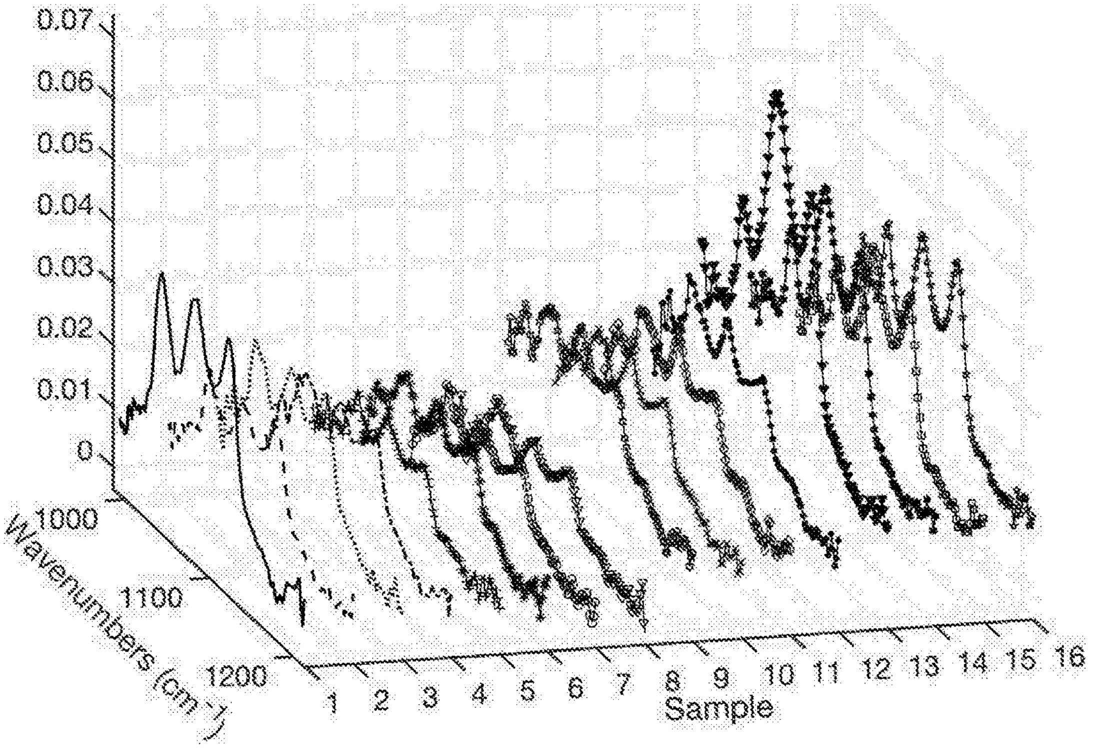
FIG. 25B shows observed spectral changes between consecutive microdialysis samples from patient 1 over a period of approximately 48 hours.
Figure 25C:
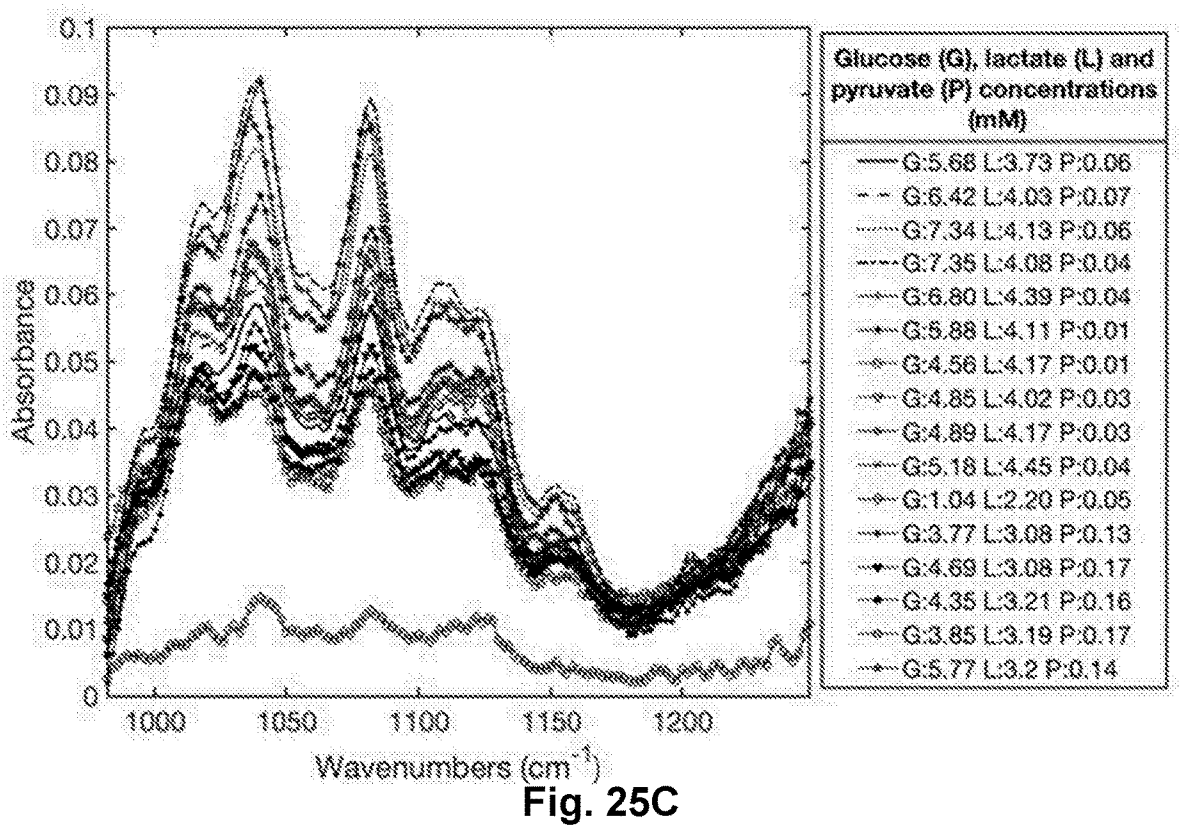
FIG. 25C shows absorbance spectra of 16 consecutively pooled microdialysis samples from patient 2 and corresponding compound concentrations measured separately on the ISCUSflex.
Figure 25D:
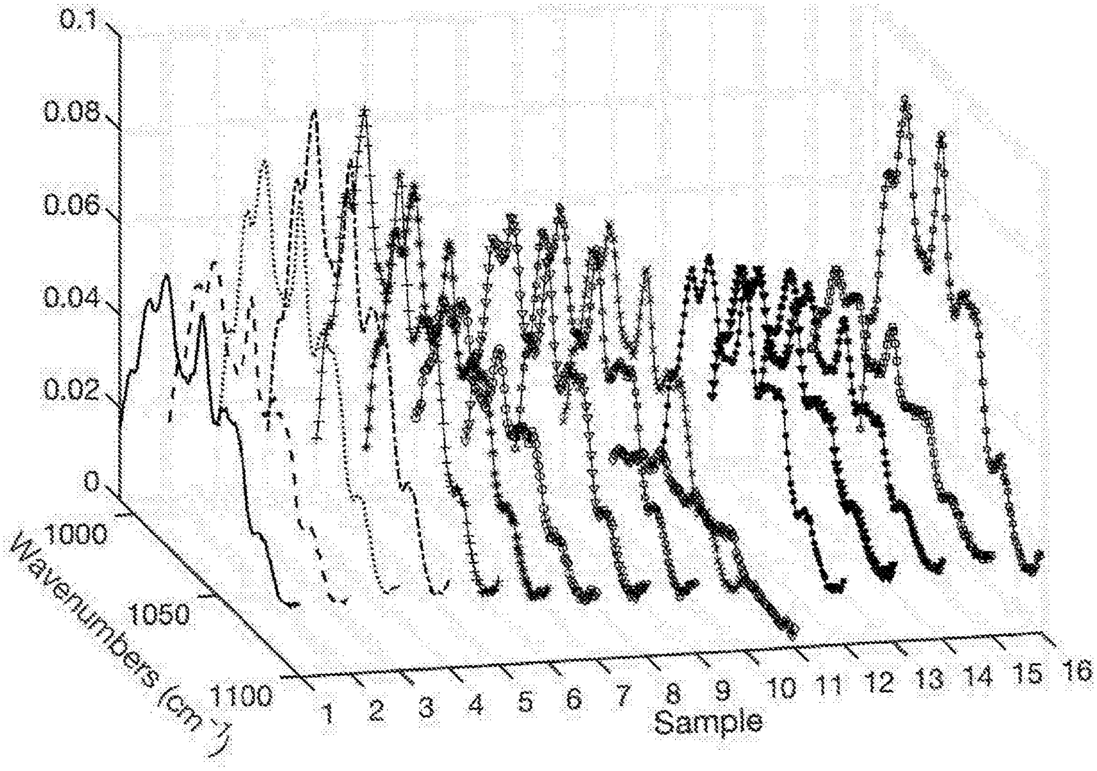
FIG. 25D shows observed spectral changes between consecutive microdialysis samples from patient 2 over a period of approximately 48 hours. Note: As a result of sample pooling, each spectrum corresponds to the average concentration over approximately 3 hours.
Figure 25E:
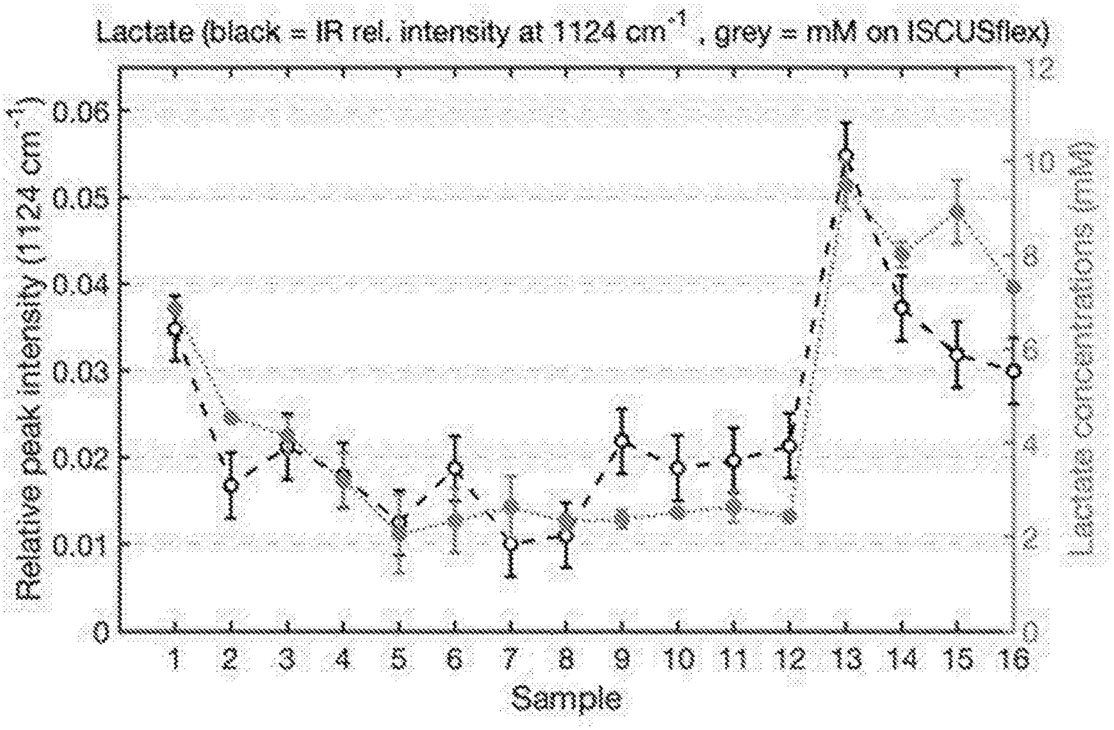
FIG. 25E compares relative peak intensity for lactate peak at 1124 $cm^{-1}$ using ChemDetect and lactate concentration measured using the ISCUSflex, showing agreement.
Figure 25F:
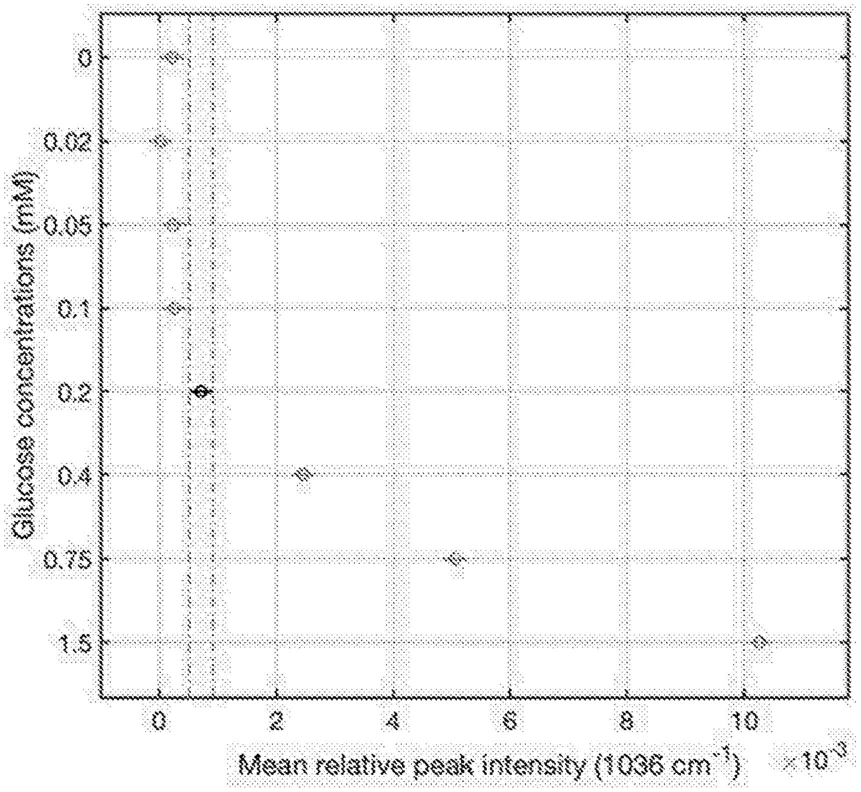
FIG. 25F shows one-way ANOVA and multi-comparison test for the glucose peak at 1036 $cm^{-1}$ using ChemDetect. The LoQ for the 1036 $cm^{-1}$ glucose peak is between 0.1 and 0.2 mM. Note: the entire range of concentrations is not shown here for clarity.
Figure 25G:
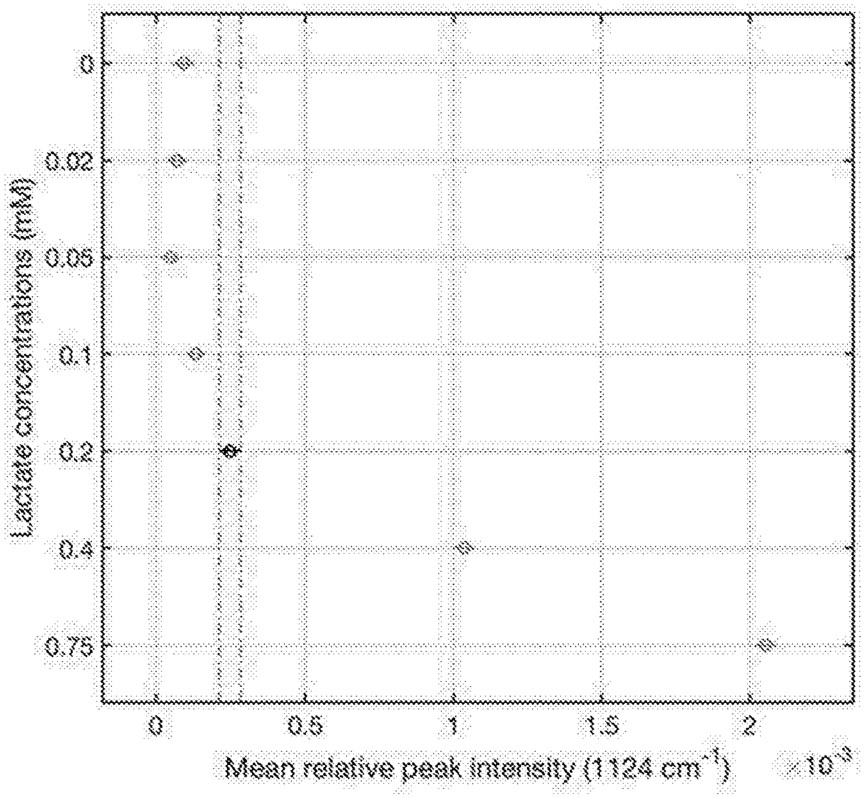
FIG. 25G shows one-way ANOVA and multi-comparison test for the lactate peak at 1124 $cm^{-1}$ using ChemDetect. The LoQ for the 1124 $cm^{-1}$ lactate peak is between 0.1 and 0.2 mM. Note: the entire range of concentrations is not shown here for clarity.
Figure 25H:
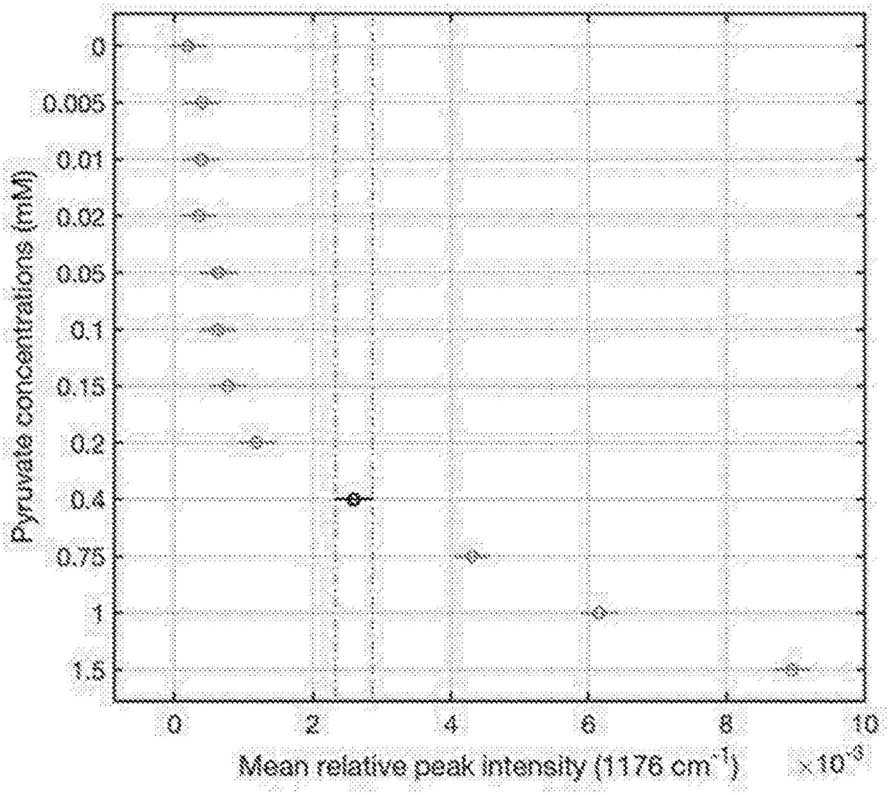
FIG. 25H shows one-way ANOVA and multi-comparison test for the pyruvate peak at 1176 $cm^{-1}$ using ChemDetect. The LoQ for the 1176 $cm^{-1}$ pyruvate peak is between 0.2 and 0.4 mM. Note: the entire range of concentrations is not shown here for clarity.

FIG. 25A shows the mid-infrared spectra of the 16 samples of patient 1 as well as the corresponding concentrations of each compound obtained from the ISCUSflex analysis. Three strong peaks were observed in all spectra at 1042 $cm^{-1}$, 1080 $cm^{-1}$, and 1124 $cm^{-1}$. An immediate analysis suggests that these correspond to the C—O stretches of lactate (1124 $cm^{-1}$ and 1042 $cm^{-1}$) and glucose (1080 $cm^{-1}$). However, since the glucose peak at 1080 $cm^{-1}$ is prominent compared to its usually stronger peak at 1036 $cm^{-1}$, which is not seen in the spectra, it is possible that there is a large contribution from the weak lactate peak at 1086 $cm^{-1}$. The fact that patient 1 exhibits particularly low concentrations of glucose and high concentrations of lactate, contributes to this assumption. By analyzing the spectra acquired on the ChemDetect Analyzer and the concentrations obtained by the ISCUSflex, a clear correlation is observed between the lactate peaks, especially the peak at 1124 $cm^{-1}$, and its concentration at different time-points as shown in FIG. 25B (i.e. when the lactate concentration increases, the absorbance intensities of the lactate peaks increase and vice-versa). Patient 2 exhibits higher concentrations of glucose compared to lactate. The resulting spectra in FIG. 25C exhibit prominent glucose peaks at 1036, 1080, 1108 and 1152 $cm^{-1}$ and a shoulder at 1124 $cm^{-1}$, corresponding to the lactate peak. FIG. 25D demonstrates a strong correlation between the absorbance intensities of the (predominant) glucose peaks and these glucose concentrations (i.e. when the glucose concentration increases, the absorbance intensities of the glucose peaks increase and vice-versa). FIG. 25E shows agreement between peak intensities for lactate measured on the ChemDetect Analyzer and the concentrations obtained by the ISCUSflex. FIGS. 25F to 25G show limit of quantitation (LOQ) determinations for glucose, lactate and pyruvate, respectively, as summarized in Table 2.

TABLE 2

LOQ for analytes of interest.

| | Compound | Peak ($cm^{-1}$) | Gradient, m | $R^2$ | LOQ (mM) |
|---|---|---|---|---|---|
| Transmission-FTIR | Glucose | 1136 | 0.0021 | 0.995 | 0.75-3 |
| QCL-system | Glucose | 1136 | 0.0069 | 0.998 | 0.1-0.2 |
| | Lactate | 1124 | 0.0028 | 0.999 | 0.1-0.2 |
| | Pyruvate | 1176 | 0.0058 | 0.994 | 0.2-0.4 |

Multivariate Data Analysis for Predicting Microdialysate Concentrations

This section discusses the development of a statistical model for the prediction of glucose, lactate and pyruvate concentrations in patient microdialysis samples. The analytical method used for developing the model and quantifying the predictability of the different solutions was Partial Least Squares Regression (PLSR) which is commonly used for spectral analysis. Firstly, given the limited number of patient samples, a model was developed using synthetic samples consisting of three-component mixtures (of glucose, lactate and pyruvate) in central nervous system (CNS) perfusion fluid within a range of clinically-relevant concentrations. This model was then used to predict the concentrations of glucose, lactate and pyruvate in patient microdialysates, which were compared against measurements obtained separately using the standard microdialysis analyzer (ISCUSFlex Microdialysis Analyser).

Synthetic Samples for PLSR Model

Figure 26A:
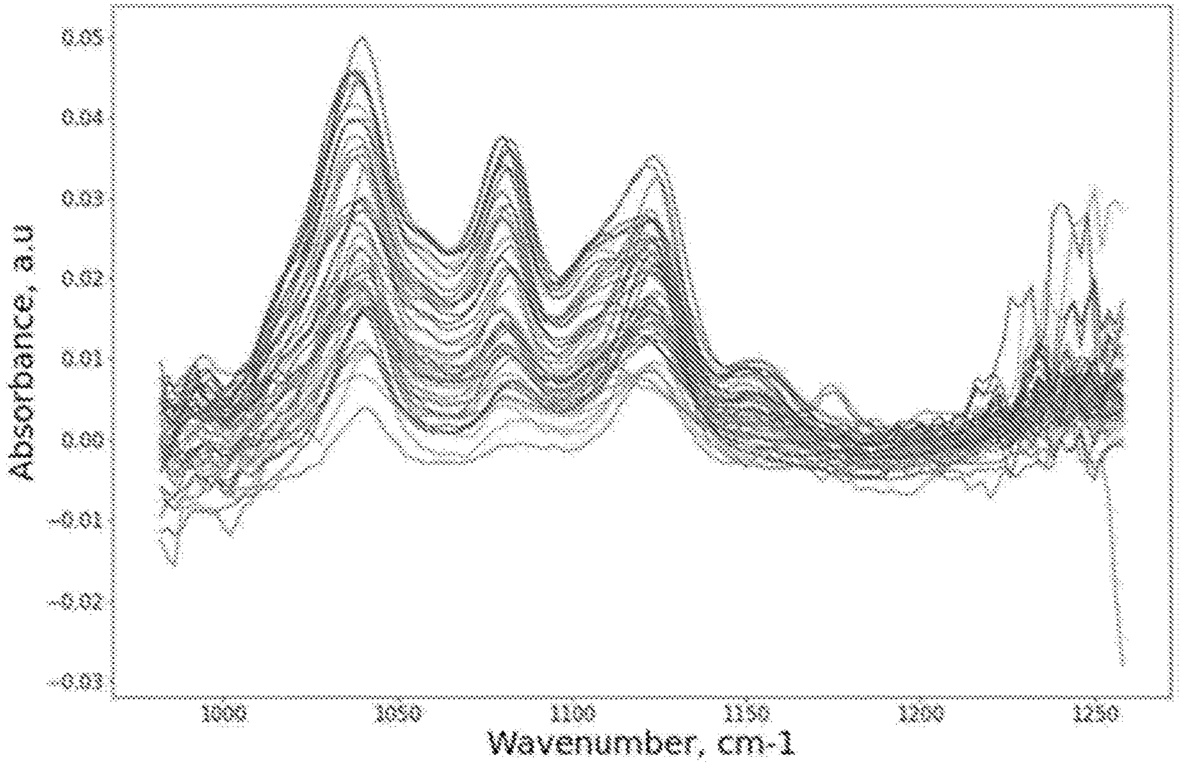
FIGS. 26A and 26B show absorbance spectra of 46 synthetic samples acquired on QCL-system.
Figure 26B:
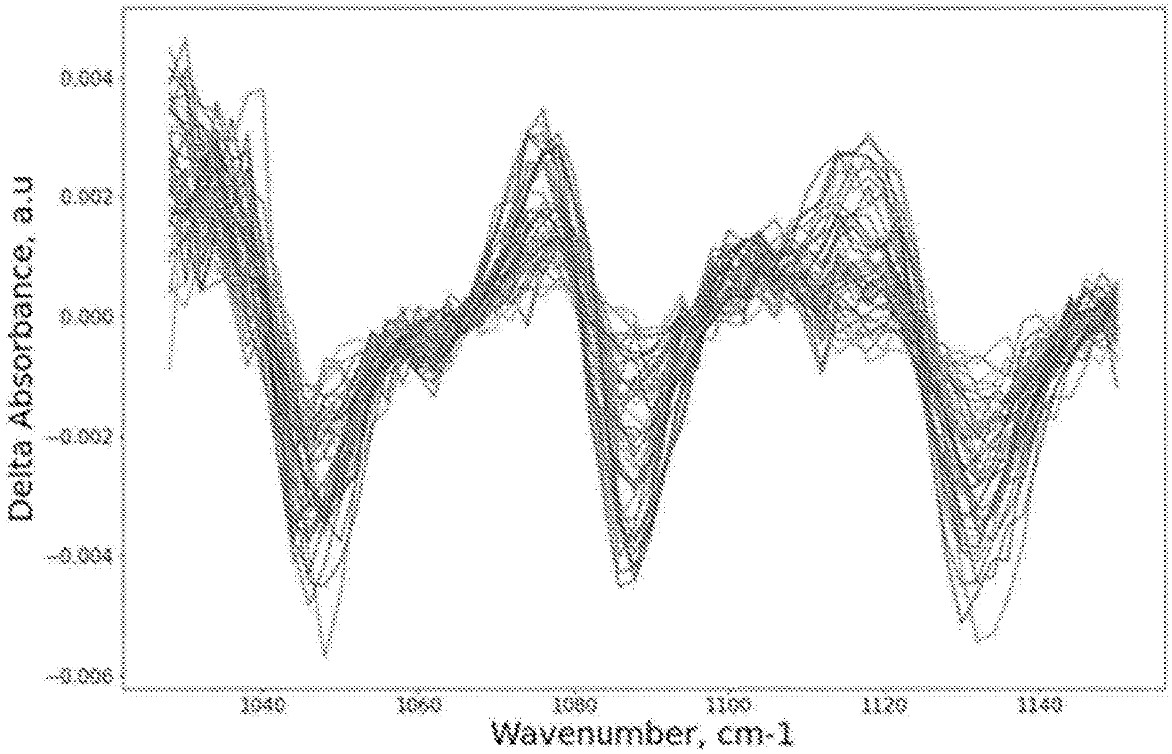

Synthetic samples were used for development of a Partial Least Squares Regression (PLSR) model for subsequent use in predicting patient-sample concentrations. A simple uniform selection algorithm with reject sampling was developed and used to generate a list of 50 samples containing different combinations of glucose, lactate and pyruvate concentrations within ranges that are typical TBI-patient microdialysate compound concentrations Four outliers were excluded, and the remaining 46 spectra used to generate and test the model are shown in FIG. 26A. The first derivative of the spectra was calculated and the spectral range used was between 1025 and 1150 $cm^{-1}$. The processed spectra are shown in FIG. 26B.

Figure 27A:
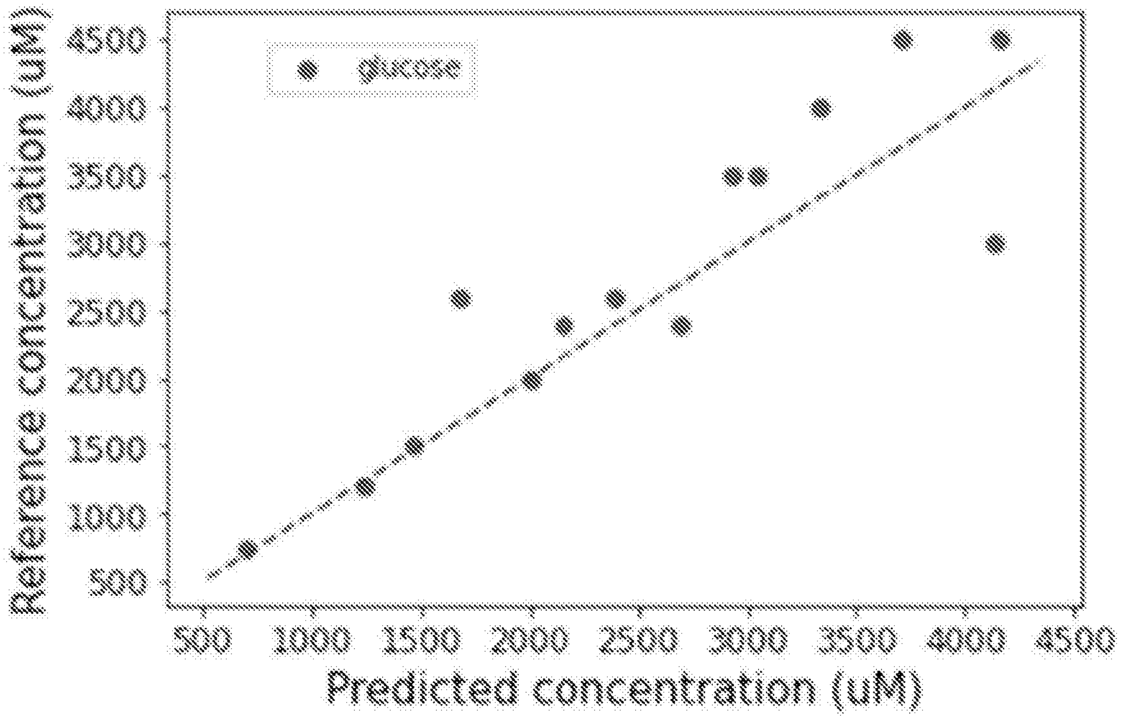
FIGS. 27A to 27C show predicted concentration levels in the 14 test samples plotted against reference concentrations.
Figure 27B:
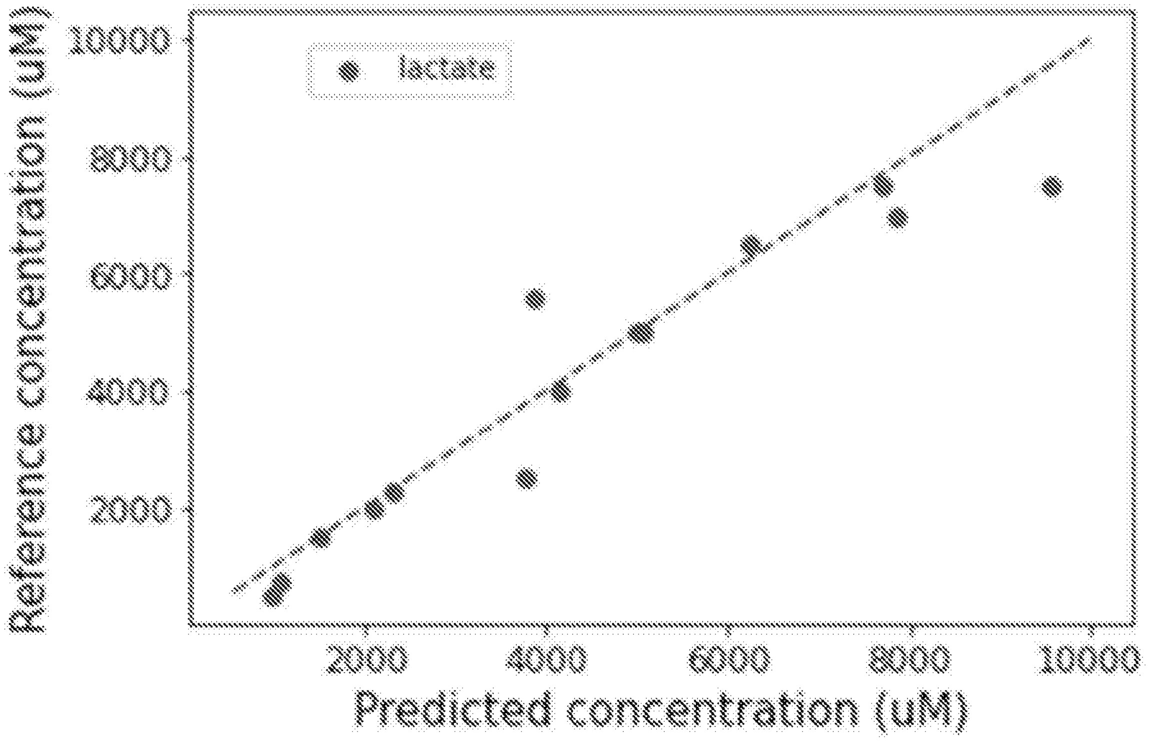
Figure 27C:
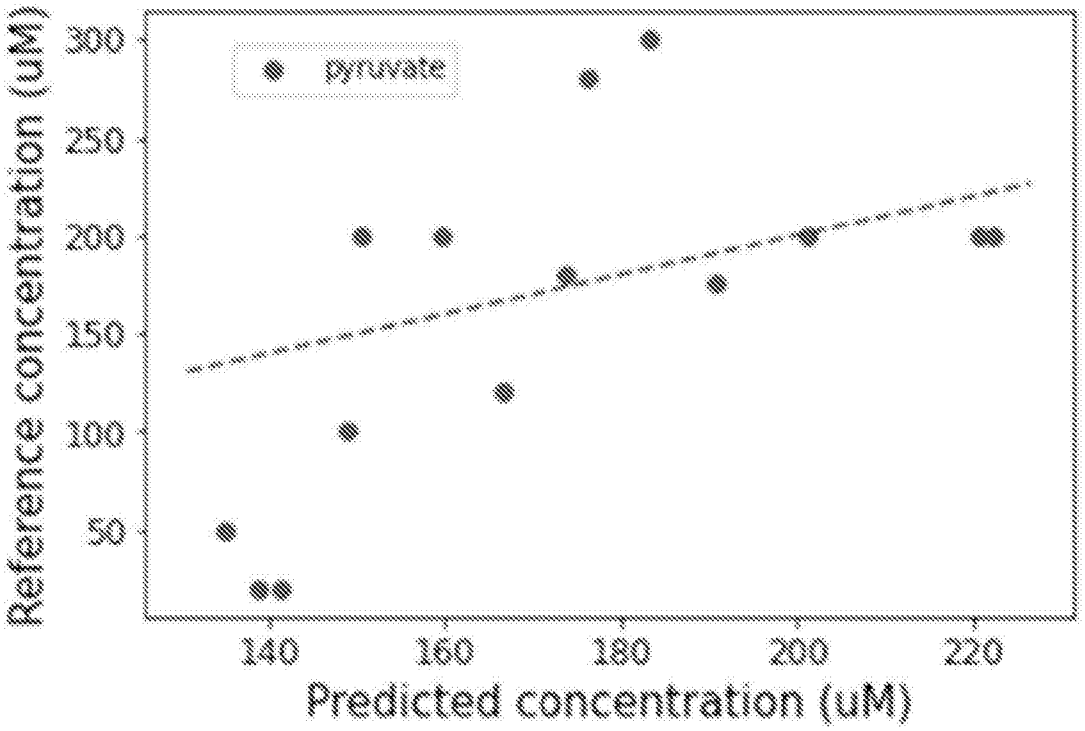

A PLSR model was built, and the number of PLSR components used, 3 was calibrated based on k-fold cross validation, where the spectral data were randomly split into the following sub-sample sets: the in-sample set, comprising of 19 spectra; the out-sample set comprising of 13 spectra; and the test sample set, comprising of the remaining 14 spectra. Here, a single sub-sample (test sample) was retained as the final validation for testing of the model. Finally, the performance of the PLSR model in predicting each compound was evaluated using the Root Mean Squared Error (RMSE) of each compound in the test set as shown in Table 3. The correlation between the predicted vs. real concentrations is shown in FIGS. 27A to 27C. A good correlation between the predicted and reference concentrations can be seen for glucose and lactate. For pyruvate the correlation is not good because of the significantly lower concentrations resulting in barely any absorbance peak.

TABLE 3

RMSE for analytes of interest

| Compound | Test sample RMSE (μM) |
|---|---|
| glucose | 538 |
| lactate | 848 |

Figure 28A:
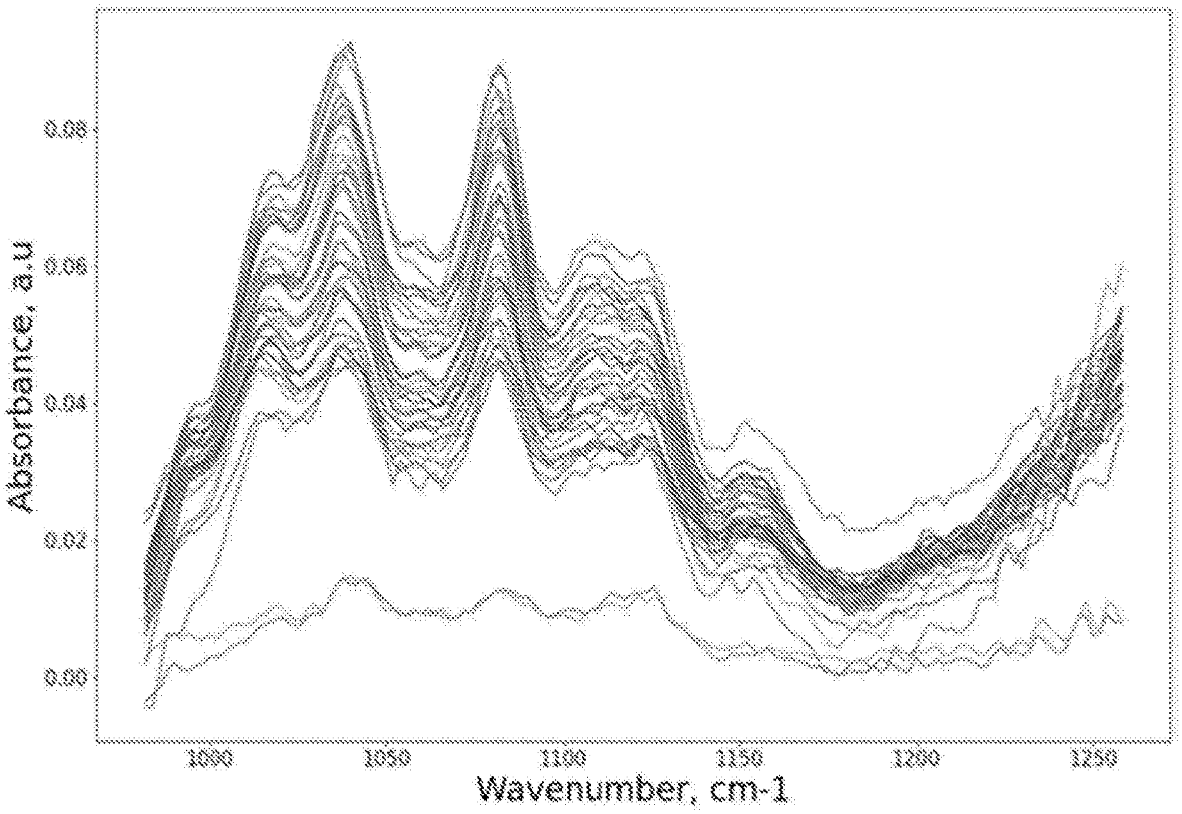
FIGS. 28A and 28B show absorbance spectra of 40 successive microdialysis samples from patient 2 acquired on the QCL system.
Figure 28B:
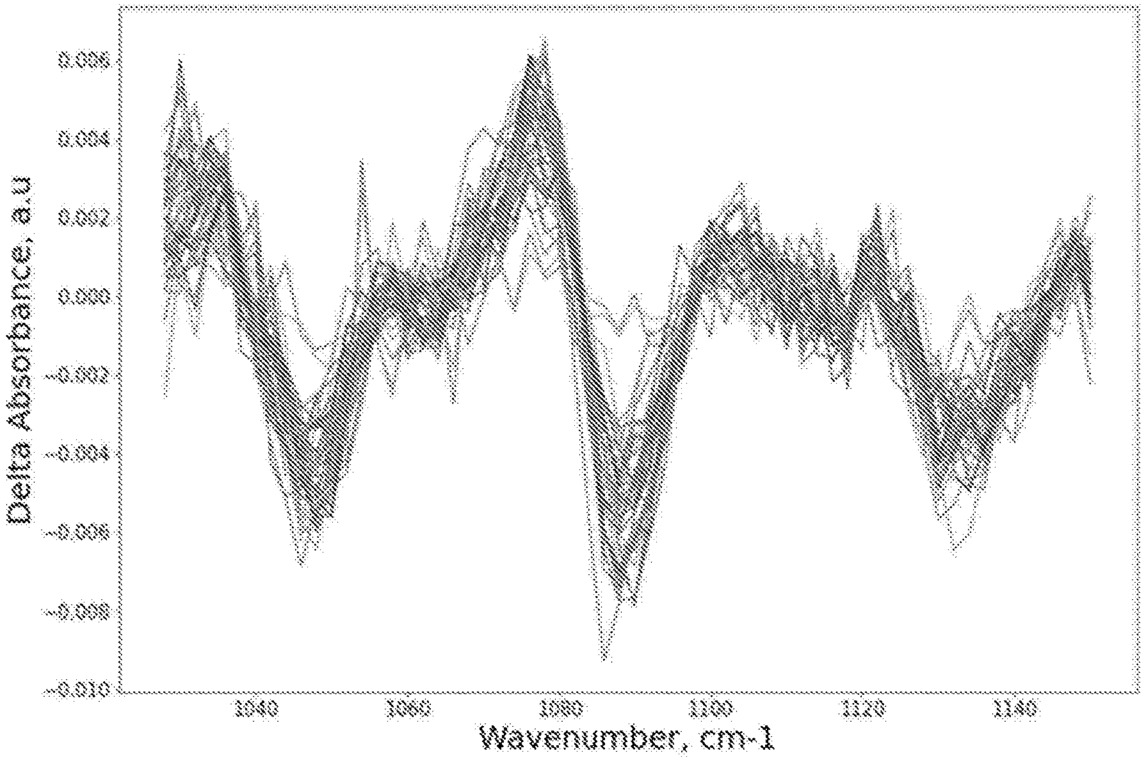

PLSR Prediction of Glucose and Lactate Concentrations in Patient Microdialysates The PLSR model developed in the previous subsection was used to predict the concentrations of glucose and lactate in 40 successive microdialysis samples from patient 2, which were compared against reference concentration measurements obtained separately using the standard microdialysis analyser (ISCUSflex Microdialysis Analyser). FIGS. 28A and 28B show the absorbance spectra obtained for each sample, plotted in the relevant spectral range, before and after data preprocessing.

Figure 29A:
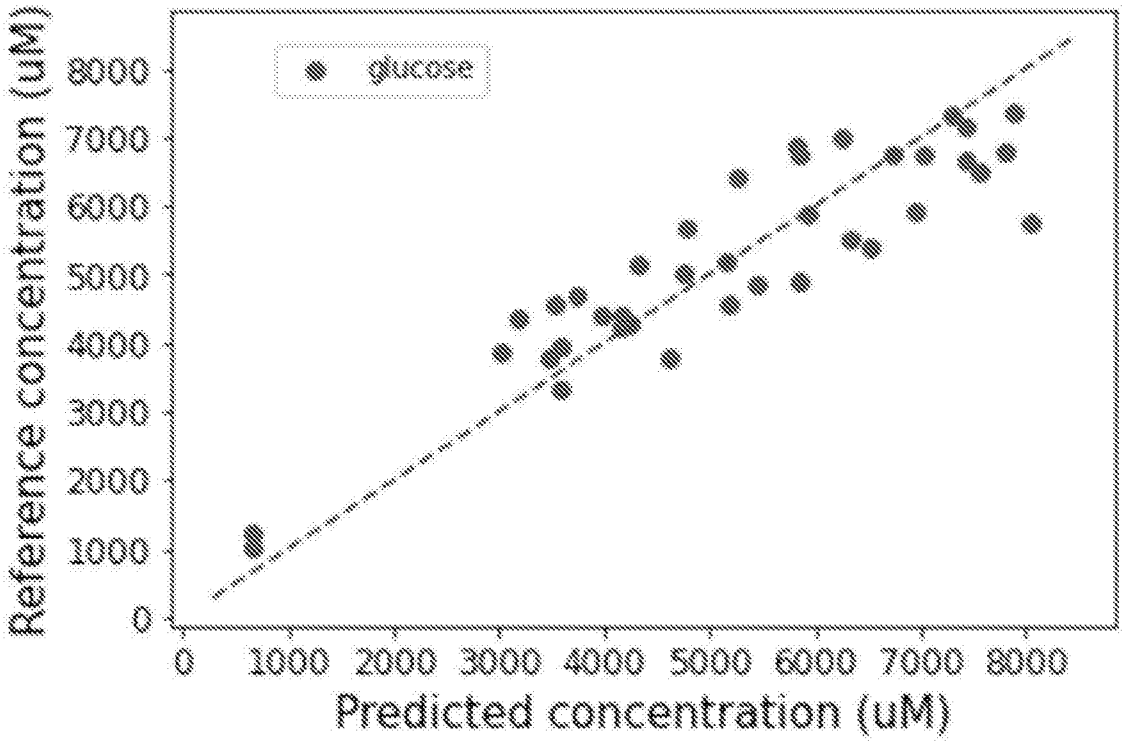
FIGS. 29A and 29B show predicted concentration levels in the 40 microdialysis samples from patient 2 plotted against reference concentration.
Figure 29B:
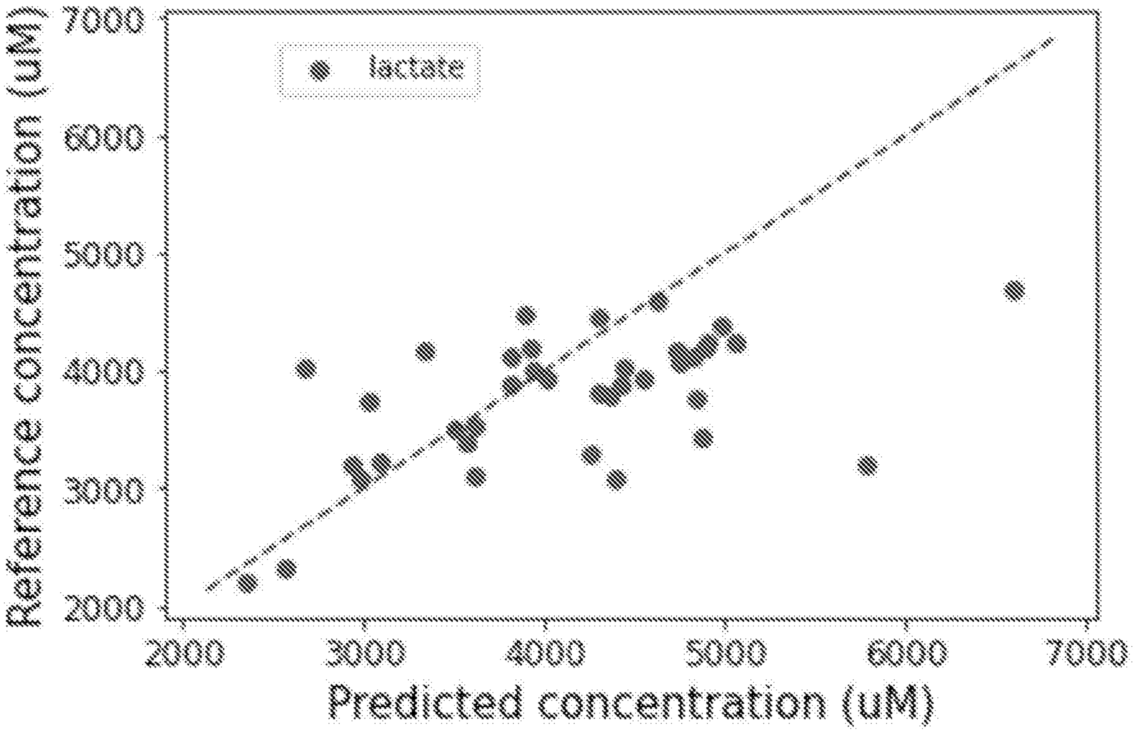

FIGS. 29A and 29B show the predicted glucose and lactate concentrations for the 40 microdialysis samples from patient 2. The respective RMSE values for each compound are shown in Table 4.

TABLE 4

RMSE for analytes of interest

| | Test sample RMSE (μM) |
|---|---|
| glucose | 796 |
| lactate | 809 |

Figure 30A:
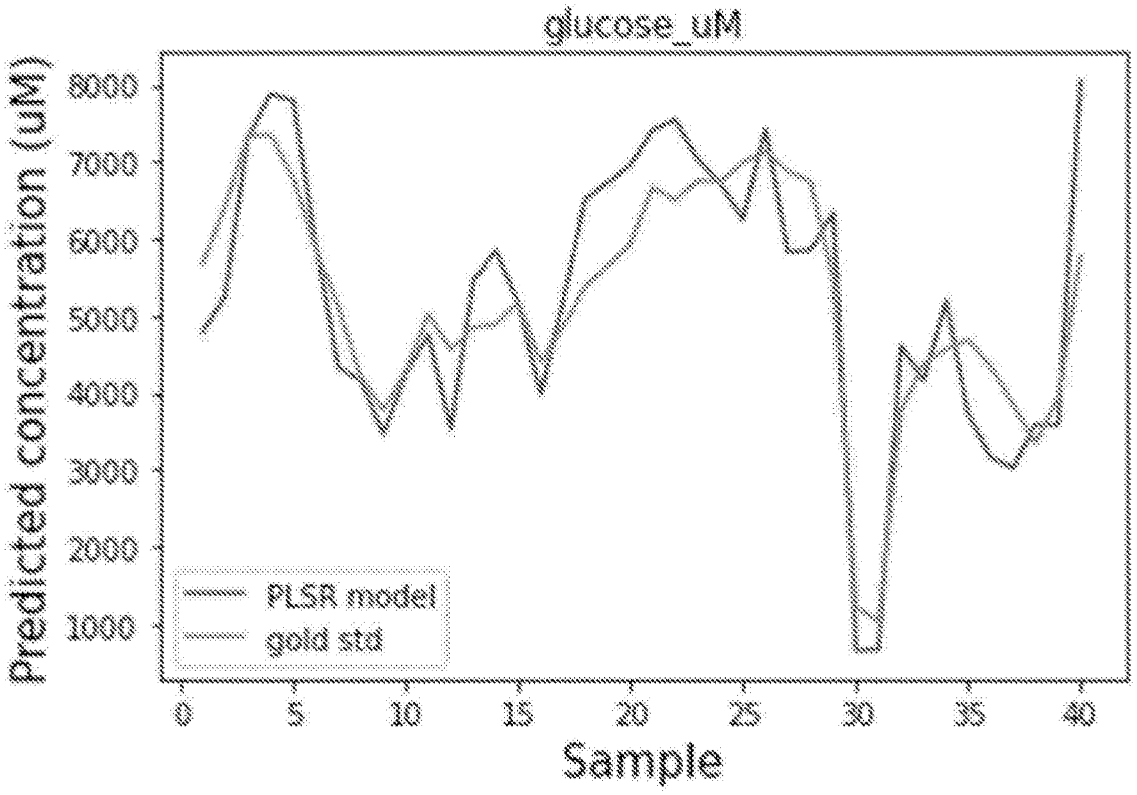
FIGS. 30A and 30B show predicted concentration levels vs. concentrations obtained from the standard microdialysis analyzer measured concentration in the 40 microdialysis samples from patient 2 plotted against sample number.
Figure 30B:
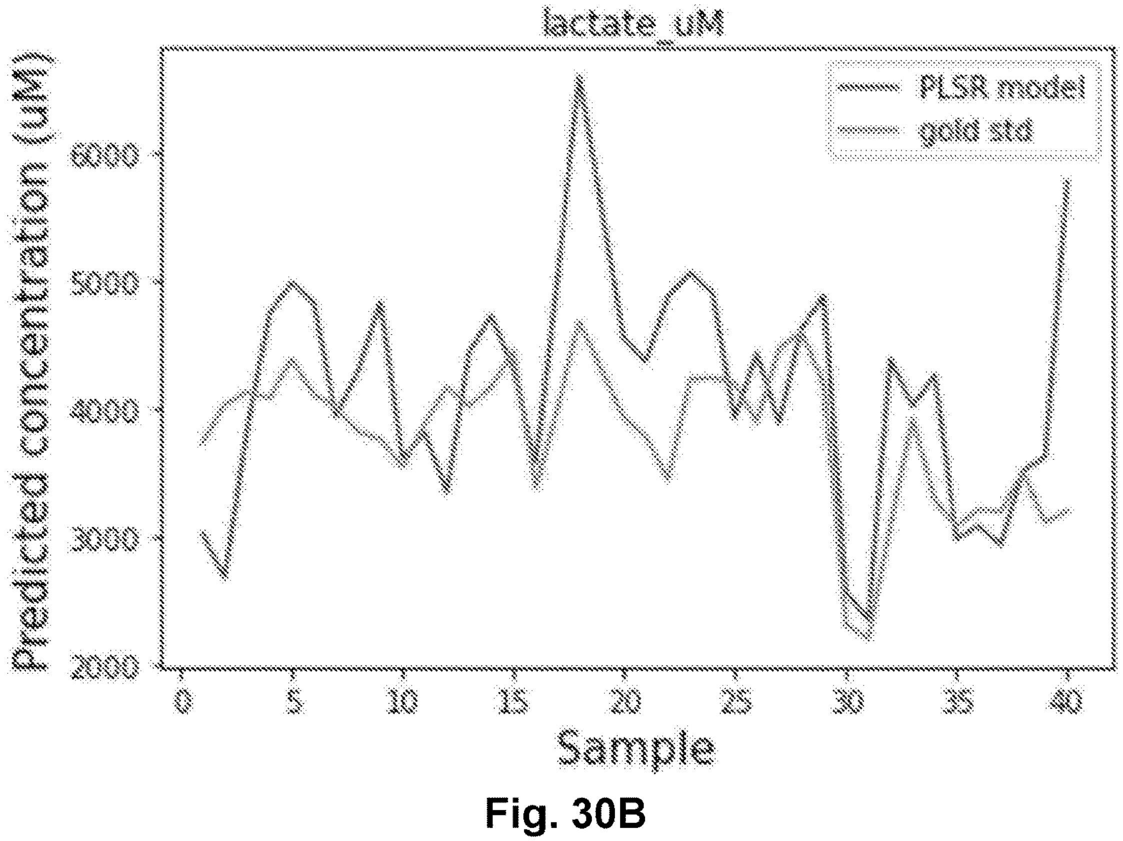

FIGS. 30A and 30B show the concentrations; real vs. predicted for the consecutively collected patient 2 samples. The results show that there is a very good correlation between the gold standard (ISCUSflex) and the developed model.

Figure 30C:
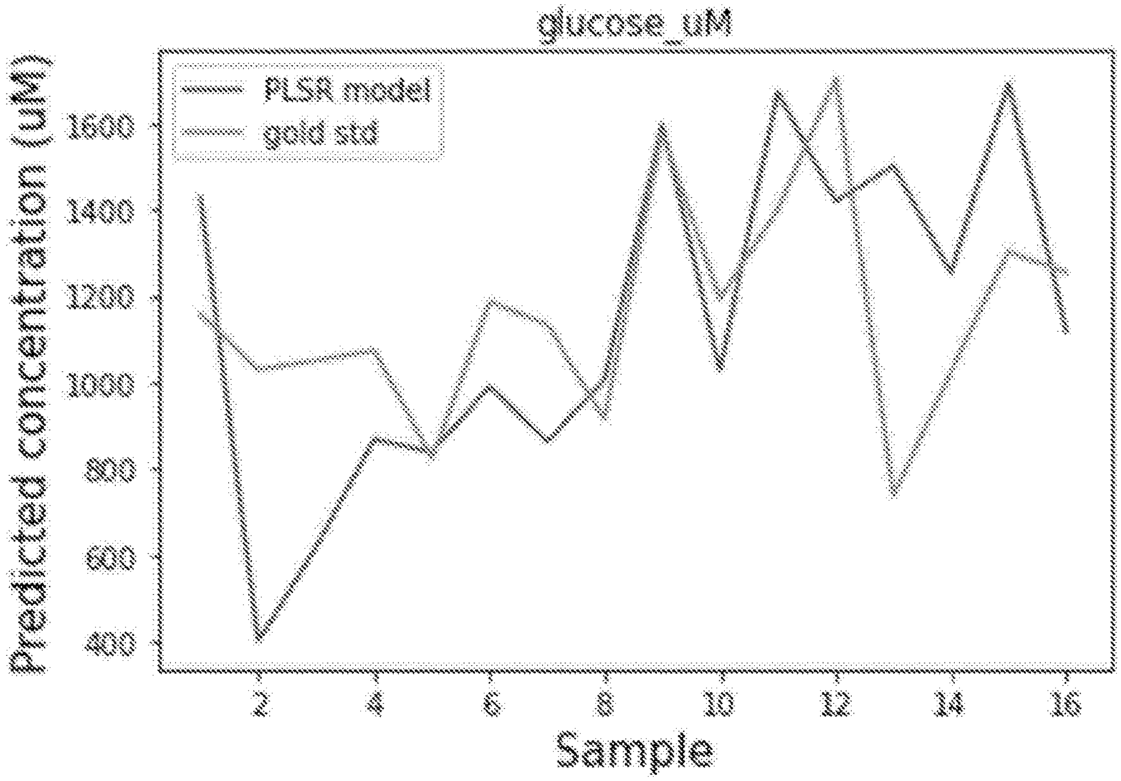
FIGS. 30C and 30D show predicted concentration levels vs. concentrations obtained from the standard microdialysis analyzer measured concentration in 16 successive microdialysis samples from patient 1 plotted against sample number.
Figure 30D:
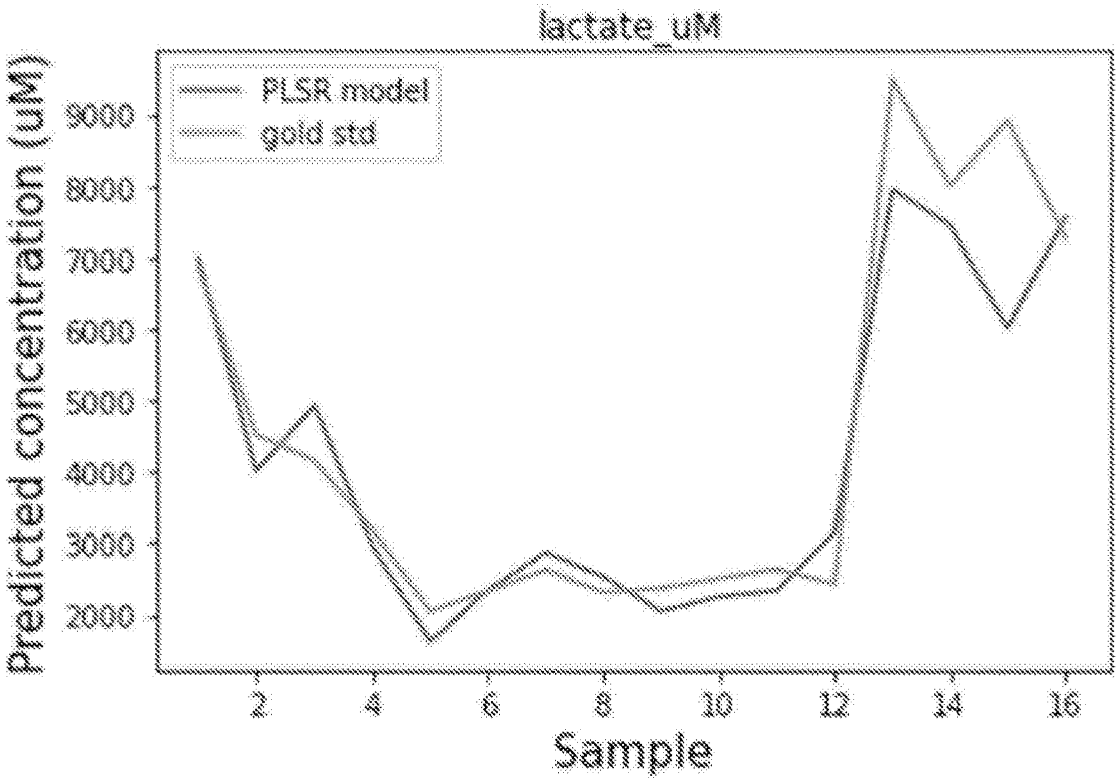

FIGS. 30C and 30D similarly show the concentrations; real vs. predicted for the 16 consecutively collected patient 1 samples. The results again show that there is a very good correlation between the gold standard (ISCUSflex) and the developed model.

Although a preferred embodiment has been shown and described, it will be appreciated by those skilled in the art that various changes and modifications might be made without departing from the scope of the invention, as defined in the appended claims and as described above.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims and drawings), and/or all of the steps of any method or process so disclosed, may be combined in any combination, except combinations where at most some of such features and/or steps are mutually exclusive.

Each feature disclosed in this specification (including any accompanying claims, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims and drawings), or to any novel one, or any novel combination, of the steps of any method or process so disclosed.

The invention claimed is:

1. A detector assembly for determining a ratio of lactate to pyruvate from dialysis, the detector assembly comprising:
- a first pump of a set of pumps,
- a dialysis probe which is insertable into one of: a fluid in a patient or an organ in a patient, the dialysis probe having an inlet configured to receive a perfusate, an outlet configured to output a dialysate, and a dialysis membrane configured to allow analytes in the patient to flow into the perfusate to form the dialysate,
- a first tube of a set of tubes arranged to fluidically couple the first pump to the inlet of the dialysis probe,
- an infrared (IR) detector, wherein the IR detector comprises a quantum cascade laser (QCL) based IR detector,
- a second tube of the set of tubes arranged to fluidically couple the outlet of the dialysis probe to the IR detector and
- a controller;
- wherein the first pump is arranged to:
  - pump, via the first tube, the perfusate at a first flow rate of a set of flow rates to the inlet of the dialysis probe, when the dialysis probe is inserted into the patient; and
  - in turn pump, at least in part, the dialysate at a second flow rate of the set of flow rates from the outlet of the dialysis probe to the IR detector via the second tube;
- wherein the IR detector is arranged to detect, using non-destructive IR detection, respective absorbances due, at least in part, to lactate and pyruvate in the dialysate; and
- wherein the controller is arranged to determine the ratio of lactate to pyruvate in the dialysate based, at least in part, on the detected respective absorbances.

2. The detector assembly of claim 1, wherein the IR detector is arranged to detect an absorbance due, at least in part, to one or more of glucose, glutamate, alanine, glutamine or glycerol in the dialysate.

3. The detector assembly of claim 1, wherein the controller is arranged to provide a first output signal, based, at least in part, on the ratio of lactate to pyruvate in the dialysate for controlling infusion of an infusate into the fluid.

4. The detector assembly of claim 1, wherein the controller is arranged to provide a second output signal, based, at least in part, on a change of a detected absorbance.

5. The detector assembly of claim 1, wherein the controller is arranged to determine the ratio of lactate to pyruvate in the dialysate one of: periodically, frequently or continuously.

6. The detector assembly of claim 1, wherein the set of pumps comprises a second pump arranged to pump, at least in part, the dialysate at the second flow rate of the set of flow rates from the dialysis probe to the IR detector via the second tube, wherein the second flow rate is greater than the first flow rate.

7. The detector assembly according to claim 6, wherein the controller is arranged to control the second pump to pump the dialysate at the second flow rate of the set of flow rates.

8. The detector assembly of claim 1, comprising a first valve of a set of valves arranged to direct the dialysate at the second flow rate of the set of flow rates from the outlet of the dialysis probe to the IR detector via the second tube.

9. The detector assembly of claim 1, wherein the IR detector comprises a flow cell arranged proximal to the outlet of the dialysis probe.

10. The detector assembly of claim 9, wherein the flow cell has a path length in a range from 10 μm to 1000 μm, from 25 μm to 500 μm, or from 50 μm to 250 μm.

11. The detector assembly of claim 1, wherein the controller is arranged to compare the ratio of lactate to pyruvate in the dialysate with respect to output signals from a set of patient sensors.

12. The detector assembly of claim 1, wherein the first tube has an internal diameter in a range of one of approximately: from 10 μm to 1,000 μm, from 50 μm to 500 μm, or from 100 μm to 250 μm.

13. The detector assembly of claim 1, wherein the first tube has a length in a range of one of approximately: from 10 mm to 1,000 mm, from 50 mm to 500 mm, or from 100 mm to 250 mm.

14. The detector assembly of claim 1, wherein the second tube has an internal diameter in a range of one of approximately: from 10 μm to 1,000 μm, from 50 μm to 500 μm, or from 100 μm to 250 μm.

15. The detector assembly of claim 1, wherein the second tube has a length in a range of one of approximately: from 10 mm to 1,000 mm, from 50 mm to 500 mm, or from 100 mm to 750 mm.

16. The detector assembly of claim 1, wherein the IR detector is arranged to detect respective absorbances having wavenumbers in the range between and inclusive of 1036 $cm^{-1}$ to 1176 $cm^{-1}$.

17. The detector assembly of claim 1, wherein the IR detector is arranged to detect the respective absorbances due, at least in part, to the lactate and the pyruvate in the dialysate for an integration time that is selected according to the concentrations of at least one of the lactate or the pyruvate in the dialysate, or a signal to noise ratio for at least one of the lactate or the pyruvate in the dialysate.

18. A method of determining a ratio of lactate to pyruvate from dialysis, the method comprising:
- pumping, by a first pump of a set of pumps, a perfusate at a first flow rate of a set of flow rates to an inlet of a dialysis probe, wherein the dialysis probe is inserted into one of: a fluid in a patient or an organ in a patient, wherein the inlet of the dialysis probe is fluidically coupled to the first pump via a first tube of a set of tubes, and wherein the dialysis probe comprises a dialysis membrane configured to allow analytes in the patient to flow into the perfusate to form a dialysate;
- in turn pumping, at least in part, the dialysate at a second flow rate of the set of flow rates from an outlet of the dialysis probe to an infrared (IR) detector via a second tube of the set of tubes, wherein the IR detector comprises a quantum cascade laser (QCL) based IR detector;
- detecting, using non-destructive IR detection by the IR detector, respective absorbances due, at least in part, to lactate and pyruvate in the dialysate; and determining, by a controller, the ratio of lactate to pyruvate in the dialysate based, at least in part, on the detected respective absorbances.

19. The method of claim 18, further comprising:

detecting, by the IR detector, an absorbance due, at least in part, to glucose in the dialysate; and determining, by the controller, a ratio of glucose to lactate in the dialysate based, at least in part, on the detected respective absorbances.

20. The method of claim 18, further comprising:

providing, by the controller, a first output signal, based, at least in part, on the ratio of lactate to pyruvate in the dialysate; and controlling infusion of an infusate into the fluid.

21. The method of claim 18, further comprising:

providing, by the controller, a second output signal, based, at least in part, on a change of a detected absorbance.

22. The method of claim 18, further comprising:

detecting, by the IR detector, an absorbance due, at least in part, to glycerol in the dialysate.

23. The method of claim 18, further comprising:

controlling, by the controller, the first pump to pump the perfusate at the first flow rate of the set of flow rates.

24. The method of claim 18, further comprising:

pumping, by a second pump of the set of pumps, at least in part, the dialysate at the second flow rate of the set of flow rates from the dialysis probe to the IR detector via the second tube, wherein the second flow rate is greater than the first flow rate.

25. The method of claim 18, further comprising:

directing, by a first valve of a set of valves, the dialysate at the second flow rate of the set of flow rates from the dialysis probe to the IR detector via the second tube.

26. The method of claim 18, wherein the perfusate does not include a recovery marker.

27. The method of claim 18, wherein a concentration of the lactate and/or the pyruvate in the dialysate is one of: at most 10 mM, at most 5 mM, or at most 1 mM.

28. The method of claim 18, further comprising predicting respective concentrations of one or more of lactate, pyruvate or glucose in the dialysate using a model, relating the respective absorbances and the respective concentrations.

29. The method of claim 28, further comprising generating the model using synthetic samples of the dialysate.

30. The method of claim 18, further comprising:

determining, by the controller, the ratio of lactate to pyruvate in the dialysate in real time.

31. The method of claim 18, further comprising:

determining, by the controller, the ratio of lactate to pyruvate in the dialysate online.

* * * * *